US010775375B2

(12) United States Patent
McGrane et al.

(10) Patent No.: US 10,775,375 B2
(45) Date of Patent: *Sep. 15, 2020

(54) METHODS FOR IDENTIFYING MODULATORS OF CALCIUM-SENSING RECEPTORS

(71) Applicant: MARS, INCORPORATED, McLean, VA (US)

(72) Inventors: Scott Joseph McGrane, Leicestershire (GB); Andrew John Taylor, Leicestershire (GB); Richard Masten Fine, Ridgewood, NJ (US); Boris Klebansky, Demarest, NJ (US); Matthew Ronald Gibbs, Leicestershire (GB)

(73) Assignee: MARS, INCORPORATED, McLean, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/450,462

(22) Filed: Jun. 24, 2019

(65) Prior Publication Data

US 2019/0324031 A1 Oct. 24, 2019

Related U.S. Application Data

(63) Continuation of application No. 15/517,409, filed as application No. PCT/US2015/055149 on Oct. 12, 2015, now Pat. No. 10,393,740.

(60) Provisional application No. 62/062,717, filed on Oct. 10, 2014.

(51) Int. Cl.
*G01N 33/566* (2006.01)
*G01N 33/84* (2006.01)

(52) U.S. Cl.
CPC .......... *G01N 33/566* (2013.01); *G01N 33/84* (2013.01); *G01N 2500/04* (2013.01)

(58) Field of Classification Search
CPC ... G01N 33/566; G01N 33/84; G01N 2500/04
See application file for complete search history.

(56) References Cited

U.S. PATENT DOCUMENTS

| 4,597,970 | A | 7/1986 | Sharma et al. |
| 4,722,845 | A | 2/1988 | Cherukuri et al. |
| 8,697,380 | B2 | 4/2014 | Doumazane et al. |
| 8,796,485 | B2 | 8/2014 | Sugiki et al. |
| 2003/0186873 | A1 | 10/2003 | Eishingdrelo et al. |
| 2012/0115176 | A1 | 5/2012 | Doumazane et al. |

FOREIGN PATENT DOCUMENTS

| EP | 2 345 636 A1 | 7/2011 |
| WO | WO 00/006601 A1 | 2/2000 |

OTHER PUBLICATIONS

U.S. Appl. No. 15/517,409 (U.S. Pat. No. 10,393,740), filed Apr. 6, 2017 (Aug. 27, 2019).
U.S. Appl. No. 15/517,409, Jun. 24, 2019 Issue Fee Payment.
U.S. Appl. No. 15/517,409, Apr. 17, 2019 Notice of Allowance.
U.S. Appl. No. 15/517,409, Apr. 4, 2019 Notice of Allowance.
U.S. Appl. No. 15/517,409, Feb. 25, 2019 Response to Non-Final Office Action.
U.S. Appl. No. 15/517,409, Nov. 23, 2018 Non-Final Office Action.
U.S. Appl. No. 15/517,409, Sep. 11, 2018 Response to Restriction Requirement.
U.S. Appl. No. 15/517,409, Aug. 16, 2018 Restriction Requirement.
Altschul et al., "Basic Local Alignment Search Tool," J. Mol. Biol., 215:403-410 (1990).
Altschul et al., "Gapped BLAST and PSI-BLAST: A New Generation of Protein Database Search Programs," Nucleic Acids Research, 25(17):3389-3402 (1997).
Binet et al., "Common Structural Requirements for Heptahelical Domain Function in Class A and Class C G Protein-Coupled Receptors," J. Biol. Chem., 282(16):12154-12163 (2007).
Blankenship et al., "The Calcium-sensing Receptor Regulates Calcium Absorption in MDCK Cells by Inhibition of PMCA," Am. J. Physiol. Renal. Physiol., 280:F815-F822 , (2001).
Brauner-Osborne et al., "The Agonist-binding Domain of the Calcium-sensing Receptor is Located at the Amino-Terminal Domain," Journal of Biological Chemistry, 274(26):18382-18386 (1999).
Cartoni et al., "Taste Preference for Fatty Acids is Mediated by GPR40 and GPR120," Journal of Neuroscience, 30(25):8376-8382 (2010).
Cline, "Perspectives for Gene Therapy: Inserting New Genetic Information into Mammalian Cells by Physical Techniques and Viral Vectors," Pharmac. Ther., 29:69-92 (1985).
Conigrave et al., "Aromatic L-Amino Acids Activate the Calcium-Sensing Receptor," J. Nutr., 137(6):1524S-1527S (2007).
Cotten, "Receptor-Mediated Transport of DNA into Eurkaryotic Cells," Methods in Enzymology, 217:618-644 (1993).
Cunningham et al., "High-Resolution Epitope Mapping of hGH-Receptor Interactions by Alanine-Scanning Mutagenesis," Science, 244(4908):1081-1085, Abstract only (2 pgs.) (1989).
Dore et al., "Structure of class C GPCR metabotropic glutamate receptor 5 transmembrane domain," Nature 511(7511):557-62, Epub Jul. 6, 2014 Abstract Only (2 pgs.) (2014).
Dunkel et al., "Molecular and Sensory Characterization of gamma-Glutamyl Peptides as Key Contributors to the Kokumi Taste of Edible Beans (*Phasolus vulgaris* L.)," J. Agric. Food Chem., 55:6712-6719 (2007).
Eswar et al., "Comparative Protein Structure Modeling Using Modeller," Cuff Protoc Bioinformatics, Supplement 15, 3.6.1-5.6. 30, 47 pages (2006).
Ferraguti et al., "Metabotropic glutamate receptors," Cell Tissue Res, 326(2):483-504 (2006).
Gal et al., "Cloning and Sequencing of the Calcium-Sensing Receptor from the Feline Parathyroid Gland," Domestic Animal Endocrinology, 38:57-61 (2010).

(Continued)

*Primary Examiner* — Ruixiang Li
(74) *Attorney, Agent, or Firm* — Baker Botts L.L.P.

(57) ABSTRACT

Methods for identifying compounds that modulate the activity and/or expression of a calcium-sensing receptor, wherein said compounds can be incorporated into flavor compositions that can be used to modify the kokumi taste and/or palatability of pet food products.

15 Claims, 42 Drawing Sheets

Specification includes a Sequence Listing.

(56) References Cited

OTHER PUBLICATIONS

International Search Report and Written Opinion dated Feb. 2, 2016 in International Application No. PCT/US2015/055149 (12 pages).
Jensen et al., "Allosteric Modulation of the Calcium-Sensing Receptor," Current Neuropharmacology, 5(3):180-186 (2007).
Karlin et al., "Applications and Statistics for Multiple High-Scoring Segments in Molecular Sequences," PNAS USA 90:5873-5877 (1993).
Karlin et al., "Methods for Assessing the Statistical Significance of Molecular Sequence Features by Using General Scoring Schemes," PNAS USA, 87:2264-2268 (1990).
Lee et al., "Structural Insights into Ligand Recognition and Selectivity for Class A, B and C GPCR's," Eur. J. Pharmacol., 763:196-205 (2015).
Liu et al., "Molecular Determinants Involved in the Allosteric Control of Agonist Affinity in the GABAb Receptor by the GABAb2 Subunit," J. Biol. Chem., 279(16):15824-15830 (2004).
Loeffler, "Gene Transfer into Primary and Established Mammalian Cell Lines with Lipopolyamine-Coated DNA," Methods in Enzymology, 217:599-618 (1993).
Malitschek et al., "The N-Terminal Domain of y-Aminobutyric AcidBReceptors is Sufficient to Specify Agonist and Antagonist Binding," Molecular Pharmacology 56(2):448-454 (1999).
Maruyama et al., "Kokumi Substances, Enhancers of Basic Tastes, Induce Responses in Calcium-Sensing Receptor Expressing Taste Cells," PLOS One, 7(4):e34489, 8 pages (2012).
McCaughey et al., "Calcium Deprivation Increases the Palatability of Calcium Solutions in Rats," Physiology & Behavior, 84:335-342 (2005).
Miedlich et al., "Homology Modeling of the Transmembrance Domain of the Human Calcium Sensing Receptor and Localization of an Allosteric Binding Site," Journal of Biological Chemistry, 279(8):7254-7263 (2004).
Myers et al., "Optical Alignments in Linear Space," Comput. Appl. Biosci., 4(1):11-7 Abstract Only (1 pg.) (1988).
Ohsu, "Involvement of the Calcium-Sensing Receptor in Human Taste Perception," The Journal of Biological Chemistry, 285(2):1016-1022 (2010).
Pearson et al., "Improved Tools for Biological Sequence Comparison," PNAS USA, 85:2444-2448 (1988).
Petrel et al., "Positive and Negative Allosteric Modulators of the CA2+-sensing Receptor Interact within Overlapping but Not Identical Binding Sites in the Transmembrane Domain," Journal of Biological Chemistry, 279(18):18990-18997 (2004).
San Gabriel et al., "The Calcium-Sensing Receptor in Taste Tissue," Biochem & Biophys Res. Comm., 378:414-418 (2009).
Toelstede et al., "A Series of Kokumi Peptides Impart the Long-Lasting Mouthfulness of Matured Gouda Cheese," J. Agric. Food Chem., 57:1440-1448 (2009).
Torelli et al., "Advance and Adam: two algorithms for the analysis of global similarity between homologous Informational sequences," Comput. Appl. Biosci., 10:3-5 (1994).
Urwyler, "Allosteric Modulation of Family C G-Protein-Coupled Receptors: from Molecular Insights to Therapeutic Perspectives," Pharmacol Rev, 63:59-126 (2011).
Wu et al., "Structure of a Class C GPCR Metabotropic Glutamate Receptor 1 Bound to an Allosteric Modulator," Science 344:58-64 (2014).

FIG. 1

Feline Calcium-Sensing Receptor Nucleotide Sequence (SEQ ID NO: 1)

```
ATGGCATTTTATAGCTGCTGTTTGATCCTCTTGGCAATTACCTGGTGCACTTCTGCC
TATGGGCCTGACCAACGAGCTCAGAAGAAAGGGGACATTATCCTCGGGGGGCTCTTT
CCTATTCATTTTGGAGTAGCAGCCAAAGATCAAGATCTAAAGTCAAGGCCAGAGTCT
GTGGAATGTATCAGGTATAATTTCCGTGGGTTTCGCTGGTTACAAGCAATGATATTT
GCCATCGAGGAAATAAACAGCAGCCCAGTCCTTCTTCCCAACATGACACTGGGATAC
AGGATATTTGACACTTGCAACACTGTTTCTAAAGCCTTGGAGGCCACTCTGAGTTTT
GTGGCACAAAATAAAATTGATTCTCTGAACCTCGACGAGTTCTGCAACTGCTCAGAG
CATATCCCCTCTACTATCGCTGTGGTGGGAGCAACTGGTTCGGGCATCTCCACAGCG
GTGGCAAACCTGCTGGGCCTCTTCTATATTCCCCAGGTCAGCTATGCCTCCTCCAGC
AGACTCCTCAGCAACAAAATCAGTTCAAGTCCTTTCTCCGTACCATCCCCAATGAT
GAACACCAGGCCACTGCCATGGCAGACATTATCGAGTATTTCCGCTGGAACTGGGTG
GGCACAATTGCTGCTGATGATGACTACGGCCGGCCAGGGATTGAGAAGTTTCGAGAG
GAAGCTGAGGAGAGGGACATCTGCATCGACTTCAGTGAACTCATCTCCCAGTATTCT
GATGAAGAAGAGATCCAGCAAGTGGTGGAGGTGATCCAGAATTCCACAGCCAAAGTC
ATTGTTGTTTTCTCTAGTGGCCCAGACCTTGAACCCCTTATCAAGGAGATTGTCCGG
CGTAATATCACAGGGAGGATCTGGCTGGCCAGCGAGGCCTGGGCCAGCTCTTCCTTG
ATTGCCATGCCCGAGTACTTCCATGTGGTTGGAGGCACCATTGGATTCGCTCTGAAG
GCTGGACAGATCCCAGGTTTCCGGGAATTCCTGCAGAAAGTCCATCCCAGAAAGTCT
GTCCACAATGGTTTTGCCAAGGAGTTTTGGGAAGAAACCTTTAACTGCCACCTCCAA
GAAGGTGCTAAAGGACCTTTAGCACTGGACACTTTCCTGAGAGGTCATGAAGAAGGT
GGTGGCAGGATAAGCAATAGCTCCACTGCCTTGCGACCTCTCTGTACAGGGGACGAG
AACATCAGCAGCGTGGAGACCCCTTACATGGATTATACACATTTACGGATATCCTAC
AATGTCTACTTAGCGGTCTATTCCATTGCTCATGCCCTGCAAGATATATATACATGC
TTACCTGGAAGAGGGCTCTTCACCAATGGTTCCTGCGCAGATATCAAGAAGGTTGAG
GCTTGGCAGGTCCTGAAGCACCTACGGCACCTAAACTTTACCAACAATATGGGGGAG
CAGGTGACTTTCGATGAATGTGGGGACCTGGTGGGAACTATTCCATCATCAACTGG
CACCTCTCTCCAGAGGATGGCTCCATAGTGTTTAAGGAAGTCGGATATTACAACGTC
TATGCCAAGAAAGGAGAAAGGCTCTTCATCAATGAGGAGAAAATCCTGTGGAGTGGA
TTCTCCAGGGAGGTACCTTTCTCCAACTGCAGTCGAGACTGCCTGGCAGGGACCCGG
AAAGGAATCATTGAGGGGGAGCCCACCTGCTGCTTTGAGTGTGTGGAATGTCCTGAT
GGGGAGTACAGTGATGAAACAGATGCAAGTGCCTGTGACAAGTGCCCCGATGACTTC
TGGTCCAATGAGAACCACACTTCTTGCATTGCCAAGGAGATTGAGTTTCTGTCCTGG
ACGGAGCCCTTTGGGATTGCACTCACTCTCTTTGCTGTGCTGGGCATTTTCCTGACA
GCCTTCGTGCTGGGTGTCTTCCTCAAGTTCCGTAACACACCCATTGTCAAGGCTACC
AATCGAGAGCTCTCCTACCTCCTCCTCTTCTCCTTGCTCTGCTGCTTCTCCAGCTCC
CTGTTCTTCATTGGTGAGCCCCAGGACTGGACATGCCGCCTGCGCCAGCCAGCCTTT
GGCATCAGCTTCGTGCTCTGCATATCATGCATCCTAGTGAAAACCAACCGTGTCCTC
CTGGTGTTTGAGGCCAAGATCCCCACGAGCTTCCACCGCAAGTGGTGGGGGCTCAAC
CTGCAGTTCCTGCTGGTCTTCCTCTGCACCTTCATGCAGATTGTCATCTGTGTGATC
TGGCTCTACACTGCACCACCCTCAAGCTACCGCAACCACGAGCTGGAGGATGAGATC
ATCTTTATCACATGCCACGAGGGCTCGCTCATGGCCCTGGCTTCTTAATTGGCTAC
ACCTGCCTACTGGCTGCCATCTGCTTCTTCTTTGCCTTCAAGTCCCGGAAGCTGCCA
GAGAATTTCAATGAAGCCAAGTTCATCACCTTCAGCATGCTCATCTTCTTCATCGTC
TGGATCTCCTTCATCCCAGCCTATGCCAGCACCTATGGCAAGTTTGTCTCTGCCGTG
GAAGTGATCGCCATCCTGGCAGCCAGCTTTGGCTTGCTGGCCTGCATCTTCTTCAAC
AAGGTCTACATCATCCTCTTCAAGCCATCACGTAACACCATCGAGGAGGTGCGCTGC
AGCACTGCTGCCCATGCTTTCAAAGTAGCAGCCCGGGCCACGCTGCGCCGCAGCAAC
```

FIG. 1 CONTINUED

```
GTCTCTCGCAAGCGGTCCAGCAGCCTTGGGGGCTCCACGGGATCCACACCCTCTTCC
TCCATCAGCAGTAAGAGCAACAGTGAAGACCCCTTCCCACAGCCCGAGAGGCAAAAG
CAGCAGCAGCCACTGGCCCTGACCCAACAAGAGCAGCAGCCGCAGCCACAGCAGCCC
TCGTCCCTACAGCAGCAGCCACAGCCACAGCCACAGCCCAGATGCAAGCAGAAAGTC
ATTTTCGGCAGTGGCACAGTCACCTTCTCACTGAGCTTTGATGAGCCTCAGAAGAGT
GCCATGGCTCACAGGAATTCTATGCACCAGAACTCCCTGGAGGCCCAGAAAAGCAAT
GAGACCCTCACCAGACACCAGGCATTACTCCCACTACAGTGCGGGGAGACAGACTCA
GAACTGAGTGCCCAGGAGAGAGGTCTTCAAGGGCCTGTAGATGGGGACTTCCGACCA
GAGATGGAGGACCCTGAAGAGATGTCCCCAGCGCTTGTAGTGTCCAGTTCACAAAGC
TTTGTCATCAGTGGTGGTGGCAGCACTGTCACAGAAAATATACTGCATTCATAA
```

FIG. 2

Canine Calcium-Sensing Receptor Nucleotide Sequence (SEQ ID NO: 2)

```
ATGGCATTTCACAGCTGCTCTTTGATCCTCTTGGCAATCACCTGGTGCACTTCTGCC
TATGGGCCTGACCAACGAGCCCAGAAGAAAGGGGACATTATCCTTGGGGGGCTCTTT
CCTATTCATTTTGGAGTAGCAGCCAAAGATCAAGATCTAAAGTCAAGGCCGGAGTCT
GTGGAATGTATCAGGTACAATTTCCGCGGGTTTCGTTGGTTACAAGCAATGATATTT
GCCATCGAGGAAATAAACAGCAGCCCAGCCCTTCTTCCAAACATGACACTGGGATAC
AGAATATTTGACACTTGCAACACCGTTTCTAAAGCCTTGGAGGCCACTCTGAGTTTT
GTGGCACAGAATAAAATTGATTCTCTGAACCTTGACGAGTTCTGCAACTGCTCAGAG
CATATCCCCTCTACTATCGCTGTGGTGGGAGCAACTGGCTCGGGCATCTCCACGGCT
GTGGCAAACCTGCTGGGCCTCTTCTACATCCCCCAGGTCAGCTATGCCTCCTCCAGC
AGACTCCTCAGCAATAAGAATCAGTTCAAGTCCTTCCTCCGTACCATCCCCAATGAT
GAACACCAGGCCACTGCCATGGCAGACATTATTGAGTATTTCCGCTGGAACTGGGTG
GGCACCATTGCAGCTGATGATGACTACGGCCGGCCAGGGATTGAGAAGTTCCGAGAG
GAAGCAGAGGAGAGGGACATCTGCATCGACTTCAGTGAACTCATCTCCCAGTACTCT
GATGAGGAAGAGATTCAGCAAGTGGTAGAGGTGATCCAGAATTCCACAGCCAAAGTC
ATTGTTGTTTTCTCCAGTGGCCCAGACCTTGAACCCCTCATCAAGGAGATCGTCCGG
CGAAATATCACAGGAAGGATTTGGCTGGCCAGTGAGGCCTGGGCCAGCTCTTCCTTG
ATTGCCATGCCCGAGTACTTCCATGTGGTTGGAGGTACCATTGGATTCGCTTTGAAG
GCTGGGCAGATCCCAGGTTTCCGGGAATTCCTGCAGAAAGTCCATCCCAGAAAGTCT
GTCCACAACGGTTTTGCCAAGGAGTTTTGGGAAGAAACATTTAACTGCCACCTCCAA
GAAGGTGCTAAAGGGCCTTTATCCATGGACACTTTCCTGAGAGGCCACGAAGAAGGT
GGTGGCAGGATAAGCAACAGCTCCACTGCCTTCCGACCTCTTTGCACAGGAGATGAG
AACATCAGTAGTGTGGAGACCCCTTATATGGATTATACACACTTACGGATATCCTAC
AACGTCTACTTAGCAGTCTATTCCATTGCTCATGCCCTGCAAGATATATATACATGC
TTACCTGGGAGAGGGCTCTTCACCAACGGTTCCTGTGCTGATATTAAGAAGGTTGAG
GCTTGGCAGGTCTTGAAGCACCTACGGCACCTAAACTTTACCAACAATATGGGGGAG
CAAGTGACTTTCGATGAATGTGGTGACCTGATGGGGAACTATTCCATCATCAACTGG
CACCTCTCTCCAGAGGATGGCTCCATAGTGTTTAAGGAAGTCGGATATTACAATGTC
TATGCCAAGAAAGGAGAAAGACTCTTCATCAATGAGGAGAAAATCCTGTGGAGTGGG
TTCTCCAGGGAGATGCCATTTTCCAACTGCAGCCGAGACTGCCTGGCAGGGACCAGG
AAAGGAATCATTGAGGGGGAGCCTACCTGCTGCTTTGAGTGTGTGGAGTGCCCCGAC
GGGGAGTACAGTGATGAAACAGATGCAAGTGCCTGTGACAAGTGCCCCGATGACTTC
TGGTCCAATGAAAACCACACTTCGTGCATTGCCAAAGAGATTGAGTTTCTGTCCTGG
ACAGAGCCCTTTGGGATTGCACTCACCCTCTTTGCTGTGCTGGGCATTTTCCTGACA
GCTTTCGTGCTGGGGGTCTTCATCAAGTTCCGTAACACGCCCATCGTCAAGGCCACC
AACCGAGAGCTCTCGTACCTCCTCCTCTTCTCCTTGCTGTGCTGCTTCTCCAGCTCC
CTGTTCTTCATTGGCGAGCCCCAGGACTGGACCTGCCGCCTGCGCCAGCCGGCCTTT
GGCATCAGCTTCGTGCTCTGCATATCATGCATCCTGGTGAAAACCAACCGTGTCCTC
CTGGTGTTTGAGGCCAAGATCCCCACAAGCTTCCACCGCAAGTGGTGGGGCTCAAC
CTGCAGTTCCTGCTGGTCTTCCTCTGCACCTTCATGCAGATTGTCATCTGTGTGATC
TGGCTCTACACGGCGCCTCCCTCCAGCTACCGCAACCATGAGCTGGAGGACGAGATC
ATCTTCATCACATGCCACGAGGGCTCCCTGATGGCCCTGGGCTTCCTGATTGGCTAC
ACCTGCCTGCTGGCTGCCATCTGCTTCTTCTTTGCCTTCAAGTCCCGGAAGCTGCCG
GAGAACTTCAACGAGGCCAAGTTCATCACCTTCAGCATGCTCATCTTCTTCATCGTC
TGGATCTCCTTCATTCCAGCCTACGCCAGCACCTACGGCAAGTTTGTCTCTGCCGTG
GAAGTGATCGCCATCCTGGCCGCCAGCTTTGGCCTCCTGGCCTGCATCTTCTTCAAC
AAGGTGTACATCATCCTCTTCAAGCCGTCCCGCAACACCATCGAGGAGGTGCGCTGC
AGCACCGCGGCTCACGCTTTCAAGGTCGCGGCCCGCGCCACGCTGCGCCGCAGCAAC
```

FIG. 2 CONTINUED

```
GTCTCCCGCAAGCGGTCCGGCAGCCTGGGGGGCTCCACGGGCTCCACGCCCTCCTCC
TCCATCAGCAGCAAGAGCAACAGTGAAGACCCCTTCCCGCAGCCCGAGAGGCAGAAG
CAGCAGCAGCCCCTGGCCCTGACCCAGCGGGAGCAGCAGCCGCCGCAGCCCTTGACC
TTGCCGCCGCAGCCGCAGCCCAGGTGCAAGCAGAAGGTCATCTTCGGCAGTGGCACC
GTCACCTTCTCGCTGAGCTTTGACGAGCCGCAGAAGAGCGCCGCGGCCCCCGCAAT
TCCACGCTGCAGCACTCCCTGGAGGCCCAGCGGAGCCCCGAGCCCCCGCCAGACCC
CAGGCGTTACTGCCGCCGCAGGGCGGAGACACAGACGCGGAGCTGCCGGCCCAGGAG
CCGGGCCTGCAGGGCCCCGGGGGTGCGGACCGCCGCCCGGAGATGCGAGACCCCGAA
GAGCTGTCCCCAGCCCTGGTGGTGTCCAGCTCACAAAGCTTTGTCATCAGCGGCGGA
GGCAGCACGGTCACGGAAAACATACTGCATTCGTAA
```

FIG. 3

Human Calcium-Sensing Receptor Nucleotide Sequence (SEQ ID NO: 3)

```
ATGGCATTTTATAGCTGCTGCTGGGTCCTCTTGGCACTCACCTGGCACACCTCTGCC
TACGGGCCAGACCAGCGAGCCCAAAAGAAGGGGGACATTATCCTTGGGGGGCTCTTT
CCTATTCATTTTGGAGTAGCAGCTAAAGATCAAGATCTCAAATCAAGGCCGGAGTCT
GTGGAATGTATCAGGTATAATTTCCGTGGGTTTCGCTGGTTACAGGCTATGATATTT
GCCATAGAGGAGATAAACAGCAGCCCAGCCCTTCTTCCCAACTTGACGCTGGGATAC
AGGATATTTGACACTTGCAACACCGTTTCTAAGGCCTTGGAAGCCACCCTGAGTTTT
GTTGCTCAAAACAAAATTGATTCTTTGAACCTTGATGAGTTCTGCAACTGCTCAGAG
CACATTCCCTCTACGATTGCTGTGGTGGGAGCAACTGGCTCAGGCGTCTCCACGGCA
GTGGCAAATCTGCTGGGGCTCTTCTACATTCCCCAGGTCAGTTATGCCTCCTCCAGC
AGACTCCTCAGCAACAAGAATCAATTCAAGTCTTTCCTCCGAACCATCCCCAATGAT
GAGCACCAGGCCACTGCCATGGCAGACATCATCGAGTATTTCCGCTGGAACTGGGTG
GGCACAATTGCAGCTGATGACGACTATGGGCGGCCGGGGATTGAGAAATTCCGAGAG
GAAGCTGAGGAAAGGGATATCTGCATCGACTTCAGTGAACTCATCTCCCAGTACTCT
GATGAGGAAGAGATCCAGCATGTGGTAGAGGTGATTCAAAATTCCACGGCCAAAGTC
ATCGTGGTTTTCTCCAGTGGCCCAGATCTTGAGCCCCTCATCAAGGAGATTGTCCGG
CGCAATATCACGGGCAAGATCTGGCTGGCCAGCGAGGCCTGGGCCAGCTCCTCCCTG
ATCGCCATGCCTCAGTACTTCCACGTGGTTGGCGGCACCATTGGATTCGCTCTGAAG
GCTGGGCAGATCCCAGGCTTCCGGGAATTCCTGAAGAAGGTCCATCCCAGGAAGTCT
GTCCACAATGGTTTTGCCAAGGAGTTTTGGGAAGAAACATTTAACTGCCACCTCCAA
GAAGGTGCAAAAGGACCTTTACCTGTGGACACCTTTCTGAGAGGTCACGAAGAAAGT
GGCGACAGGTTTAGCAACAGCTCGACAGCCTTCCGACCCCTCTGTACAGGGGATGAG
AACATCAGCAGTGTCGAGACCCCTTACATAGATTACACGCATTTACGGATATCCTAC
AATGTGTACTTAGCAGTCTACTCCATTGCCCACGCCTTGCAAGATATATATACCTGC
TTACCTGGGAGAGGGCTCTTCACCAATGGCTCCTGTGCAGACATCAAGAAAGTTGAG
GCGTGGCAGGTCCTGAAGCACCTACGGCATCTAAACTTTACAAACAATATGGGGGAG
CAGGTGACCTTTGATGAGTGTGGTGACCTGGTGGGAACTATTCCATCATCAACTGG
CACCTCTCCCCAGAGGATGGCTCCATCGTGTTTAAGGAAGTCGGGTATTACAACGTC
TATGCCAAGAAGGGAGAAAGACTCTTCATCAACGAGGAGAAAATCCTGTGGAGTGGG
TTCTCCAGGGAGGTGCCCTTCTCCAACTGCAGCCGAGACTGCCTGGCAGGGACCAGG
AAAGGGATCATTGAGGGGGAGCCCACCTGCTGCTTTGAGTGTGTGGAGTGTCCTGAT
GGGGAGTATAGTGATGAGACAGATGCCAGTGCCTGTAACAAGTGCCCAGATGACTTC
TGGTCCAATGAGAACCACACCTCCTGCATTGCCAAGGAGATCGAGTTTCTGTCGTGG
ACGGAGCCCTTTGGGATCGCACTCACCCTCTTTGCCGTGCTGGGCATTTTCCTGACA
GCCTTTGTGCTGGGTGTGTTTATCAAGTTCCGCAACACACCCATTGTCAAGGCCACC
AACCGAGAGCTCTCCTACCTCCTCCTCTTCTCCCTGCTCTGCTGCTTCTCCAGCTCC
CTGTTCTTCATCGGGGAGCCCCAGGACTGGACGTGCCGCCTGCGCCAGCCGGCCTTT
GGCATCAGCTTCGTGCTCTGCATCTCATGCATCCTGGTGAAAACCAACCGTGTCCTC
CTGGTGTTTGAGGCCAAGATCCCCACCAGCTTCCACCGCAAGTGGTGGGGCTCAAC
CTGCAGTTCCTGCTGGTTTTCCTCTGCACCTTCATGCAGATTGTCATCTGTGTGATC
TGGCTCTACACCGCGCCCCGTCAAGCTACCGCAACCAGGAGCTGGAGGATGAGATC
ATCTTCATCACGTGCCACGAGGGCTCCCTCATGGCCCTGGGCTTCCTGATCGGCTAC
ACCTGCCTGCTGGCTGCCATCTGCTTCTTCTTTGCCTTCAAGTCCCGGAAGCTGCCG
GAGAACTTCAATGAAGCCAAGTTCATCACCTTCAGCATGCTCATCTTCTTCATCGTC
TGGATCTCCTTCATTCCAGCCTATGCCAGCACCTATGGCAAGTTTGTCTCTGCCGTA
GAGGTGATTGCCATCCTGGCAGCCAGCTTTGGCTTGCTGGCGTGCATCTTCTTCAAC
AAGATCTACATCATTCTCTTCAAGCCATCCCGCAACACCATCGAGGAGGTGCGTTGC
AGCACCGCAGCTCACGCTTTCAAGGTGGCTGCCCGGGCCACGCTGCGCCGCAGCAAC
```

FIG. 3 CONTINUED

```
GTCTCCCGCAAGCGGTCCAGCAGCCTTGGAGGCTCCACGGGATCCACCCCCTCCTCC
TCCATCAGCAGCAAGAGCAACAGCGAAGACCCATTCCCACAGCCCGAGAGGCAGAAG
CAGCAGCAGCCGCTGGCCCTAACCCAGCAAGAGCAGCAGCAGCAGCCCCTGACCCTC
CCACAGCAGCAACGATCTCAGCAGCAGCCCAGATGCAAGCAGAAGGTCATCTTTGGC
AGCGGCACGGTCACCTTCTCACTGAGCTTTGATGAGCCTCAGAAGAACGCCATGGCC
CACAGGAATTCTACGCACCAGAACTCCCTGGAGGCCCAGAAAAGCAGCGATACGCTG
ACCCGACACGAGCCATTACTCCCGCTGCAGTGCGGGGAAACGGACTTAGATCTGACC
GTCCAGGAAACAGGTCTGCAAGGACCTGTGGGTGGAGACCAGCGGCCAGAGGTGGAG
GACCCTGAAGAGTTGTCCCCAGCACTTGTAGTGTCCAGTTCACAGAGCTTTGTCATC
AGTGGTGGAGGCAGCACTGTTACAGAAAACGTAGTGAATTCATAA
```

FIG. 4

Feline Calcium-Sensing Receptor Amino Acid Sequence (SEQ ID NO: 4)

MAFYSCCLILLAITWCTSAYGPDQRAQKKGDIILGGLFPIHFGVAAKDQDLKSRPES
VECIRYNFRGFRWLQAMIFAIEEINSSPVLLPNMTLGYRIFDTCNTVSKALEATLSF
VAQNKIDSLNLDEFCNCSEHIPSTIAVVGATGSGISTAVANLLGLFYIPQVSYASSS
RLLSNKNQFKSFLRTIPNDEHQATAMADIIEYFRWNWVGTIAADDDYGRPGIEKFRE
EAEERDICIDFSELISQYSDEEEIQQVVEVIQNSTAKVIVVFSSGPDLEPLIKEIVR
RNITGRIWLASEAWASSSLIAMPEYFHVVGGTIGFALKAGQIPGFREFLQKVHPRKS
VHNGFAKEFWEETFNCHLQEGAKGPLALDTFLRGHEEGGGRISNSSTALRPLCTGDE
NISSVETPYMDYTHLRISYNVYLAVYSIAHALQDIYTCLPGRGLFTNGSCADIKKVE
AWQVLKHLRHLNFTNNMGEQVTFDECGDLVGNYSIINWHLSPEDGSIVFKEVGYYNV
YAKKGERLFINEEKILWSGFSREVPFSNCSRDCLAGTRKGIIEGEPTCCFECVECPD
GEYSDETDASACDKCPDDFWSNENHTSCIAKEIEFLSWTEPFGIALTLFAVLGIFLT
AFVLGVFLKFRNTPIVKATNRELSYLLLFSLLCCFSSSLFFIGEPQDWTCRLRQPAF
GISFVLCISCILVKTNRVLLVFEAKIPTSFHRKWWGLNLQFLLVFLCTFMQIVICVI
WLYTAPPSSYRNHELEDEIIFITCHEGSLMALGFLIGYTCLLAAICFFFAFKSRKLP
ENFNEAKFITFSMLIFFIVWISFIPAYASTYGKFVSAVEVIAILAASFGLLACIFFN
KVYIILFKPSRNTIEEVRCSTAAHAFKVAARATLRRSNVSRKRSSSLGGSTGSTPSS
SISSKSNSEDPFPQPERQKQQQPLALTQQEQQPQPQQPSSLQQQPQPQPQPRCKQKV
IFGSGTVTFSLSFDEPQKSAMAHRNSMHQNSLEAQKSNETLTRHQALLPLQCGETDS
ELSAQERGLQGPVDGDFRPEMEDPEEMSPALVVSSSQSFVISGGGSTVTENILHS

FIG. 5

Canine Calcium-Sensing Receptor Amino Acid Sequence (SEQ ID NO: 5)

MAFHSCSLILLAITWCTSAYGPDQRAQKKGDIILGGLFPIHFGVAAKDQDLKSRPES
VECIRYNFRGFRWLQAMIFAIEEINSSPALLPNMTLGYRIFDTCNTVSKALEATLSF
VAQNKIDSLNLDEFCNCSEHIPSTIAVVGATGSGISTAVANLLGLFYIPQVSYASSS
RLLSNKNQFKSFLRTIPNDEHQATAMADIIEYFRWNWVGTIAADDDYGRPGIEKFRE
EAEERDICIDFSELISQYSDEEEIQQVVEVIQNSTAKVIVVFSSGPDLEPLIKEIVR
RNITGRIWLASEAWASSSLIAMPEYFHVVGGTIGFALKAGQIPGFREFLQKVHPRKS
VHNGFAKEFWEETFNCHLQEGAKGPLSMDTFLRGHEEGGGRISNSSTAFRPLCTGDE
NISSVETPYMDYTHLRISYNVYLAVYSIAHALQDIYTCLPGRGLFTNGSCADIKKVE
AWQVLKHLRHLNFTNNMGEQVTFDECGDLMGNYSIINWHLSPEDGSIVFKEVGYYNV
YAKKGERLFINEEKILWSGFSREMPFSNCSRDCLAGTRKGIIEGEPTCCFECVECPD
GEYSDETDASACDKCPDDFWSNENHTSCIAKEIEFLSWTEPFGIALTLFAVLGIFLT
AFVLGVFIKFRNTPIVKATNRELSYLLLFSLLCCFSSSLFFIGEPQDWTCRLRQPAF
GISFVLCISCILVKTNRVLLVFEAKIPTSFHRKWWGLNLQFLLVFLCTFMQIVICVI
WLYTAPPSSYRNHELEDEIIFITCHEGSLMALGFLIGYTCLLAAICFFFAFKSRKLP
ENFNEAKFITFSMLIFFIVWISFIPAYASTYGKFVSAVEVIAILAASFGLLACIFFN
KVYIILFKPSRNTIEEVRCSTAAHAFKVAARATLRRSNVSRKRSGSLGGSTGSTPSS
SISSKSNSEDPFPQPERQKQQQPLALTQREQQPPQPLTLPPQPQPRCKQKVIFGSGT
VTFSLSFDEPQKSAAAPRNSTLQHSLEAQRSPEPPARPQALLPPQGGDTDAELPAQE
PGLQGPGGADRRPEMRDPEELSPALVVSSSQSFVISGGGSTVTENILHS

FIG. 6

Human Calcium-Sensing Receptor Amino Acid Sequence (SEQ ID NO: 6)

MAFYSCCWVLLALTWHTSAYGPDQRAQKKGDIILGGLFPIHFGVAAKDQDLKSRPES
VECIRYNFRGFRWLQAMIFAIEEINSSPALLPNLTLGYRIFDTCNTVSKALEATLSF
VAQNKIDSLNLDEFCNCSEHIPSTIAVVGATGSGVSTAVANLLGLFYIPQVSYASSS
RLLSNKNQFKSFLRTIPNDEHQATAMADIIEYFRWNWVGTIAADDDYGRPGIEKFRE
EAEERDICIDFSELISQYSDEEEIQHVVEVIQNSTAKVIVVFSSGPDLEPLIKEIVR
RNITGKIWLASEAWASSSLIAMPQYFHVVGGTIGFALKAGQIPGFREFLKKVHPRKS
VHNGFAKEFWEETFNCHLQEGAKGPLPVDTFLRGHEESGDRFSNSSTAFRPLCTGDE
NISSVETPYIDYTHLRISYNVYLAVYSIAHALQDIYTCLPGRGLFTNGSCADIKKVE
AWQVLKHLRHLNFTNNMGEQVTFDECGDLVGNYSIINWHLSPEDGSIVFKEVGYYNV
YAKKGERLFINEEKILWSGFSREVPFSNCSRDCLAGTRKGIIEGEPTCCFECVECPD
GEYSDETDASACNKCPDDFWSNENHTSCIAKEIEFLSWTEPFGIALTLFAVLGIFLT
AFVLGVFIKFRNTPIVKATNRELSYLLLFSLLCCFSSSLFFIGEPQDWTCRLRQPAF
GISFVLCISCILVKTNRVLLVFEAKIPTSFHRKWWGLNLQFLLVFLCTFMQIVICVI
WLYTAPPSSYRNQELEDEIIFITCHEGSLMALGFLIGYTCLLAAICFFFAFKSRKLP
ENFNEAKFITFSMLIFFIVWISFIPAYASTYGKFVSAVEVIAILAASFGLLACIFFN
KIYIILFKPSRNTIEEVRCSTAAHAFKVAARATLRRSNVSRKRSSSLGGSTGSTPSS
SISSKSNSEDPFPQPERQKQQQPLALTQQEQQQQPLTLPQQQRSQQQPRCKQKVIFG
SGTVTFSLSFDEPQKNAMAHRNSTHQNSLEAQKSSDTLTRHEPLLPLQCGETDLDLT
VQETGLQGPVGGDQRPEVEDPEELSPALVVSSSQSFVISGGGSTVTENVVNS

FIG. 7

Alignment of the Human (hCaSR) and Feline (fCaSR) CaSR Sequences

```
hCaSR     MAFYSCCWVLLALTWHTSAYGPDQRAQKKGDIILGGLFPIHFGVAAKDQDLKSRPESVEC
fCaSR     MAFYSCCLILLAITWCTSAYGPDQRAQKKGDIILGGLFPIHFGVAAKDQDLKSRPESVEC
          *****:*: ******************************************* hCaSR     IPYNFRGFRWLQAMIFAIEEINSSPALLPNLTLGYRIFDTCNTVSKALEATLSFVAQNKI
fCaSR     IPYNFRGFRWLQAMIFAIEEINSSPVLLPNMTLGYRIFDTCNTVSKALEATLSFVAQNKI
          ***********************.:*************************** hCaSR     DSLNLDEFCNCSEHIPSTIAVVGATGSGVSTAVANLLGLFYIPQVSYASSSRLLSNKNQF
fCaSR     DSLNLDEFCNCSEHIPSTIAVVGATGSGISTAVANLLGLFYIPQVSYASSSRLLSNKNQF
          **************************:***************************** hCaSR     KSFLRTIPNDEHQATAMADIIEYFRWNWVGTIAADDDYGRPGIEKFREEAEERDICIDFS
fCaSR     KSFLRTIPNDEHQATAMADIIEYFRWNWVGTIAADDDYGRPGIEKFREEAEERDICIDFS
          ************************************************************ hCaSR     ELISQYSDEEEIQHVVEVIQNSTAKVIVVFSSGPDLEPLIKEIVRRNITGKIWLASEAWA
fCaSR     ELISQYSDEEEIQQVVEVIQNSTAKVIVVFSSGPDLEPLIKEIVRRNITGRIWLASEAWA
          ***********:*******************************:******** hCaSR     SSSLIAMPQYFHVVGGTIGFALKAGQIPGFREFLKKVHPRKSVHNGFAKEFWEETFNCHL
fCaSR     SSSLIAMPEYFHVVGGTIGFALKAGQIPGFREFLQKVHPRKSVHNGFAKEFWEETFNCHL
          ******:*********************:*********************** hCaSR     QEGAKGPLPVDTFLRGHEESGDRFSNSSTAFRPLCTGDENISSVETPYIDYTHLRISYNV
fCaSR     QEGAKGPLALDTFLRGHEEGGGRISNSSTALRPLCTGDENISSVETPYMDYTHLRISYNV
          ******:.*******.* *:****:*************:********* hCaSR     YLAVYSIAHALQDIYTCLPGRGLFTNGSCADIKKVEAWQVLKHLRHLNFTNNMGEQVTFD
fCaSR     YLAVYSIAHALQDIYTCLPGRGLFTNGSCADIKKVEAWQVLKHLRHLNFTNNMGEQVTFD
          ************************************************************ hCaSR     ECGDLVGNYSIINWHLSPEDGSIVFKEVGYYNVYAKKGERLFINEEKILWSGFSREVPFS
fCaSR     ECGDLVGNYSIINWHLSPEDGSIVFKEVGYYNVYAKKGERLFINEEKILWSGFSREVPFS
          ************************************************************ hCaSR     NCSRDCLAGTRKGIIEGEPTCCFECVECPDGEYSDETDASACNKCPDDFWSNENHTSCIA
fCaSR     NCSRDCLAGTRKGIIEGEPTCCFECVECPDGEYSDETDASACDKCPDDFWSNENHTSCIA
          ***************************************:**************** hCaSR     KEIEFLSWTEPFGIALTLFAVLGIFLTAFVLGVFIKFRNTPIVKATNRELSYLLLFSLLC
fCaSR     KEIEFLSWTEPFGIALTLFAVLGIFLTAFVLGVFLKFRNTPIVKATNRELSYLLLFSLLC
          *******************************:************************ hCaSR     CFSSSLFFIGEPQDWTCRLRQPAFGISFVLCISCILVKTNRVLLVFEAKIPTSFHRKWWG
fCaSR     CFSSSLFFIGEPQDWTCRLRQPAFGISFVLCISCILVKTNRVLLVFEAKIPTSFHRKWWG
          ************************************************************ hCaSR     LNLQFLLVFLCTFMQIVICVIWLYTAPPSSYRNQELEDEIIFITCHEGSLMALGFLIGYT
fCaSR     LNLQFLLVFLCTFMQIVICVIWLYTAPPSSYRNHELEDEIIFITCHEGSLMALGFLIGYT
          ******************************:************************* hCaSR     CLLAAICFFFAFKSRKLPENFNEAKFITFSMLIFFIVWISFIPAYASTYGKFVSAVEVIA
fCaSR     CLLAAICFFFAFKSRKLPENFNEAKFITFSMLIFFIVWISFIPAYASTYGKFVSAVEVIA
          ************************************************************ hCaSR     ILAASFGLLACIFFNKIYIILFKPSRNTIEEVRCSTAAHAFKVAARATLRRSNVSRKRSS
fCaSR     ILAASFGLLACIFFNKVYIILFKPSRNTIEEVRCSTAAHAFKVAARATLRRSNVSRKRSS
          *************:****************************************** hCaSR     SLGGSTGSTPSSSISSKSNSEDPFPQPERQKQQQPLALTQQEQQQQ---PLTLPQQQRSQ
fCaSR     SLGGSTGSTPSSSISSKSNSEDPFPQPERQKQQQPLALTQQEQQPQPQQPSSLQQQPQPQ
          ********************************************  *   *:* ** : *
```

FIG. 7 CONTINUED

```
hCaSR     QQPRCKQKVIFGSGTVTFSLSFDEPQKNAMAHRNSTHQNSLEAQKSSDTLTRHEPLLPLQ
fCaSR     PQPRCKQKVIFGSGTVTFSLSFDEPQKSAMAHRNSMHQNSLEAQKSNETLTRHQALLPLQ
          ******************.**.******:;*:.*** hCaSR     CGETDLDLTVQETGLQGPVGGDQRPEVEDPEELSPALVVSSSQSFVISGGGSTVTENVVN
fCaSR     CGETDSELSAQERGLQGPVDGDFRPEMEDPEEMSPALVVSSSQSFVISGGGSTVTENILH
          *****:*:.** ****** ** ***;****;*************************:;.

hCaSR     S*
fCaSR     S*
          **
```

FIG. 8

Alignment of the Human (hCaSR) and Canine (cCaSR) CaSR Sequences

```
hCaSR     MAFYSCCWVLLALTWHTSAYGPDQRAQKKGDIILGGLFPIHFGVAAKDQDLKSRPESVEC
cCaSR     MAFHSCSLILLAITWCTSAYGPDQRAQKKGDIILGGLFPIHFGVAAKDQDLKSRPESVEC
          *:. :*: ******************************************** hCaSR     IRYNFRGFRWLQAMIFAIEEINSSPALLPNLTLGYRIFDTCNTVSKALEATLSFVAQNKI
cCaSR     IRYNFRGFRWLQAMIFAIEEINSSPALLPNMTLGYRIFDTCNTVSKALEATLSFVAQNKI
          ***************************:**************************** hCaSR     DSLNLDEFCNCSEHIPSTIAVVGATGSGVSTAVANLLGLFYIPQVSYASSSRLLSNKNQF
cCaSR     DSLNLDEFCNCSEHIPSTIAVVGATGSGISTAVANLLGLFYIPQVSYASSSRLLSNKNQF
          **************************:***************************** hCaSR     KSFLRTIPNDEHQATAMADIIEYFRWNWVGTIAADDDYGRPGIEKFREEAEERDICIDFS
cCaSR     KSFLRTIPNDEHQATAMADIIEYFRWNWVGTIAADDDYGRPGIEKFREEAEERDICIDFS
          ************************************************************ hCaSR     ELISQYSDEEEIQHVVEVIQNSTAKVIVVFSSGPDLEPLIKEIVRRNITGKIWLASEAWA
cCaSR     ELISQYSDEEEIQQVVEVIQNSTAKVIVVFSSGPDLEPLIKEIVRRNITGRIWLASEAWA
          ***********:********************************:******* hCaSR     SSSLIAMPQYFHVVGGTIGFALKAGQIPGFREFLKKVHPRKSVHNGFAKEFWEETFNCHL
cCaSR     SSSLIAMPEYFHVVGGTIGFALKAGQIPGFREFLQKVHPRKSVHNGFAKEFWEETFNCHL
          ******:*********************:*********************** hCaSR     QEGAKGPLPVDTFLRGHEESGDRFSNSSTAFRPLCTGDENISSVETPYIDYTHLRISYNV
cCaSR     QEGAKGPLSMDTFLRGHEEGGGRISNSSTAFRPLCTGDENISSVETPYMDYTHLRISYNV
          ******.:******* .* *:*********************:********* hCaSR     YLAVYSIAHALQDIYTCLPGRGLFTNGSCADIKKVEAWQVLKHLRHLNFTNNMGEQVTFD
cCaSR     YLAVYSIAHALQDIYTCLPGRGLFTNGSCADIKKVEAWQVLKHLRHLNFTNNMGEQVTFD
          ************************************************************ hCaSR     ECGDLVGNYSIINWHLSPEDGSIVFKEVGYYNVYAKKGERLFINEEKILWSGFSREVPFS
cCaSR     ECGDLMGNYSIINWHLSPEDGSIVFKEVGYYNVYAKKGERLFINEEKILWSGFSREMPFS
          ***:**********************************************:* hCaSR     NCSRDCLAGTRKGIIEGEPTCCFECVECPDGEYSDETDASACNKCPDDFWSNENHTSCIA
cCaSR     NCSRDCLAGTRKGIIEGEPTCCFECVECPDGEYSDETDASACDKCPDDFWSNENHTSCIA
          ****************************************:*************** hCaSR     KEIEFLSWTEPFGIALTLFAVLGIFLTAFVLGVFIKFRNTPIVRATNRELSYLLLFSLLC
cCaSR     KEIEFLSWTEPFGIALTLFAVLGIFLTAFVLGVFIKFRNTPIVRATNRELSYLLLFSLLC
          ************************************************************ hCaSR     CFSSSLFFIGEPQDWTCRLRQPAFGISFVLCISCILVKTNRVLLVFEAKIPTSFHRKWWG
cCaSR     CFSSSLFFIGEPQDWTCRLRQPAFGISFVLCISCILVKTNRVLLVFEAKIPTSFHRKWWG
          ************************************************************ hCaSR     LNLQFLLVFLCTFMQIVICVIWLYTAPPSSYRNQELEDEIIFITCHEGSLMALGFLIGYT
cCaSR     LNLQFLLVFLCTFMQIVICVIWLYTAPPSSYRNHELEDEIIFITCHEGSLMALGFLIGYT
          ******************************:************************* hCaSR     CLLAAICFFAFKSRKLPENFNEAKFITFSMLIFFIVWISFIPAYASTYGKFVSAVEVIA
cCaSR     CLLAAICFFAFKSRKLPENFNEAKFITFSMLIFFIVWISFIPAYASTYGKFVSAVEVIA
          ************************************************************ hCaSR     ILAASFGLLACIFFNKIYIILFKPSRNTIEEVRCSTAAHAFKVAARATLRRSNVSRKRSS
cCaSR     ILAASFGLLACIFFNKVYIILFKPSRNTIEEVRCSTAAHAFKVAARATLRRSNVSRKRSG
          ****************:******************************************.

hCaSR     SLGGSTGSTPSSSISSKSNSEDPFPQPERQKQQQPLALTQQEQQ-QQPLTLPQQQRSQQQ
cCaSR     SLGGSTGSTPSSSISSKSNSEDPFPQPERQKQQQPLALTQREQQPFQPLTLP----PQPQ
          ****************************************:*** ******    * *
```

FIG. 8 CONTINUED

```
hCaSR    PRCKQKVIFGSGTVTFSLSFDEPQKNAMAHRNSTHQNSLEAQKSSDTLTRHEPLLPLQCG
cCaSR    PRCKQKVIFGSGTVTFSLSFDEPQKSAAAPRNSTLQHSLEAQRSPEPPARPQALLPPQGG
         ************************.* * **** *.*****:*  :  :* : *** * * hCaSR    ETDLDLTVQETGLQGPVGGDQRPEVEDPEELSPALVVSSSQSFVISGGGSTVTENVVNS*
cCaSR    DTDAELPAQEFGLQGPGGADRRPEMPDPEELSPALVVSSSQSFVISGGGSTVTENILHS*
         :** :* .** ***** *.*;***;.***************************:;.**
```

FIG. 9

Alignment of the Canine (cCaSR) and Feline (fCaSR) CaSR Sequences

```
cCaSR    MAFHSCSLILLAITWCTSAYGPDQRAQKKGDIILGGLFPIHFGVAAKDQDLKSRPESVEC
fCaSR    MAFYSCCLILLAITWCTSAYGPDQRAQKKGDIILGGLFPIHFGVAAKDQDLKSRPESVEC
         *:.***************************************************** cCaSR    IRYNFRGFRWLQAMIFAIEEINSSPALLPNMTLGYRIFDTCNTVSKALEATLSFVAQNKI
fCaSR    IRYNFRGFRWLQAMIFAIEEINSSPVLLPNMTLGYRIFDTCNTVSKALEATLSFVAQNKI
         ***********************.******************************** cCaSR    DSLNLDEFCNCSEHIPSTIAVVGATGSGISTAVANLLGLFYIPQVSYASSSRLLSNKNQF
fCaSR    DSLNLDEFCNCSEHIPSTIAVVGATGSGISTAVANLLGLFYIPQVSYASSSRLLSNKNQF
         ************************************************************ cCaSR    KSFLRTIPNDEHQATAMADIIEYFRWNWVGTIAADDDYGRPGIEKFREEAEERDICIDFS
fCaSR    KSFLRTIPNDEHQATAMADIIEYFRWNWVGTIAADDDYGRPGIEKFREEAEERDICIDFS
         ************************************************************ cCaSR    ELISQYSDEEEIQQVVEVIQNSTAKVIVVFSSGPDLEPLIKEIVRRNITGRIWLASEAWA
fCaSR    ELISQYSDEEEIQQVVEVIQNSTAKVIVVFSSGPDLEPLIKEIVRRNITGRIWLASEAWA
         ************************************************************ cCaSR    SSSLIAMPEYFHVVGGTIGFALKAGQIPGFREFLQKVHPRKSVHNGFAKEFWEETFNCHL
fCaSR    SSSLIAMPEYFHVVGGTIGFALKAGQIPGFREFLQKVHPRKSVHNGFAKEFWEETFNCHL
         ************************************************************ cCaSR    QEGAKGPLSMDTFLRGHEEGGGRISNSSTAFRPLCTGDENISSVETPYMDYTHLRISYNV
fCaSR    QEGAKGPLALDTFLRGHEEGGGRISNSSTALRPLCTGDENISSVETPYMDYTHLRISYNV
         ******:.***************.**************************** cCaSR    YLAVYSIAHALQDIYTCLPGRGLFTNGSCADIKKVEAWQVLKHLRHLNFTNNMGEQVTFD
fCaSR    YLAVYSIAHALQDIYTCLPGRGLFTNGSCADIKKVEAWQVLKHLRHLNFTNNMGEQVTFD
         ************************************************************ cCaSR    ECGDLMGNYSIINWHLSPEDGSIVFKEVGYYNVYAKKGERLFINEEKILWSGFSREMPFS
fCaSR    ECGDLVGNYSIINWHLSPEDGSIVFKEVGYYNVYAKKGERLFINEEKILWSGFSREVPFS
         ***:**********************************************.* cCaSR    NCSRDCLAGTRKGIIEGEPTCCFECVECPDGEYSDETDASACDKCPDDFWSNENHTSCIA
fCaSR    NCSRDCLAGTRKGIIEGEPTCCFECVECPDGEYSDETDASACDKCPDDFWSNENHTSCIA
         ************************************************************ cCaSR    KEIEFLSWTEPFGIALTLFAVLGIFLTAFVLGVFIKFRNTPIVRATNRELSYLLLFSLLC
fCaSR    KEIEFLSWTEPFGIALTLFAVLGIFLTAFVLGVFLKFRNTPIVRATNRELSYLLLFSLLC
         *******************************:************************ cCaSR    CFSSSLFFIGEPQDWTCRLRQPAFGISFVLCISCILVKTNRVLLVFEAKIPTSFHRKWWG
fCaSR    CFSSSLFFIGEPQDWTCRLRQPAFGISFVLCISCILVKTNRVLLVFEAKIPTSFHRKWWG
         ************************************************************ cCaSR    LNLQFLLVFLCTFMQIVICVIWLYTAPPSSYRNHELEDEIIFITCHEGSLMALGFLIGYT
fCaSR    LNLQFLLVFLCTFMQIVICVIWLYTAPPSSYRNHELEDEIIFITCHEGSLMALGFLIGYT
         ************************************************************ cCaSR    CLLAAICFFAFKSRKLPENFNEAKFITFSMLIFFIVWISFIPAYASTYGKFVSAVEVIA
fCaSR    CLLAAICFFAFKSRKLPENFNEAKFITFSMLIFFIVWISFIPAYASTYGKFVSAVEVIA
         ************************************************************ cCaSR    ILAASFGLLACIFFNKVYIILFKPSRNTIEEVRCSTAAHAFKVAARATLRRSNVSRKRSG
fCaSR    ILAASFGLLACIFFNKVYIILFKPSRNTIEEVRCSTAAHAFKVAARATLRRSNVSRKRSS
         ***********************************************************.

cCaSR    SLGGSTGSTPSSSISSKSNSEDPFPQPERQKQQQPLALTQREQQPPQ--PL----TLPPQ
fCaSR    SLGGSTGSTPSSSISSKSNSEDPFPQPERQKQQQPLALTQQEQQPQPQQPSSLQQQPQPQ
         ****************************************.****  ****    *  **
```

FIG. 9 CONTINUED

```
cCaSR      PQPRCKQKVIFGSGTVTFSLSFDEPQKSAAAPRNSTLQHSLEAQRSPEPPARPQALLPPQ
fCaSR      PQPRCKQKVIFGSGTVTFSLSFDEPQKSAMAHRNSMHQNSLEAQKSNETLTRHQALLPLQ
           *************************** *  ***   *.****:*  *   :* ***** * cCaSR      GGDTDAELPAQEPGLQGPGGADRRPEMRDPEELSPALVVSSSQSFVISGGGSTVTENILH
fCaSR      CGETDSELSAQERGLQGPVDGDFRPEMEDPEEMSPALVVSSSQSFVISGGGSTVTENILH
           *:: * ***  .*  **.:************************ cCaSR      S*
fCaSR      S*
           **
```

Sequence alignments of the CaSR amino acid sequences of feline, canine and human

```
            1         10        20        30        40        50        60        70        80        90       100
cCaSR       MAFHSCSLILLAITWCSLILLAITWCTSAYGPDQRAQKGDIILGGLFPIHFGVAAKQDDLKSRPESVECIRYNFRGFRWLQAMIFAIEEINSSPALLPNMTLGYRIFDT
fCaSR       MAFYSCCLILLAITWCTSAYGPDQRAQKKGDIILGGLFPIHFGVAAKQDDLKSRPESVECIRYNFRGFRWLQAMIFAIEEINSSPVLLPNMTLGYRIFDT
hCaSR       MAFYSCCWLLALTWHTSAYGPDQRAQKKGDIILGGLFPIHFGVAAKQDDLKSRPESVECIRYNFRGFRWLQAMIFAIEEINSSPALLPNLTLGYRIFDT 101       110       120       130       140       150       160       170       180       190       200
cCaSR       CNTVSKALEATLSFVAQNKIDSLNLDEFCNCSEHIPSTIAVVGATGSGISTAVANLLGLFYIPQVSYASSSRLLSNKNQFKSFLRTIPNDEHQATAMADI
fCaSR       CNTVSKALEAILSFVAQNKIDSLNLDEFCNCSEHIPSTIAVVGATGSGISTAVANLLGLFYIPQVSYASSSRLLSNKNQFKSFLRTIPNDEHQATAMADI
hCaSR       CNTVSKALEAILSFVAQNKIDSLNLDEFCNCSEHIPSTIAVVGATGSGVSTAVANLLGLFYIPQVSYASSSRLLSNKNQFKSFLRTIPNDEHQATAMADI 201       210       220       230       240       250       260       270       280       290       300
cCaSR       IEYFRWNWVGTIAADDDYGRPGIEKFREEAEERDICIDFSELISQYSDEEEIQQVVEVIQNSTAKVIVFSSGPDLEPLIKEIVRRNITGRIWLASEAWA
fCaSR       IEYFRWNWVGTIAADDDYGRPGIEKFREEAEERDICIDFSELISQYSDEEEIQQVVEVIQNSTAKVIVFSSGPDLEPLIKEIVRRNITGRIWLASEAWA
hCaSR       IEYFRWNWVGTIAADDDYGRPGIEKFREEAEERDICIDFSELISQYSDEEEIQHVVEVIQNSTAKVIVFSSGPDLEPLIKEIVRRNITGKIWLASEAWA 301       310       320       330       340       350       360       370       380       390       400
cCaSR       SSSLIAMPEYFHVVGGTIGFALKAGQIPGFREFLQKVHPRKSVHNGFAKEFWEETFNCHLQEGAKGPLSMDTFLRGHEEGGRISNSSTAFRPLCTGDEN
fCaSR       SSSLIAMPEYFHVVGGTIGFALKAGQIPGFREFLQKVHPRKSVHNGFAKEFWEETFNCHLQEGAKGPLALDTFLRGHEEGGRISNSSTALRPLCTGDEN
hCaSR       SSSLIAMPQYFHVVGGTIGFALKAGQIPGFREFLKVHPRKSVHNGFAKEFWEETFNCHLQEGAKGPLPVDTFLRGHEESGDRFSNSSTAFRPLCTGDEN 401       410       420       430       440       450       460       470       480       490       500
cCaSR       ISSVETPYMDYTHLRISYNVYLAVYSIAHALQDIYTCLPGRGLFTNGSCADIKKVEAWQVLKHLRHLNFTINNMGEQVTFDECGDLMGNYSTINWHLSPED
fCaSR       ISSVETPYMDTHLRISYNVYLAVYSIAHALQDIYTCLPGRGLFTNGSCADIKKVEAWQVLKHLRHLNFTINNMGEQVTFDECGDLVGNYSTINWHLSPED
hCaSR       ISSVETPYIDYTHLRISYNVYLAVYSIAHALQDIYTCLPGRGLFTNGSCADIKKVEAWQVLKHLRHLNFTINNMGEQVTFDECGDLVGNYSTINWHLSPED 501       510       520       530       540       550       560       570       580       590       600
cCaSR       GSIVFKEVGYYNVYAKKGERLFINEEKILWSGFSREMPFSNCSRDCLAGTRKGIIEGEPTCCFECVECPDGEYSDEIDASACDKCPDDFWSNENHTSCIA
fCaSR       GSIVFKEVGYYNVYAKKGERLFINEEKILWSGFSREVPFSNCSRDCLAGTRKGIIEGEPTCCFECVECPDGEYSDEIDASACDKCPDDFWSNEHTSCIA
hCaSR       GSIVFKEVGYYNVYAKKGERLFINEEKILWSGFSREVPFSNCSRDCLAGTRKGIIEGEPTCCFECVECPDGEYSDEIDASACNKCPDDFWSNENHTSCIA
```

FIG. 10

```
cSaSR  KEIEFLSWTEPFGIALTLFAVLGIFLTAFVLGVFIKFRNTPIVKATNRELSYLLLFSLLCCFSSSLFFIGEPQDWTCRLRQPAFGISFVLCISCILVKTIN
fCaSR  KEIEFLSWTEPFGIALTLFAVLGIFLTAFVLGVFIKFRNTPIVKATNRELSYLLLFSLLCCFSSSLFFIGEPQDWTCRLRQPAFGISFVLCISCILVKTIN
hCaSR  KEIEFLSWTEPFGIALTLFAVLGIFLTAFVLGVFIKFRNTPIVKATNRELSYLLLFSLLCCFSSSLFFIGEPQDWTCRLRQPAFGISFVLCISCILVKTIN cSaSR  RVLLVFEAKIPTSFHRKWWGLNLQFLLVFLCTFMQIVICVIWLYTAPPSSYRNHELEDEIIFITCHEGSLMALGFLIGYTCLLAAICFFAFKSRKLPEN
fCaSR  RVLLVFEAKIPTSFHRKWWGLNLQFLLVFLCTFMQIVICVIWLYTAPPSSYRNHELEDEIIFITCHEGSLMALGFLIGYTCLLAAICFFAFKSRKLPEN
hCaSR  RVLLVFEAKIPTSFHRKWWGLNLQFLLVFLCTFMQIVICVIWLYTAPPSSYRNQELEDEIIFITCHEGSLMALGFLIGYTCLLAAICFFAFKSRKLPEN cSaSR  FNEAKFITFSMLIFFIVWISFIPAYASTYGKFVSAVEVIAILAASFGLLACIFFNKVYIILFKPSRNTIEEVRCSTAAHAFKVAARATLRRSNVSRKRSG
fCaSR  FNEAKFITFSMLIFFIVWISFIPAYASTYGKFVSAVEVIAILAASFGLLACIFFNKVYIILFKPSRNTIEEVRCSTAAHAFKVAARATLRRSNVSRKRSS
hCaSR  FNEAKFITFSMLIFFIVWISFIPAYASTYGKFVSAVEVIAILAASFGLLACIFFNKIYIILFKPSRNTIEEVRCSTAAHAFKVAARATLRRSNVSRKRSS cSaSR  SLGGSTGSTPSSSISSKSNSEDPFPQPERQKQQQPLALTQREQQP---PQ-PLITP----PQPQPRCKQKVIFGSGTVFSLSTDEPQKSAAAPRNSTLQHS
fCaSR  SLGGSTGSTPSSSISSKSNSEDPFPQPERQKQQQPLALTQQEQQQPQPQPQPQPQPQPSSQQQPQPQPQPRCKQKVIFGSGTVFSLSTDEPQKSAMAHRNSMHQNS
hCaSR  SLGGSTGSTPSSSISSKSNSEDPFTPQPERQKQQQPLALTQEEQQQ---Q-PLTLPQQQRSQQPRCKQKVIFGSGTVFSLSTDEPQKNAMAHRNSTHQNS cSaSR  LEAQRSPEPPARPQALLPPQGGDIDAELPAQEPGLQGPGGADRRPEELSPALVWSSQSTVIENILHS
fCaSR  LEAQKSNETLTRHQALLPLQCGETDSELSAQERGLQGPVDGDFRPEMEDPEEMSPALVWSSQSTVTENILHS
hCaSR  LEAQKSSDTLTRHEPLLPLLPLQCGEIDLDLTVQETGLQGPVGGDQRPEVEDPEELSPALVWSSQSQSFVISGGSTVTENVVNS
```

FIG. 10 continued

Sequence alignments of the VFT domains of feline, canine and human

| | 1 | 10 | 20 | 30 | 40 | 50 | 60 | 70 | 80 | 90 | 100 |
|---|---|---|---|---|---|---|---|---|---|---|---|
| cCaSR | MAFHSCSLILLLAITWCTSAYCPDQRAQKKGDIILGGLFPIHFGVAAKDQDLKSRPESVECIRYNFRGFRWLQAMIFAIEEINSSPALLPNMTLGYRIFDT |
| fCaSR | MAFYSCCLILLAITWCTSAYGPDQRAQKKGDIILGGLFPIHFGVAAKDQDLKSRPESVECIRYNFRGFRWLQAMIFAIEEINSSPVLLPNMTLGYRIFDT |
| hCaSR | MAFYSCCWVLLALTWHTSAYGPDQRAQKKGDIILGGLFPIHFGVAAKDQDLKSRPESVECIRYNFRGFRWLQAMIFAIEEINSSPALLPNLTLGYRIFDT |

| | 110 | 120 | 130 | 140 | 150 | 160 | 170 | 180 | 190 | 200 |
|---|---|---|---|---|---|---|---|---|---|---|
| cCaSR | CNTVSKALEATLSFVAQNKIDSLNLDEFCNCSEHIPSTIAVVGATGSGISTAVANLLGLFYIPQVSYASSSRLLSNKNQFKSFLRTIPNDEHQATAMADI |
| fCaSR | CNTVSKALEATLSFVAQNKIDSLNLDEFCNCSEHIPSTIAVGATGSGISTAVANLLGLFYIPQVSYASSSRLLSNKNQFKSFLRTIPNDEHQATAMADI |
| hCaSR | CNTVSKALEATLSFVAQNKIDSLNLDEFCNCSEHIPSTIAVVGATGSGVSTAVANLLGLFYIPQVSYASSSRLLSNKNQFKSFLRTIPNDEHQATAMADI |

| | 210 | 220 | 230 | 240 | 250 | 260 | 270 | 280 | 290 | 300 |
|---|---|---|---|---|---|---|---|---|---|---|
| cCaSR | IEYFRWNWVGTIAADDDYGRPGIEKFREEAEERDICIDFSELISQYSDEEEIQQVVEVIQNSTAKVIVVFSSGPDLEPLIKEIVRRNITGRIWLASEAWA |
| fCaSR | IEYFRMNWVGTIAADDDYGRPGIEKFREEAEERDICIDFSELISQYSDEEEIQQVVEVIQNSTAKVIVVFSSGPDLEPLIKEIVRRNITGRIWLASEAWA |
| hCaSR | IEYFRWNWVGTIAADDDYGRPGIEKFREEAEERDICIDFSELISQYSDEEEIQHVVEVIQNSTAKVIVVFSSGPDLEPLIKEIVRRNITGKIWLASEAWA |

| | 310 | 320 | 330 | 340 | 350 | 360 | 370 | 380 | 390 | 400 |
|---|---|---|---|---|---|---|---|---|---|---|
| cCaSR | SSSLIAMPEYFHVGGTIGFALKAGQIPGFREFLQKVHPRKSVHNGFAKEFWEETFNCHLQEGAKGPLSMDTFLRGHEEGGRISNSSTAFRPLCTGDEN |
| fCaSR | SSSLIAMPEYFHVGGTIGFALKAGQIPGFREFLQKVHPRKSVHNGFAKEFWEETFNCHLQEGAKGPLALDTFLRGHEEGGRISNSSTALRPLCTGDEN |
| hCaSR | SSSLIAMPEYFHVGGTIGFALKAGQIPGFREFLKKVHPRKSVHNGFAKEFWEETFNCHLQEGAKGPLPVDTFLRGHEESDRFSNSSTAFRPLCTGDEN |

| | 410 | 420 | 430 | 440 | 450 | 460 | 470 | 480 | 490 | 500 |
|---|---|---|---|---|---|---|---|---|---|---|
| cCaSR | ISSVETPYMDYTHLRISYNVYLAVYSIAHALQDIYTCLPGRGLFTNGSCADIKKVEAWQVLKHLRHLNFTNNMGEQVTFDECGDLMGNYSIINWHLSPED |
| fCaSR | ISSVETPYMDYTHLRISYNVYLAVYSIAHALQDIYTCLPGRGLFTNGSCADIKKVEAWQVLKHLRHLNFTNNMGEQVTFDECGDLVGNYSIINWHLSPED |
| hCaSR | ISSVETPYIDYTHLRISYNVYLAVYSIAHALQDIYTCLPGRGLFTNGSCADIKKVEAWQVLKHLRHLNFTNNMGEQVTFDECGDLVGNYSIINWHLSPED |

| | 510 | 520 | 530 | 540 | 550 | 560 | 570 | 580 | 590 | 600 |
|---|---|---|---|---|---|---|---|---|---|---|
| cCaSR | GSIVFKEVGYYNVYAKKGERLFINEEKI |
| fCaSR | GSIVFKEVGYYNVYAKKGERLFINEEKI |
| hCaSR | GSIVFKEVGYYNVYAKKGERLFINEEKI |

FIG. 11A

Sequence alignment of the 7TM domains of feline, canine and human

| | 610 | 620 | 630 | 640 | 650 | 660 | 670 | 680 | 690 | 700 |
|---|---|---|---|---|---|---|---|---|---|---|
| cSaSR | KEIEFLSWTEPFGIALTLFAVLGIFLTAFVLGVFIKFRNTPIVKATNRELSYLLFSLLCCFSSSLFFIGEPQDWTCRLRQPAFGISFVLCISCILVKTIN |
| fCaSR | KEIEFLSWTEPFGIALTLFAVLGIFLTAFVLGVFIKFRNTPIVKATNRELSYLLFSLLCCFSSSLFFIGEPQDWTCRLRQPAFGISFVLCISCILVKTIN |
| hCaSR | KEIEFLSWTEPFGIALTLFAVLGIFLTAFVLGVFIKFRNTPIVKAINRELSYLLFSLLCCFSSSLFFIGEPQDWTCRLRQPAFGISFVLCISCILVKTIN |

| | 710 | 720 | 730 | 740 | 750 | 760 | 770 | 780 | 790 | 800 |
|---|---|---|---|---|---|---|---|---|---|---|
| cSaSR | RVLLVFEAKIPTSFHRKWWGLNLQFLLVFLCTFMQIVICVIWLYTAPPSSYRNHELEDEIIFITCHEGSLMALGFLIGYTCLLAAICFFAFKSRKLPEN |
| fCaSR | RVLLVFEAKIPTSFHRKWWGLNLQFLLVFLCTFMQIVICVIWLYTAPPSSYRNHELEDEIIFITCHEGSLMALGFLIGYTCLLAAICFFAFKSRKLPEN |
| hCaSR | RVLLVFEAKIPTSFHRKWWGLNLQFLLVFLCTFMQIVICVIWLYTAPPSSYRNQELEDEIIFITCHEGSLMALGFLIGYTCLLAAICFFAFKSRKLPEN |

| | 810 | 820 | 830 | 840 | 850 | 860 | 870 | 880 | 890 | 900 |
|---|---|---|---|---|---|---|---|---|---|---|
| cSaSR | FNEAKFITFSMLIFFIVWISFIPAYASTYGKFVSAEVIAILAASFGLLACIFFNKVYIILFKPSRNTIEEVRCSTAAHAFKVAARATLRRSNVSRKRSG |
| fCaSR | FNEAKFITFSMLIFFIVWISFIPAYASTYGKFVSAEVIAILAASFGLLACIFFNKVYIILFKPSRNTIEEVRCSTAAHAFKVAARATLRRSNVSRKRSS |
| hCaSR | FNEAKFITFSMLIFFIVWISFIPAYASTYGKFVSAEVIAILAASFGLLACIFFNKIYIILFKPSRNTIEEVRCSTAAHAFKVAARATLRRSNVSRKRSS |

| | 910 | 920 | 930 | 940 | 950 | 960 | 970 | 980 | 990 | 1,000 |
|---|---|---|---|---|---|---|---|---|---|---|
| cSaSR | SLGGSTGSTPSSSISSKSNSEDPFPQPERQKQQQPLALTQREQQP-PQ-PLTLP---PQPQPRCKQKVIFGSGTVIFSLSFDEPQKSAAAPRNSTLQHS |
| fCaSR | SLGGSTGSTPSSSISSKSNSEDPFPQPERQKQQQPLALTQEEQQPLALTQQEQQQPSSLQQQPQPQPQPQQRSQQPRCKQKVIFGSGTVIFSLSFDEPQKSAMAHRNSMHQNS |
| hCaSR | SLGGSTGSTPSSSISSKSNSEDPFPQPERQKQQQPLALTQQEQQQ---Q-PLTLPQQQPQQRSQQQPQPQPRCKQKVIFGSGTVIFSLSFDEPQKNAMAHRNSTHQNS |

| | 1,010 | 1,020 | 1,030 | 1,040 | 1,050 | 1,060 | 1,070 | 1,080 | 1,090 | 1,100 |
|---|---|---|---|---|---|---|---|---|---|---|
| cSaSR | LEAQRSPEPPARPQALLPPQGGDIDAELPAQEPGLQGPGGADRRPEMRDPEELSPALVWSSSQSFVISGGSTVENILHS |
| fCaSR | LEAQKSNETLTRHQALLPLQCGETDSELSAQERGLQGPVDGDFRPEMEDPEELSPALVWSSSQSFVISGGSTVENILHS |
| hCaSR | LEAQKSSDTLTRHEPLLPLQCGETDLTVQETGLQGPVGGDQRPEVEDPEELSPALVWSSSQSFVISGGSTVENVVNS |

FIG. 12A

Docking of glutathione in CaSR

Docking of calindol in CaSR

Construct information

Base vector           pcDNA3.1                (5428 bps) Amp$^R$

Final clone name      pcDNA3.1_fCASR          (8669 bps) Amp$^R$

Final clone no        K4

Electronic Map

Construct information

Base vector         pcDNA5TO              (5667bps) Hygro$^R$
Final clone name    pcDNA5 TO_fCASR       (8908bps) Hygro$^R$
Final clone no      K14

Electronic map

FIG. 22

*5'NotI-3'ApaI* DNA fragment containing CDS of fCASR ( 3260 cds) (SEQ ID NO:7)

Gcggccgcgccacc<u>atg</u>gcattttatagctgctgtttgatcctcttggcaattacctggtgcacttctgcctatgggcctgaccaacgagctca
gaagaaaggggacattatcctcgggggggctctttcctattcattttggagtagcagccaaagatcaagatctaaagtcaaggccagagtctgt
ggaatgtatcaggtataatttccgtgggtttcgctggttacaagcaatgatatttgccatcgaggaaataaacagcagcccagtccttcttccca
acatgacactgggatacaggatatttgacacttgcaacactgtttctaaagccttggaggccactctgagttttgtggcacaaaataaaattgat
tctctgaacctcgacgagttctgcaactgctcagagcatatcccctctactatcgctgtggtgggagcaactggttcgggcatctccacagcg
gtggcaaacctgctgggcctcttctatattcccaggtcagctatgcctcctccagcagactcctcagcaacaaaaatcagttcaagtcctttct
ccgtaccatccccaatgatgaacaccaggccactgccatggcagacattatcgagtatttccgctggaactgggtgggcacaattgctgctg
atgatgactacggccggccagggattgagaagtttcgagaggaagctgaggagagggacatctgcatcgacttcagtgaactcatctccca
gtattctgatgaagaagagatccagcaagtggtggaggtgatccagaattccacagccaaagtcattgttgttttctctagtggcccagacctt
gaacccttatcaaggagattgtccggcgtaatatcacagggaggatctggctggccagcgaggcctgggccagctcttccttgattgccat
gcccgagtacttccatgtggttggaggcaccattggattcgctctgaaggctggacagatcccaggttccgggaattcctgcagaaagtcc
atcccagaaagtctgtccacaatggttttgccaaggagttttgggaagaaaccttaactgccacctccaagaaggtgctaaaggacctttag
cactggacactttcctgagaggtcatgaagaaggtggtggcaggataagcaatagctccactgccttgcgacctctctgtacaggggacga
gaacatcagcagcgtggagaccccttacatggattatacacatttacggatatcctacaatgtctacttagcggtctattccattgctcatgccct
gcaagatatatatacatgcttacctggaagagggctcttcaccaatggttcctgcgcagatatcaagaaggttgaggcttggcaggtcctgaa
gcacctacggcacctaaactttaccaacaatatgggggagcaggtgactttcgatgaatgtggggacctggtggggaactattccatcatca
actggcacctctctccagaggatggctccatagtgtttaaggaagtcggatattacaacgtctatgccaagaaaggagaaaggctcttcatca
atgaggagaaaatcctgtggagtggattctccagggaggtacctttctccaactgcagtcgagactgcctggcagggacccggaaaggaa
tcattgaggggagcccacctgctgctttgagtgtgtggaatgtcctgatggggagtacagtgatgaaacagatgcaagtgcctgtgacaag
tgccccgatgacttctggtccaatgagaaccacacttcttgcattgccaaggagattgagttctgtcctggacggagcccttgggattgcac
tcactctctttgctgtgctgggcattttcctgacagccttcgtgctgggtgtcttcctcaagttccgtaacacacccattgtcaaggctaccaatc
gagagctctcctacctcctcctcttctccttgctctgctgcttctccagctccctgttcttcattggtgagcccaggactggacatgccgcctgc
gccagccagcctttggcatcagcttcgtgctctgcatatcatgcatcctagtgaaaaccaaccgtgtcctcctggtgtttgaggccaagatccc
cacgagcttccaccgcaagtggtgggggctcaacctgcagttcctgctggtcttcctctgcaccttcatgcagattgtcatctgtgtgatctgg
ctctacactgcaccaccctcaagctaccgcaaccacgagctggaggatgagatcatctttatcacatgccacgagggctcgctcatggccct
gggcttcttaattggctacacctgcctactggctgccatctgcttcttctttgccttcaagtcccggaagctgccagagaatttcaatgaagcca
agttcatcaccttcagcatgctcatcttcttcatcgtctggatctccttcatcccagcctatgccagcacctatggcaagtttgtctctgccgtgga
agtgatcgccatcctggcagccagctttggcttgctggcctgcatcttcttcaacaaggtctacatcatcctcttcaagccatcacgtaacacca
tcgaggaggtgcgctgcagcactgctgcccatgctttcaaagtagcagcccgggccacgctgcgccgcagcaacgtctctcgcaagcgg
tccagcagccttgggggctccacgggatccacaccctcttcctccatcagcagtaagagcaacagtgaagaccccttcccacagcccgag
aggcaaaagcagcagcagccactggccctgacccaacaagagcagcagccgcagccacagcagccctcgtccctacagcagcagcca
cagccacagccacagcccagatgcaagcagaaagtcattttcggcagtggcacagtcaccttctcactgagctttgatgagcctcagaaga
gtgccatggctcacaggaattctatgcaccagaactccctggaggcccagaaaagcaatgagaccctcaccagacaccaggcattactcc
cactacagtgcggggagacagactcagaactgagtgcccaggagagaggtcttcaagggcctgtagatggggacttccgaccagagatg
gaggaccctgaagagatgtccccagcgcttgtagtgtccagttcacaaagctttgtcatcagtggtggtggcagcactgtcacagaaaatat
actgcattcataa<u>gggcc</u>

METHODS FOR IDENTIFYING MODULATORS OF CALCIUM-SENSING RECEPTORS

CROSS-REFERENCE TO RELATED APPLICATION

This application is a continuation of U.S. patent application Ser. No. 15/517,409, filed on Apr. 6, 2017, which is a U.S. National Stage Patent Application under 35 U.S.C. § 371 of International Application No. PCT/US2015/055149, filed on Oct. 12, 2015, which claims priority to U.S. Provisional Application Ser. No. 62/062,717, filed on Oct. 10, 2014, the contents of each of which are incorporated in their entirety herein.

SEQUENCE LISTING

The instant application contains a Sequence Listing which has been submitted electronically in ASCII format and is hereby incorporated by reference in its entirety. Said ASCII copy, created on Jun. 4, 2019, is named 069269_0328_SL.txt and is 45,583 bytes in size.

FIELD

The presently disclosed subject matter relates to methods for identifying compounds that modulate the activity and/or expression of a calcium-sensing receptor.

BACKGROUND

Taste profiles for edible compositions include basic tastes such as sweet, salt, bitter, sour, umami and kokumi. Taste profiles have also been described as including free fatty acid tastes. Chemical compounds that elicit these tastes are often referred to as tastants. Without being bound by theory, it is hypothesized that tastants are sensed by taste receptors in the mouth and throat which transmit signals to the brain where the tastants and resulting taste profiles are registered. Taste receptors include the calcium-sensing receptor (CaSR), which is a G-protein coupled receptor (GPCR) that detects changes in extracellular calcium levels and a close relative to the T1R1, T1R2 and T1R3 receptors, i.e., the sweet and umami receptors. The calcium-sensing receptor has been shown to enhance sweet, salty and umami tastes, and function as a receptor for kokumi taste.

Pet food manufacturers have a long-standing desire to provide pet food products that have high nutritional value. In addition, and with particular regard to cat and dog foods, pet food manufacturers desire a high degree of palatability so that pets can receive the full nutritional benefit from their food. Domestic animals, especially cats, are notoriously fickle in their food preferences, and often refuse to eat a pet food product that it has accepted over time or refuse to eat any more than a minimal amount of a pet food product. This phenomenon may be, in part, due to the subtle differences in the sensory profiles of the raw material, which can be perceived by the domestic animals because of their gustatory and olfactory systems. As a result, pet owners frequently change types and brands of pet food in order to maintain their pets in a healthy and contented condition.

While there have been recent advances in taste and flavor technologies, there remains a need for compounds that can enhance or modify the palatability of pet food products by enhancing or modifying the taste, texture and/or flavor profiles of the pet food product. The enhancement or modification can be to increase the intensity of a desirable attribute, to replace a desirable attribute not present or somehow lost in the pet food product, or to decrease the intensity of an undesirable attribute. In particular, it is desirable to increase the intensity of a desirable tastant in a pet food product.

Therefore, there remains a need in the art for methods to identify compounds that enhance the palatability and/or modulate the kokumi taste of pet food products and for flavor compositions comprising these compounds.

SUMMARY OF THE INVENTION

The presently disclosed subject matter provides methods for identifying compounds that enhance, increase and/or modulate the activity of a calcium-sensing receptor. Once identified, such compounds can be comprised in a flavor composition that can be added to a variety of pet food products to increase the palatability of the products. For example, in certain embodiments of the present disclosure, such a flavor composition is combined with a pet food product in an amount effective to increase the kokumi taste and/or palatability of the pet food product.

In certain embodiments, a method for identifying compounds that enhance, increase and/or modulate the activity and/or expression of a calcium-sensing receptor comprises expressing a calcium-sensing receptor having a nucleotide sequence set forth in SEQ ID NO: 1, 2, 3 or 7, or a fragment or variant thereof, in a cell. The method can further comprise contacting the cell expressing the calcium-sensing receptor with a test compound and determining the activity and/or expression of the calcium-sensing receptor in the presence of the compound as compared to the activity and/or expression of the receptor in the absence of the compound.

In certain embodiments, a method for identifying compounds that enhance, increase and/or modulate the activity of a calcium-sensing receptor comprises expressing a calcium-sensing receptor having an amino acid sequence set forth in SEQ ID NO: 4, 5 or 6, or a fragment or variant thereof, in a cell. The method can further comprise contacting the cell expressing the calcium-sensing receptor with a test compound and determining the activity and/or expression of the calcium-sensing receptor in the presence of the compound as compared to the activity and/or expression of the receptor in the absence of the compound.

In certain embodiments, the present disclosure provides a method for identifying a composition that modulates the activity of a calcium-sensing receptor (CaSR) comprising (a) contacting a test agent with a CaSR, (b) determining the activity of the CaSR, and (c) selecting as the composition, a test agent that increases the activity of the CaSR.

In certain embodiments, the present disclosure provides a method for identifying a composition that modulates the activity of a calcium-sensing receptor (CaSR) comprising (a) contacting a test agent with a CaSR, (b) detecting an interaction between the test agent and one or more amino acids in a Venus Flytrap domain (VFT) or 7 transmembrane domain (7TM) of the CaSR, and (c) selecting as the composition, a test agent that interacts with one or more of the amino acids.

In certain embodiments, the present disclosure provides a method for identifying a composition that modulates the activity of a calcium-sensing receptor (CaSR) comprising (a) contacting a CaSR agonist with a CaSR, (b) determining the activity of the CaSR, (c) contacting a test agent with the CaSR, (d) determining the activity of the CaSR, and (e)

selecting the test agent as the composition when the activity of (d) is greater than the activity of (b).

The foregoing has outlined rather broadly the features and technical advantages of the present application in order that the detailed description that follows may be better understood. Additional features and advantages of the application will be described hereinafter which form the subject of the claims of the application. It should be appreciated by those skilled in the art that the conception and specific embodiment disclosed may be readily utilized as a basis for modifying or designing other structures for carrying out the same purposes of the present application. It should also be realized by those skilled in the art that such equivalent constructions do not depart from the spirit and scope of the application as set forth in the appended claims. The novel features which are believed to be characteristic of the application, both as to its organization and method of operation, together with further objects and advantages will be better understood from the following description.

BRIEF DESCRIPTION OF THE DRAWINGS

FIG. 1 shows a feline CaSR nucleotide sequence (SEQ ID NO: 1).

FIG. 2 shows a canine CaSR nucleotide sequence (SEQ ID NO: 2).

FIG. 3 shows a human CaSR nucleotide sequence (SEQ ID NO: 3).

FIG. 4 shows a feline CaSR amino acid sequence (SEQ ID NO: 4).

FIG. 5 shows a canine CaSR amino acid sequence (SEQ ID NO: 5).

FIG. 6 shows a human CaSR amino acid sequence (SEQ ID NO: 6).

FIG. 7 shows the sequence alignment of a feline CaSR and a human CaSR amino acid sequence.

FIG. 8 shows the sequence alignment of a canine CaSR and a human CaSR amino acid sequence.

FIG. 9 shows the sequence alignment of a feline CaSR and a canine CaSR amino acid sequence.

FIG. 10 shows the sequence alignment of the amino acid sequences of the feline, canine and human CaSRs.

FIGS. 11A-11B show (A) the sequence alignment of the amino acid sequences of the feline, canine and human CaSR VFT domains; and (B) 3D depiction of major structural differences within VFT domains.

FIGS. 12A-12B show (A) the sequence alignment of the amino acid sequences of the feline, canine and human CaSR 7TM domains; and (B) 3D depiction of major structural differences within 7TM domains.

FIG. 22 shows a feline CaSR nucleotide sequence with Kozak sequence, and nucleotide substitutions Y987T, M1066C, R1269G and S3131G (SEQ ID NO: 7).

DETAILED DESCRIPTION

Figure 11B:
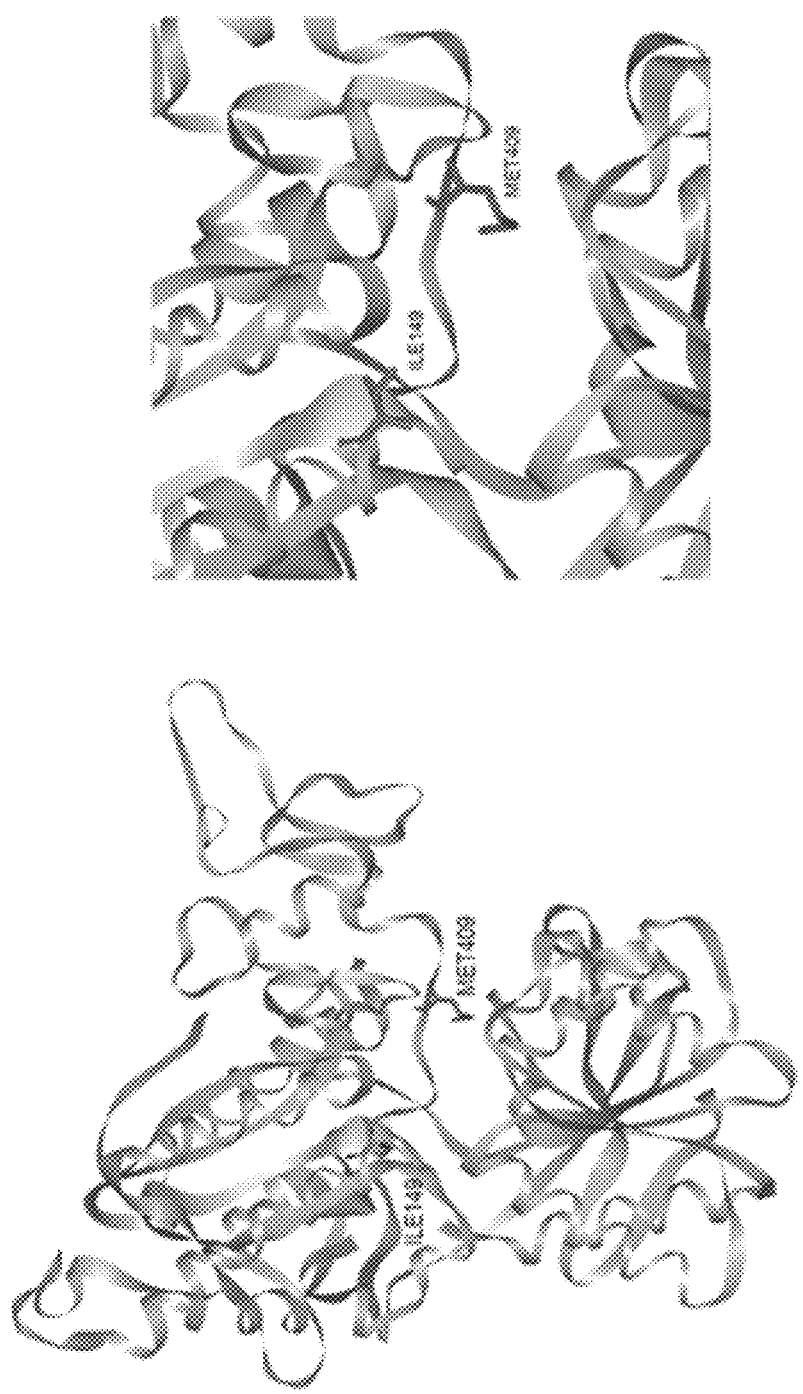

The presently disclosed subject matter relates to methods for identifying compounds that modulate the activity and/or expression of calcium-sensing receptors, wherein said compounds can be included in a flavor composition that can be used to increase the palatability and/or enhance or modify the taste of various pet food products such as a nutritionally-complete pet food or pet treats.

1. Definitions

The terms used in this specification generally have their ordinary meanings in the art, within the context of this invention and in the specific context where each term is used. Certain terms are discussed below, or elsewhere in the specification, to provide additional guidance to the practitioner in describing the methods and compositions of the invention and how to make and use them.

As used herein, the use of the word "a" or "an" when used in conjunction with the term "comprising" in the claims and/or the specification may mean "one," but it is also consistent with the meaning of "one or more," "at least one," and "one or more than one." Still further, the terms "having," "including," "containing" and "comprising" are interchangeable and one of skill in the art is cognizant that these terms are open ended terms.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

As used herein, "taste" refers to a sensation caused by activation of receptor cells in a subject's taste buds. In certain embodiments, taste can be selected from the group consisting of sweet, sour, salt, bitter, kokumi and umami. In certain embodiments, "taste" can include free fatty acid taste. See, e.g., Cartoni et al., J. of Neuroscience, 30(25): 8376-8382 (2010), the contents of which are incorporated herein by reference. In certain embodiments, a taste is elicited in a subject by a "tastant." In certain embodiments, a tastant can be a synthetic tastant. In certain embodiments, the tastant is prepared from a natural source.

As used herein, "taste profile" refers to a combination of tastes, such as, for example, one or more of a sweet, sour, salt, bitter, umami, kokumi and free fatty acid taste. In certain embodiments, a taste profile is produced by one or more tastant that is present in a composition at the same or different concentrations. In certain embodiments, a taste profile refers to the intensity of a taste or combination of tastes, for example, a sweet, sour, salt, bitter, umami, kokumi and free fatty acid taste, as detected by a subject or any assay known in the art. In certain embodiments, modifying, changing or varying the combination of tastants in a taste profile can change the sensory experience of a subject.

As used herein, "flavor" refers to one or more sensory stimuli, such as, for example, one or more of taste (gustatory), smell (olfactory), touch (tactile) and temperature (thermal) stimuli. In certain non-limiting embodiments, the sensory experience of a subject exposed to a flavor can be classified as a characteristic experience for the particular flavor. For example, a flavor can be identified by the subject as being, but not limited to, a floral, citrus, berry, nutty, caramel, chocolate, peppery, smoky, cheesy, meaty, etc., flavor. As used herein, a flavor composition can be selected from a liquid, solution, dry powder, spray, paste, suspension and any combination thereof. The flavor can be a natural composition, an artificial composition, a nature identical, or any combination thereof.

As used interchangeably herein, "aroma" and "smell" refer to an olfactory response to a stimulus. For example, and not by way of limitation, an aroma can be produced by aromatic substances that are perceived by the odor receptors of the olfactory system.

As used herein, "flavor profile" refers to a combination of sensory stimuli, for example, tastes, such as sweet, sour, bitter, salty, umami, kokumi, free fatty acid tastes, and/or olfactory, tactile and/or thermal stimuli. In certain embodiments, flavor profiles comprise one or more flavors which contribute to the sensory experience of a subject. In certain embodiments, modifying, changing or varying the combination of stimuli in a flavor profile can change the sensory experience of a subject.

As used herein, "palatability" can refer to the overall willingness of an animal to eat a certain food product. Increasing the "palatability" of a pet food product can lead to an increase in the enjoyment and acceptance of the pet food by the companion animal to ensure the animal eats a "healthy amount" of the pet food. The term "healthy amount" of a pet food as used herein refers to an amount that enables the companion animal to maintain or achieve an intake contributing to its overall general health in terms of micronutrients, macronutrients and calories, such as set out in the "Mars Petcare Essential Nutrient Standards." In certain embodiments, "palatability" can mean a relative preference of an animal for one food product over another. For example, when an animal shows a preference for one of two or more food products, the preferred food product is more "palatable," and has "enhanced palatability." In certain embodiments, the relative palatability of one food product compared to one or more other food products can be determined, for example, in side-by-side, free-choice comparisons, e.g., by relative consumption of the food products, or other appropriate measures of preference indicative of palatability. Palatability can be determined by a standard testing protocol in which the animal has equal access to both food products such as a test called "two-bowl test" or "versus test." Such preference can arise from any of the animal's senses, but can be related to, inter alia, taste, aftertaste, smell, mouth feel and/or texture.

The term "pet food" or "pet food product" means a product or composition that is intended for consumption by a companion animal, such as cats, dogs, guinea pigs, mice, rabbits, birds and horses. For example, but not by way of limitation, the companion animal can be a "domestic" cat such as *Felis domesticus*. In certain embodiments, the companion animal can be a "domestic" dog, e.g., *Canis lupus familiaris*. A "pet food" or "pet food product" can include any food, feed, snack, food supplement, liquid, beverage, treat, toy (chewable and/or consumable toys), meal substitute or meal replacement.

As used herein "nutritionally-complete" refers to pet food products that contain all known required nutrients for the intended recipient of the pet food product, in appropriate amounts and proportions based, for example, on recommendations of recognized or competent authorities in the field of companion animal nutrition. Such foods are therefore capable of serving as a sole source of dietary intake to maintain life, without the addition of supplemental nutritional sources.

As used herein "flavor composition" refers to at least one compound or biologically acceptable salt thereof that modulates, including enhancing, multiplying, potentiating, decreasing, suppressing, or inducing, the tastes, smells, flavors and/or textures of a natural or synthetic tastant, flavoring agent, taste profile, flavor profile and/or texture profile in an animal or a human. In certain embodiments, the flavor composition comprises a combination of compounds or biologically acceptable salts thereof. In certain embodiments, flavor composition includes one or more excipients.

As used herein, the terms "modulates" or "modifies" refers an increase or decrease in the amount, quality or effect of a particular activity of a receptor and/or an increase or decrease in the expression, activity or function of a receptor. "Modulators," as used herein, refer to any inhibitory or activating compounds identified using in silico, in vitro and/or in vivo assays for, e.g., agonists, antagonists and their homologs, including fragments, variants and mimetics.

"Inhibitors" or "antagonists," as used herein, refer to modulating compounds that reduce, decrease, block, prevent, delay activation, inactivate, desensitize or downregulate biological activity and/or expression of receptors or pathway of interest.

"Inducers," "activators" or "agonists," as used herein, refer to modulating compounds that increase, induce, stimulate, open, activate, facilitate, enhance activation, sensitize or upregulate a receptor or pathway of interest.

As used herein, the terms "vector" and "expression vector" refer to DNA molecules that are either linear or circular, into which another DNA sequence fragment of appropriate size can be integrated. Such DNA fragment(s) can include additional segments that provide for transcription of a gene encoded by the DNA sequence fragment. The additional segments can include and are not limited to: promoters, transcription terminators, enhancers, internal ribosome entry sites, untranslated regions, polyadenylation signals, selectable markers, origins of replication and such like. Expression vectors are often derived from plasmids, cosmids, viral vectors and yeast artificial chromosomes. Vectors are often recombinant molecules containing DNA sequences from several sources.

The term "operably linked," when applied to DNA sequences, e.g., in an expression vector, indicates that the sequences are arranged so that they function cooperatively in order to achieve their intended purposes, i.e., a promoter sequence allows for initiation of transcription that proceeds through a linked coding sequence as far as the termination signal.

The term "nucleic acid molecule" and "nucleotide sequence," as used herein, refers to a single or double stranded covalently-linked sequence of nucleotides in which the 3' and 5' ends on each nucleotide are joined by phosphodiester bonds. The nucleic acid molecule can include deoxyribonucleotide bases or ribonucleotide bases, and can be manufactured synthetically in vitro or isolated from natural sources.

The terms "polypeptide," "peptide," "amino acid sequence" and "protein," used interchangeably herein, refer to a molecule formed from the linking of at least two amino acids. The link between one amino acid residue and the next is an amide bond and is sometimes referred to as a peptide bond. A polypeptide can be obtained by a suitable method known in the art, including isolation from natural sources, expression in a recombinant expression system, chemical synthesis or enzymatic synthesis. The terms can apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid," as used herein, refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, gamma-carboxyglutamate and O-phosphoserine. Amino acid analogs and derivatives can refer to compounds that have the same basic chemical structure as a naturally occurring amino acid, i.e., a carbon that is bound to a hydrogen, a carboxyl group, an amino group and an R group, e.g., homoserine, norleucine, methionine sulfoxide and methionine methyl sulfonium. Such analogs can have modified R groups (e.g., norleucine) or modified peptide backbones, but retain the same basic chemical structure as a naturally occurring amino acid Amino acid mimetics means chemical compounds that have a structure that is different from the general chemical structure of an amino acid, but that functions in a manner similar to a naturally occurring amino acid.

The terms "isolated" or "purified," used interchangeably herein, refers to a nucleic acid, a polypeptide, or other biological moiety that is removed from components with which it is naturally associated. The term "isolated" can refer to a polypeptide that is separate and discrete from the whole organism with which the molecule is found in nature or is present in the substantial absence of other biological macromolecules of the same type. The term "isolated" with respect to a polynucleotide can refer to a nucleic acid molecule devoid, in whole or part, of sequences normally associated with it in nature; or a sequence, as it exists in nature, but having heterologous sequences in association therewith; or a molecule disassociated from the chromosome.

As used herein, the term "recombinant" can be used to describe a nucleic acid molecule and refers to a polynucleotide of genomic, RNA, DNA, cDNA, viral, semisynthetic or synthetic origin which, by virtue of its origin or manipulation is not associated with all or a portion of polynucleotide with which it is associated in nature.

The term "fusion," as used herein, refers to joining of different peptide or protein segments by genetic or chemical methods wherein the joined ends of peptide or protein segments may be directly adjacent to each other or may be separated by linker or spacer moieties such as amino acid residues or other linking groups.

2. Calcium-Sensing Receptors

The presently disclosed subject matter provides calcium-sensing receptors (CaSRs) for use in the disclosed methods. The calcium-sensing receptors of the present disclosure can include mammalian calcium-sensing receptors such as, but not limited to, felines, canines and humans.

In certain embodiments, a calcium-sensing receptor for use in the presently disclosed subject matter encompasses a feline calcium-sensing receptor having the nucleotide sequence set forth in SEQ ID NO: 1 or 7 and/or the amino acid sequence set forth in SEQ ID NO:4, including fragments thereof (e.g., functional fragments thereof) and variants thereof.

In certain embodiments, a calcium-sensing receptor for use in the presently disclosed subject matter encompasses a canine calcium-sensing receptor having the nucleotide sequence set forth in SEQ ID NO: 2 and/or the amino acid sequence set forth in SEQ ID NO:5, including fragments thereof (e.g., functional fragments thereof) and variants thereof.

In certain embodiments, a calcium-sensing receptor for use in the presently disclosed subject matter encompasses a human calcium-sensing receptor having the nucleotide sequence set forth in SEQ ID NO: 3 and/or the amino acid sequence set forth in SEQ ID NO:6, including fragments thereof (e.g., functional fragments thereof) and variants thereof.

In certain embodiments, the calcium-sensing receptor for use in the presently disclosed subject matter can include a receptor comprising a nucleotide sequence having at least 85%, at least 90%, at least 91%, at least 92%, at least 93%, at least 94%, at least 95%, at least 96%, at least 97%, at least 98% or at least 99% identity to SEQ ID NO: 1, 2, 3 or 7.

In certain embodiments, the calcium-sensing receptor for use in the presently disclosed subject matter can include a receptor comprising an amino acid sequence having at least 85%, at least 90%, at least 91%, at least 92%, at least 93%, at least 94%, at least 95%, at least 96%, at least 97%, at least 98% or at least 99% identity to SEQ ID NO: 4, 5 or 6.

The percent identity of two amino acid sequences or of two nucleotide sequences can be determined by aligning the sequences for optimal comparison purposes (e.g., gaps can be introduced in the first sequence for best alignment with the sequence) and comparing the amino acid residues or nucleotides at corresponding positions. The percent identity can be determined by the number of identical amino acid residues or nucleotides in the sequences being compared (e.g., % identity=number of identical positions/total number of positions×100).

The determination of percent identity between two sequences can be determined using a mathematical algorithm known to those of skill in the art. A non-limiting example of a mathematical algorithm for comparing two sequences is the algorithm of Karlin and Altschul (1990) Proc. Natl. Acad. Sci. USA 87:2264-2268, modified as in Karlin and Altschul (1993) Proc. Natl. Acad. Sci. USA 90:5873-5877, the disclosures of which are incorporated herein by reference in their entireties. The NBLAST and XBLAST programs of Altschul, et al. (1990) J. Mol. Biol. 215:403-410 have incorporated such an algorithm. BLAST nucleotide searches can be performed with the NBLAST program, score=100, wordlength=12, to obtain nucleotide sequences homologous to nucleotide sequences of the invention. BLAST protein searches can be performed with the XBLAST program, score=50, wordlength=3 to obtain amino acid sequences homologous to amino acid sequence of the invention. To obtain gapped alignments for comparison purposes, Gapped BLAST can be utilized as described in Altschul et al. (1997) Nucleic Acids Res. 25:3389-3402, the disclosure of which is incorporated herein by reference in its entirety. Alternatively, PSI-Blast can be used to perform an iterated search, which detects distant relationships between molecules. When utilizing BLAST, Gapped BLAST, and PSI-Blast programs, the default parameters of the respective programs (e.g., XBLAST and NBLAST) can be used. See http://www.ncbi.nlm.nih.gov. An additional non-limiting example of a mathematical algorithm utilized for the comparison of sequences is the algorithm of Myers and Miller, CABIOS (1989), the disclosure of which is incorporated herein by reference in its entirety. The ALIGN program (version 2.0), which is part of the CGC sequence alignment software package, has incorporated such an algorithm. Other non-limiting examples of algorithms for sequence analysis known in the art include ADVANCE and ADAM as described in Torellis and Robotti (1994) Comput. Appl. Biosci., 10:3-5; and FASTA described in Pearson and Lipman (1988) Proc. Natl. Acad. Sci. 85:2444-8, the disclosures of which are incorporated herein by reference in their entireties. Within FASTA, ktup is a control option that sets the sensitivity and speed of the search.

In certain embodiments, the disclosed subject matter provides for the use of an isolated or purified calcium-sensing receptor and/or variants and fragments thereof. The disclosed subject matter also encompasses the use of sequence variants. In certain embodiments, variation can occur in either or both the coding and non-coding regions of a nucleotide sequence of a calcium-sensing receptor. Variants can include a substantially homologous protein encoded by the same genetic locus in an organism, i.e., an allelic variant. Variants also encompass proteins derived from other genetic loci in an organism, e.g., feline, but having substantial homology to the calcium-sensing receptor, i.e., a homolog. Variants can also include proteins substantially homologous to the calcium-sensing receptor but derived from another organism, i.e., an ortholog. Variants also include proteins that are substantially homologous to the calcium-sensing receptor that are produced by chemical synthesis. Variants also include proteins that are substantially homologous to the calcium-sensing receptor that are produced by recombinant methods.

Orthologs, homologs and allelic variants can be identified using methods well known in the art. These variants can include a nucleotide sequence encoding a receptor that is at least about 60-65%, about 65-70%, about 70-75, about 80-85%, about 90-95%, about 95-99% or more homologous to the nucleotide sequence shown in SEQ ID NO: 1, 2, 3 or 7, or fragments thereof. Such nucleic acid molecules can readily be identified as being able to hybridize under stringent conditions, to the nucleotide sequence shown in SEQ ID NO: 1, 2, 3 or 7, or a fragment thereof. In certain embodiments, two polypeptides (or regions thereof) are substantially homologous when the amino acid sequences are at least about 60-65%, about 65-70%, about 70-75, about 80-85%, about 90-95%, about 95-99% or more homologous to the amino acid sequences shown in SEQ ID NO: 4, 5 or 6, or a fragment thereof. A substantially homologous amino acid sequence, according to the disclosed subject matter, will be encoded by a nucleic acid sequence hybridizing to the nucleic acid sequence, or portion thereof, of the nucleotide sequence shown in SEQ ID NOs: 1, 2, 3 or 7 under stringent conditions.

The calcium-sensing receptors for use in the methods of the disclosed subject matter include calcium-sensing receptors having additions, deletions or substitutions of amino acid residues (variants) which do not substantially alter the biological activity of the receptor. Those individual sites or regions of the calcium-sensing receptors which may be altered without affecting biological activity can be determined by examination of the structure of the calcium-sensing receptor extracellular domain, for example. Alternatively and/or additionally, one can empirically determine those regions of the receptor which would tolerate amino acid substitutions by alanine scanning mutagenesis (Cunningham et al., Science 244, 1081-1085 (1989), the disclosure of which is hereby incorporated by reference in its entirety). In the alanine scanning mutagenesis method, selected amino acid residues are individually substituted with a neutral amino acid (e.g., alanine) in order to determine the effects on biological activity.

It is generally recognized that conservative amino acid changes are least likely to perturb the structure and/or function of a polypeptide. Accordingly, the disclosed subject matter encompasses one or more conservative amino acid changes within a calcium-sensing receptor. Conservative amino acid changes generally involve substitution of one amino acid with another that is similar in structure and/or function (e.g., amino acids with side chains similar in size, charge and shape). Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). In certain embodiments, one or more amino acid residues within a calcium-sensing receptor can be replaced with other amino acid residues from the same side chain family and the altered protein can be tested for retained function using the functional assays described herein. Modifications can be introduced into a calcium-sensing receptor of the present disclosure by standard techniques known in the art, such as site-directed mutagenesis and PCR-mediated mutagenesis. If such substitutions result in a retention in biological activity, then more substantial changes can be introduced and/or other additions/deletions may be made and the resulting products screened. In certain embodiments, deletions or additions can be from 5-10 residues, alternatively from 2-5 amino acid residues or from 1-2 residues.

The disclosed subject matter also provides for fusion proteins that comprise a calcium-sensing receptor, or fragment thereof. In certain embodiments, the disclosed subject matter provides for fusion proteins of a calcium-sensing receptor, or functional fragments thereof, and an immunoglobulin heavy chain constant region. In certain embodiments, a fusion protein of the present disclosure can include a detectable marker, a functional group such as a carrier, a label, a stabilizing sequence or a mechanism by which calcium-sensing receptor agonist binding can be detected. Non-limiting embodiments of a label include a FLAG tag, a His tag, a MYC tag, a maltose binding protein and others known in the art. The presently disclosed subject matter also provides nucleic acids encoding such fusion proteins, vectors containing fusion protein-encoding nucleic acids and host cells comprising such nucleic acids or vectors. In certain embodiments, fusions can be made at the amino terminus (N-terminus) of a calcium-sensing receptor or at the carboxy terminus (C-terminus) of a calcium-sensing receptor.

In certain embodiments, the calcium-sensing receptors disclosed herein can contain additional amino acids at the N-terminus and/or at the C-terminus end of the sequences, e.g., when used in the methods of the disclosed subject matter. In certain embodiments, the additional amino acids can assist with immobilizing the polypeptide for screening purposes, or allow the polypeptide to be part of a fusion protein, as disclosed above, for ease of detection of biological activity.

3. Methods for Identifying CaSR Modulating Compounds

The present disclosure further provides methods for identifying compounds that modulate the activity and/or expression of a calcium-sensing receptor. For example, and not by way of limitation, the modulator can be an agonist or an antagonist. The presently disclosed subject matter provides in silico and in vitro methods for identifying compounds that modulate the activity and/or expression of a calcium-sensing receptor, disclosed above.

3.1 In silico Methods

The presently disclosed subject matter further provides in silico methods for identifying compounds that can potentially interact with a calcium-sensing receptor and/or modulate the activity and/or expression of a calcium-sensing receptor.

In certain embodiments, the method can include predicting the three-dimensional structure (3D) of a calcium-sensing receptor and screening the predicted 3D structure with putative calcium-sensing receptor modulating compounds (i.e., test compounds). The method can further include predicting whether the putative compound would interact with the binding site of the receptor by analyzing the potential interactions with the putative compound and the amino acids of the receptor. The method can further include identifying a test compound that can bind to and/or modulate the biological activity of the calcium-sensing receptor by determining whether the 3D structure of the compound fits within the binding site of the 3D structure of the receptor.

In certain embodiments, the calcium-sensing receptor for use in the disclosed method can have the amino acid sequence of SEQ ID NO: 4, 5 or 6, or a fragment or variant thereof. In certain embodiments, the calcium-sensing receptor for use in the presently disclosed subject matter can include a receptor comprising an amino acid sequence having at least 85%, at least 90%, at least 91%, at least 92%, at least 93%, at least 94%, at least 95%, at least 96%, at least 97%, at least 98% or at least 99% identity to SEQ ID NO: 4, 5 or 6, or a fragment or variant thereof. In certain embodiments, the calcium-sensing receptor for use in the disclosed method can have the nucleotide sequence of SEQ ID NO: 1, 2, 3 or 7, or a fragment or variant thereof. In certain embodiments, the calcium-sensing receptor for use in the presently disclosed subject matter can include a receptor comprising a nucleotide sequence having at least 85%, at least 90%, at least 91%, at least 92%, at least 93%, at least 94%, at least 95%, at least 96%, at least 97%, at least 98% or at least 99% identity to SEQ ID NO: 1, 2, 3 or 7, or a fragment or variant thereof.

Non-limiting examples of compounds (e.g., potential calcium-sensing receptor modulators) that can be tested using the disclosed methods include any small chemical compound, or any biological entity, such as peptides, salts, amino acids and kokumi compounds known in the art, e.g. glutathione. In certain embodiments, the test compound can be a small chemical molecule.

Figure 13A:
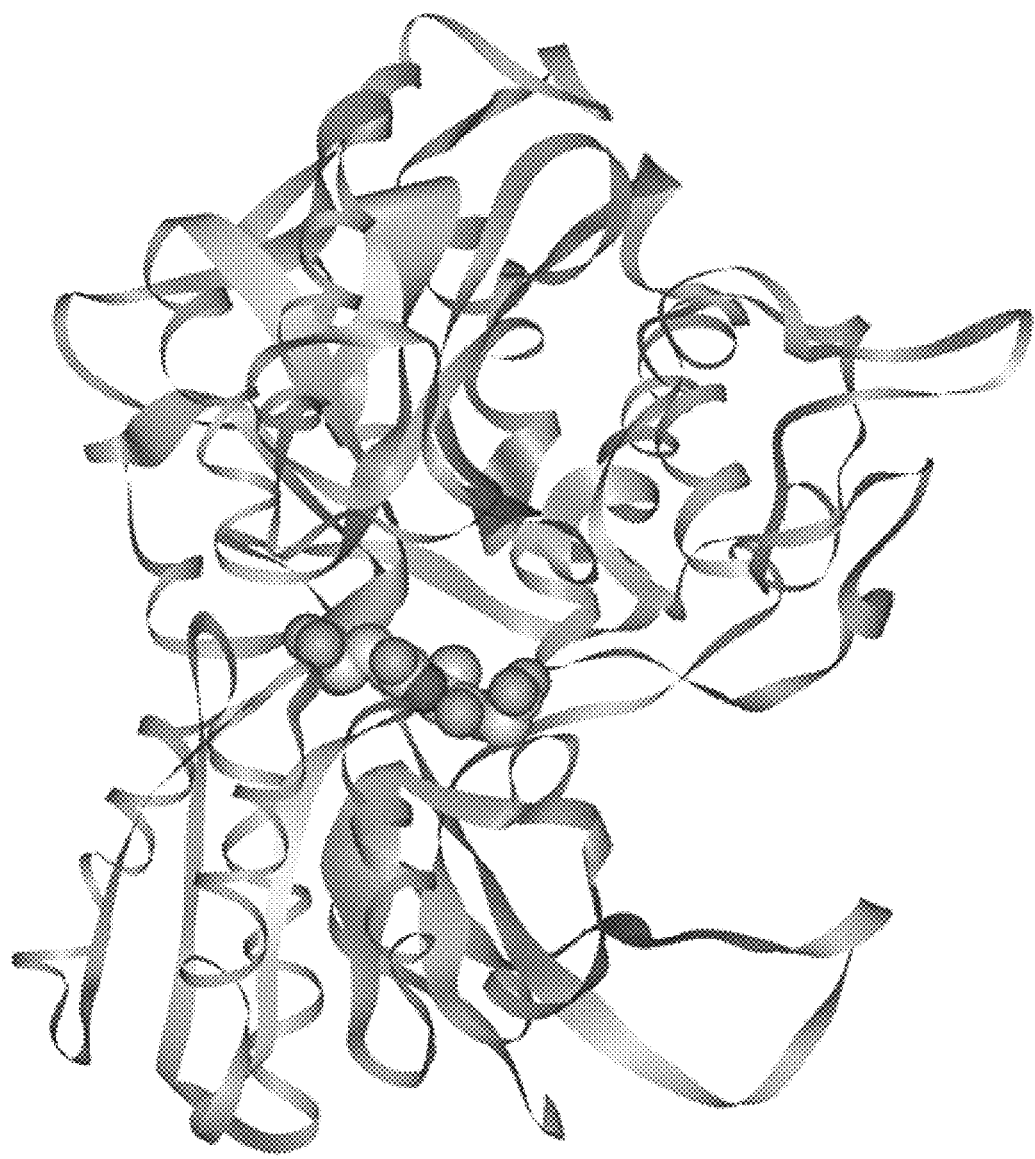
FIGS. 13A-13B show in silico modeling of the interactions between glutathione and a CaSR. A subset of potentially interacting CaSR residues are shown.
Figure 13B:
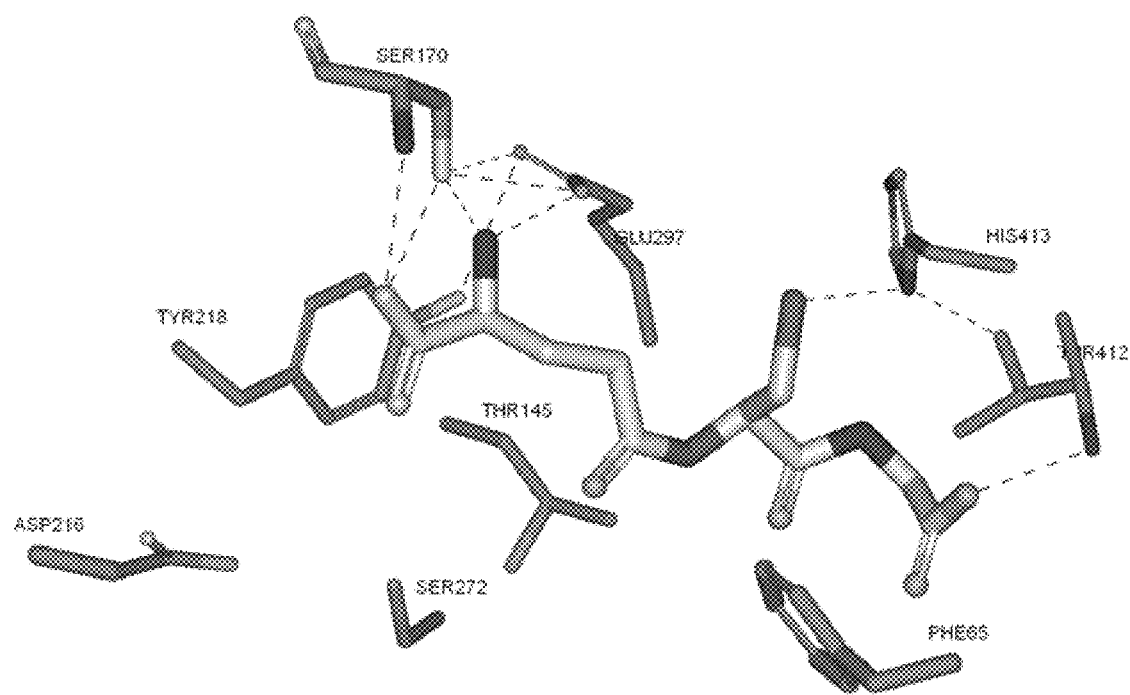

In certain embodiments, structural models of a calcium-sensing receptor can be built using crystal structures of other GPCRs as templates for homology modelling. For example, and not by way of limitation, structural models can be generated using the crystal structures of Group C GPCRs. In certain embodiments, a structural model of a calcium-sensing receptor can be based on a known or a combination of known crystal structures of GPCRs. (See, e.g., Lee et al., Eur J Pharmacol. 2015 May 14. pii: S0014-2999(15)30012-1, which is incorporated by reference in its entirety herein). In certain embodiments, a structural model of a calcium-sensing receptor can be generated based on the crystal structure of an mGluR protein. For example, and not by way of limitation, a structural model of the flytrap domain (VFT) of a calcium-sensing receptor can be generated based on the crystal structure having the protein data base (PDB) ID No. 1EWK. In certain embodiments, a structural model of the 7 transmembrane domain (7TM) of a calcium-sensing receptor can be generated based on the crystal structures of mGluR proteins having PDB ID Nos. 4OR2 and 4OO9. FIG. 13 depict structural models of calcium-sensing receptors that can be used in the disclosed in silico methods. Any suitable modeling software known in the art can be used. In certain embodiments, the Modeller software package can be used to generate the three-dimensional protein structure.

In certain embodiments, the in silico methods of identifying a compound that binds to a calcium-sensing receptor comprises determining whether a test compound interacts with one or more amino acids of a calcium-sensing receptor interacting domain, as described herein.

Compounds that are identified by the disclosed in silico methods can be further tested using the in vitro methods disclosed herein.

3.2 Calcium-Sensing Receptor Binding Site

The present application provides for methods of screening for compounds that modulate the activity of a calcium-sensing receptor, for example, a feline, canine or human calcium-sensing receptor, wherein the compounds interact with one or more amino acids of the calcium-sensing receptor. In certain embodiments, the binding site of a calcium-sensing receptor comprises amino acids within the 7 transmembrane domain (7TM) of the receptor, or Venus Flytrap domain (VFT) domain of the receptor, and can be identified by generating an interaction map of the receptor using in silico modeling, as described herein. In one non-limiting example, the presence of an amino acid in the 7TM or VFT interaction map means that the residue is in the vicinity of the ligand binding environment, and interacts with the ligand.

In certain embodiments, the interaction between a compound and one or more amino acids of the calcium-sensing receptors described herein can comprises one or more hydrogen bond, covalent bond, non-covalent bond, salt bridge, physical interaction, and combinations thereof. The interactions can also be any interaction characteristic of a ligand receptor interaction known in the art. Such interactions can be determined by, for example, site directed mutagenesis, x-ray crystallography, x-ray or other spectroscopic methods, Nuclear Magnetic Resonance (NMR), cross-linking assessment, mass spectroscopy or electrophoresis, cryo-microscopy, displacement assays based on known agonists, structural determination and combinations thereof. In certain embodiments, the interactions are determined in silico, for example, by theoretical means such as docking a compound into a feline or canine calcium-sensing receptor binding pocket as described herein, for example, using molecular docking, molecular modeling, molecular simulation, or other means known to persons of ordinary skill in the art.

In certain embodiments, the interaction is a hydrogen bond interaction.

In certain embodiments, the interaction is a hydrophobic interaction.

In certain embodiments, the compounds identified according to the methods described herein that modulate the activity of a calcium-sensing receptor interact with one or more amino acids in a VFT domain of the calcium-sensing receptor. In certain embodiments, the amino acids that the compounds interact with comprise 1, 2, 3, 4, 5, 6, 7, 8, 9, 10, 11, 12, 13, 14, 15, 16, 17, 18, 19, 20, 21, 22, 23 or more of ASN64, PHE65, ASN102, THR145, SER169, SER170, ASP190, GLN193, ASP216, TYR218, SER271, SER272, GLY273, GLU297, ALA298, TRP299, ALA300, SER301, SER302, LEU304, ALA321, TYR411, THR412, and HIS413 of a calcium-sensing receptor, for example, a calcium-sensing receptor comprising a feline calcium-sensing receptor described by SEQ ID NO:4, a canine calcium-sensing receptor described by SEQ ID NO:5 or a human calcium-sensing receptor described by SEQ ID NO:6.

In certain embodiments, the compounds identified according to the methods described herein that modulate the activity of a calcium-sensing receptor interact with one or more amino acids in a transmembrane domain of the calcium-sensing receptor, for example, a seven transmembrane domain (7TM). In certain embodiments, the amino acids that the compounds interact with comprise 1, 2, 3, 4, 5, 6, 7, 8, 9, 10, 11, 12, 13, 14, 15, 16, 17, 18, 19, 20 or more of ARG680; PHE684; GLY685; PHE688; VAL689 on Helix 3; GLN735 on Helix 4; ALA772; PHE775; LEU776; THR780; CYS781 on Helix 5; PHE814; VAL817; TRP818; PHE821 on Helix 6; GLU837; ALA840; ILE841; ALA844 on Helix 7; and MET771 and GLU767 on the EC2 loop of a calcium-sensing receptor, for example, a calcium-sensing receptor comprising a feline calcium-sensing receptor described by SEQ ID NO:4, a canine calcium-sensing receptor described by SEQ ID NO:5 or a human calcium-sensing receptor described by SEQ ID NO:6.

3.3 In Vitro Methods

The presently disclosed subject matter further provides in vitro methods for identifying compounds that can modulate the activity and/or expression of a calcium-sensing receptor.

The calcium-sensing receptors for use in the presently disclosed methods can include isolated or recombinant calcium-sensing receptors or cells expressing a calcium-sensing receptor, disclosed herein. In certain embodiments, the calcium-sensing receptor for use in the disclosed methods can have the amino acid sequence of SEQ ID NO: 4, 5 or 6, or a fragment or variant thereof In certain embodiments, the calcium-sensing receptor for use in the disclosed method can have at least 85%, at least 90%, at least 91%, at least 92%, at least 93%, at least 94%, at least 95%, at least 96%, at least 97%, at least 98% or at least 99% identity to the amino acid sequence of SEQ ID NO: 4, 5 or 6, or a fragment or variant thereof. In certain embodiments, the calcium-sensing receptor for use in the disclosed method can have the nucleotide sequence of SEQ ID NO: 1, 2, 3 or 7, or a fragment or variant thereof. In certain embodiments, the calcium-sensing receptor for use in the presently disclosed subject matter can include a receptor comprising a nucleotide sequence having at least 85%, at least 90%, at least 91%, at least 92%, at least 93%, at least 94%, at least 95%, at least 96%, at least 97%, at least 98% or at least 99% identity to SEQ ID NO: 1, 2, 3 or 7, or a fragment or variant thereof.

In certain embodiments, the method for identifying compounds that modulate the activity and/or expression of a calcium-sensing receptor comprises measuring the biological activity of a calcium-sensing receptor in the absence and/or presence of a test compound. In certain embodiments, the method can include measuring the biological activity of a calcium-sensing receptor in the presence of varying concentrations of the test compound. The method can further include identifying the test compounds that result in a modulation of the activity and/or expression of the calcium-sensing receptor compared to the activity and/or expression of the calcium-sensing receptor in the absence of the test compound.

In certain embodiments, the compounds identified according to the methods described herein increase the biological activity of a calcium-sensing receptor by at least about 5%, 10%, 15%, 20%, 25%, 30%, 35%, 40%, 45%, 50%, 55%, 60%, 65%, 70%, 75%, 80%, 85%, 90%, 95%, 100%, or more, compared to the biological activity of the calcium-sensing receptor when the compound is not present.

In certain embodiments, the method can further include analyzing two or more, three or more or four or more test compounds in combination. In certain embodiments, the two or more, three or more or four or more test compounds can be from different classes of compounds, e.g., amino acids and small chemical compounds. For example, and not by way of limitation, the method can include analyzing the effect of one or more small chemical test compounds on the biological activity and/or expression of a calcium-sensing receptor in the presence of one or more amino acid test compounds. In certain embodiments, the method for identifying compounds activity and/or expression of a calcium-sensing receptor comprises analyzing the effect of a test compound on the biological activity and/or expression of a calcium-sensing receptor in the presence of a salt, e.g., a calcium salt.

In certain embodiments, the method for identifying compounds that modulate the activity and/or expression of a calcium-sensing receptor comprises determining whether a compound modulates the receptor directly, for example, as an agonist or antagonist. In certain embodiments, the method comprises determining whether a compound indirectly modulates the activity of the receptor (e.g., as an allosteric modulator), for example, by enhancing or decreasing the effect of other compounds on activating or inhibiting receptor activity.

In certain embodiments, the method for identifying compounds that modulate the activity and/or expression of a calcium-sensing receptor comprises expressing a calcium-sensing receptor in a cell line and measuring the biological activity of the receptor in the presence and/or absence of a test compound. The method can further comprise identifying test compounds that modulate the activity of the receptor by determining if there is a difference in receptor activation in the presence of a test compound compared to the activity of the receptor in the absence of the test compound. In certain embodiments, the selectivity of the putative calcium-sensing receptor modulator can be evaluated by comparing its effects on other GPCRs or taste receptors, e.g., umami, fatty acid, T1R, etc. receptors.

Activation of the receptor in the disclosed methods can be detected through the use of a labeling compound and/or agent. In certain embodiments, the activity of the calcium-sensing receptor can be determined by the detection of secondary messengers such as, but not limited to, cAMP, cGMP, IP3, DAG or calcium. In certain embodiments, the activity of the calcium-sensing receptor can be determined by the detection of the intracellular calcium levels. Monitoring can be by way of luminescence or fluorescence detection, such as by a calcium sensitive fluorescent dye. In certain embodiments, the intracellular calcium levels can be determined using a cellular dye, e.g., a fluorescent calcium indicator such as Calcium 4. In certain embodiments, the intracellular calcium levels can be determined by measuring the level of calcium binding to a calcium-binding protein, for example, calmodulin. Alternatively and/or additionally, activity of the calcium-sensing receptor can be determined by detection of the phosphorylation, transcript levels and/or protein levels of one or more downstream protein targets of the calcium-sensing receptor.

The cell line used in the disclosed methods can include any cell type that is capable of expressing a calcium-sensing receptor. Non-limiting examples of cells that can be used in the disclosed methods include HeLa cells, Chinese hamster ovary cells (CHO cells), African green monkey kidney cells (COS cells), *Xenopus* oocytes, HEK-293 cells and murine 3T3 fibroblasts. In certain embodiments, the method can include expressing a calcium-sensing receptor in HEK-293 cells. In certain embodiments, the method can include expressing a calcium-sensing receptor in COS cells. In certain embodiments, the cells constitutively express the calcium-sensing receptor. In another embodiment, expression of the CaSR by the cells is inducible.

In certain embodiments, the cell expresses a calcium-binding photoprotein, wherein the photoprotein luminesces upon binding calcium. In certain embodiments, the calcium binding photoprotein comprises the protein clytin. In certain embodiments the clytin is a recombinant clytin. In certain embodiments, the clytin comprises an isolated clytin, for example, a clytin isolated from *Clytia gregarium*. In certain embodiments, the calcium-binding photoprotein comprises the protein aequorin, for example, a recombinant aequorin or an isolated aequorin, such as an aequorin isolated from *Aequorea victoria*. In certain embodiments, the calcium-binding photoprotein comprises the protein obelin, for example, a recombinant obelin or an isolated obelin, such as an obelin isolated from *Obelia longissima*.

In certain embodiments, expression of a calcium-sensing receptor in a cell can be performed by introducing a nucleic acid encoding a calcium-sensing receptor into the cell. For example, and not by way of limitation, a nucleic acid having the nucleotide sequence set forth in SEQ ID NO: 1, 2, 3 or 7, or a fragment thereof, can be introduced into a cell. In certain embodiments, the introduction of a nucleic acid into a cell can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, Meth. Enzymol. 217:599-618 (1993); Cohen et al., Meth. Enzymol. 217:618-644 (1993); Cline, Pharmac. Ther. 29:69-92 (1985), the disclosures of which are hereby incorporated by reference in their entireties) and can be used in accordance with the disclosed subject matter. In certain embodiments, the technique can provide for stable transfer of nucleic acid to the cell, so that the nucleic acid is expressible by the cell and inheritable and expressible by its progeny. In certain embodiments, the technique can provide for a transient transfer of the nucleic acid to the cell, so that the nucleic acid is expressible by the cell, wherein heritability and expressibility decrease in subsequent generations of the cell's progeny.

In certain embodiments, the nucleic acid encoding a calcium-sensing receptor is comprised in a cloning vector, for example, a pcDNA3.1 vector or a pcDNA5 TO vector, that is introduced into the cell.

In certain embodiments, the method can include identifying compounds that bind to a calcium-sensing receptor. The method can comprise contacting a calcium-sensing receptor with a test compound and measuring binding between the compound and the calcium-sensing receptor. For example, and not by way of limitation, the methods can include providing an isolated or purified calcium-sensing receptor in a cell-free system, and contacting the receptor with a test compound in the cell-free system to determine if the test compound binds to the calcium-sensing receptor. In certain embodiments, the method can comprise contacting a calcium-sensing receptor expressed on the surface of a cell with a candidate compound and detecting binding of the candidate compound to the calcium-sensing receptor. The binding can be measured directly, e.g., by using a labeled test compound, or can be measured indirectly. In certain embodiments, the detection comprises detecting a physiological event in the cell caused by the binding of the compound to the calcium-sensing receptor, e.g., an increase in the intracellular calcium levels. For example, and not by way of limitation, detection can be performed by way of fluorescence detection, such as a calcium sensitive fluorescent dye, by detection of luminescence, or any other method of detection known in the art.

In certain non-limiting embodiments, the in vitro assay comprises cells expressing a calcium-sensing receptor that is native to the cells. Examples of such cells expressing a native calcium-sensing receptor include, for example but not limited to, dog (canine) and/or cat (feline) taste cells (e.g., primary taste receptor cells). In certain embodiments, the dog and/or cat taste cells expressing a calcium-sensing receptor are isolated from a dog and/or cat and cultured in vitro. In certain embodiments, the taste receptor cells can be immortalized, for example, such that the cells isolated from a dog and/or cat can be propagated in culture.

In certain embodiments, expression of a calcium-sensing receptor in a cell can be induced through gene editing, for example, through use of the CRISPR gene editing system to incorporate a calcium-sensing receptor gene into the genome of a cell, or to edit or modify a calcium-sensing receptor gene native to the cell.

In certain embodiments, the in vitro methods of identifying a compound that binds to a calcium-sensing receptor comprises determining whether a test compound interacts with one or more amino acids of a calcium-sensing receptor interacting domain, as described herein.

In certain embodiments, compounds identified as modulators of a calcium-sensing receptor can be further tested in other analytical methods including, but not limited to, in vivo assays, to confirm or quantitate their modulating activity.

In certain embodiments, methods described herein can comprise determining whether the calcium-sensing receptor modulator is a kokumi taste enhancing compound, e.g., a calcium-sensing receptor agonist.

In certain embodiments, the methods of identifying a calcium-sensing receptor modulator can comprise comparing the effect of a test compound to a calcium-sensing receptor agonist. For example, a test compound that increases the activity of the receptor compared to the activity of the receptor when contacted with a calcium-sensing receptor agonist can be selected as a calcium-sensing receptor modulating compound (e.g., as an agonist).

In certain embodiments, the methods of identifying a calcium-sensing receptor modulator can comprise determining whether a test compound modulates the activity of the receptor when the receptor is contacted with an agonist, or whether the test compound can modulate the activity of a positive allosteric modulator (PAM). Test compounds that increase or decrease the effect of said agonist or PAM on the receptor can be selected as a calcium-sensing receptor modulating compound (e.g., as an allosteric modulator).

Calcium-sensing receptor agonists and PAMs that can be used according to said methods can comprise one or more compounds described by Table 1.

TABLE 1

| Compound: | CAS number: | Chemical structure: |
|---|---|---|
| Calcium (Ca$^{2+}$) (agonist) | 7440-70-2 | CaCl$_2$ |
| Magnesium (Mg$^{2+}$) (agonist) | 7786-30-3 | MgCl$_2$ |
| Spermine (agonist) | 71-44-3 | |
| Spermidine (agonist) | 124-20-9 | |
| Putrescine (not active) | 110-60-1 | |
| L-Glutathione (agonist) | 70-18-8 | |
| Neomycin (agonist) | 1404-04-2 | |
| Poly-L-Arginine (agonist) | 26982-20-7 | |
| Cinacalcet (PAM) | 226256-56-0 | |

TABLE 1-continued

CaSR agonists and PAMs

| Compound: | CAS number: | Chemical structure: |
|---|---|---|
| Calindol (PAM) | 729610-18-8 | 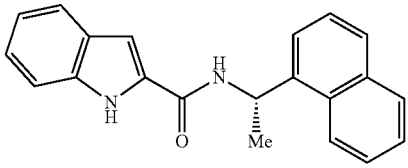 [SMILES: C[C@H](NC(=O)c1cc2ccccc2[nH]1)c1cccc2ccccc12] |

In certain embodiments, the calcium-sensing receptor modulators of the present disclosure comprise a salt of the calcium-sensing receptor modulator, for example, but not limited to, an acetate salt or a formate salt. In certain embodiments, the calcium-sensing receptor modulator salt comprises an anion (−) (for example, but not limited to, $Cl^-$, $O^{2-}$, $CO_3^{2-}$, $HCO_3^-$, $OH^-$, $NO_3^-$, $PO_4^{3-}$, $SO_4^{2-}$, $CH_3COO^-$, $HCOO^-$ and $C_2O_4^{2-}$) bonded via an ionic bond with a cation (+) (for example, but not limited to, $Al^{3+}$, $Ca^{2+}$, $Na^+$, $K^+$, $Cu^{2+}$, $H^+$, $Fe^{3+}$, $Mg^{2+}$, $NH_4^+$ and $H_3O^+$). In other embodiments, the calcium-sensing receptor agonist salt comprises a cation (+) bonded via an ionic bond with an anion (−).

In certain embodiments, the calcium-sensing receptor modulators of the present application are identified through in silico modeling of a calcium-sensing receptor ("Kokumi receptor"), e.g., a feline or a canine calcium-sensing receptor, wherein the calcium-sensing receptor agonists of the present application comprise a structure that fits within a binding site of the calcium-sensing receptor. In certain embodiments, the in silico method comprises the in silico methods described above and in the Examples section of the present application.

In certain embodiments, the calcium-sensing receptor modulators of the present application are identified through an in vitro method, wherein the calcium-sensing receptor agonist compounds activate and/or modulate a calcium-sensing receptor, disclosed herein, expressed by cells in vitro. In certain embodiments, the in vitro method comprises the in vitro methods described above and in the Examples section of the present application.

EXAMPLES

The presently disclosed subject matter will be better understood by reference to the following Examples, which are provided as exemplary of the invention, and not by way of limitation.

Example 1—Identification of CaSR Modulators Using In Silico Assays

The present example describes the computational modeling of the feline and canine calcium-sensing receptor (CaSR) to identify putative compound modulators.

Computational approaches were used to analyze the three-dimensional structure of the calcium-sensing receptor to identify polypeptide regions that can be exploited to selectively modulate the calcium-sensing receptor. A structural homology model of the various domains of the calcium-sensing receptor was generated based on the structures of class C GPCRs (See Binet et al., J. Biol. Chem, 282(16): 12154-63 (2007); Wu et. al., Science, 344(6179):58-64 (2014); and Dore et al., Nature 511:557-562 (2014); each of which are incorporated by reference herein in their entireties). The homology models were built with the Discovery Studio (DS) suite of programs from Accelrys. Specifically, the Modeller program from DS was used (see Eswar et al., Current Protocols in Bioinformatics, Supplement 15:5.6.1-5.6.30 (2006), which is incorporated by reference herein in its entirety). "In silico" screening was used to identify compounds that interact with the structural domains of the calcium-sensing receptor.

Figure 12B:
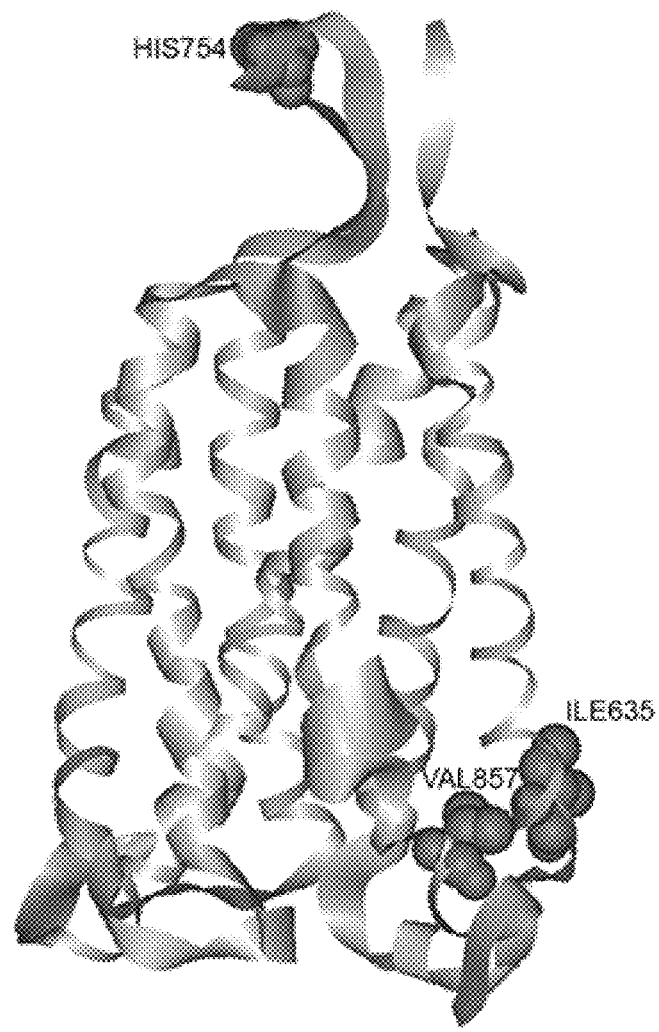

The GPCR group C family of proteins includes T1R1, T1R2, T1R3, CaSR, GabaB and mGlu proteins. Group C proteins have (1) a large external domain, called a Venus Flytrap domain (VFT), (2) a 7 transmembrane domain (7TM) and (3) a cysteine rich domain that connects the VFT and the 7TM. A sequence alignment of the amino acid sequence of the feline and canine CaSRs was performed and showed an overall 95% sequence identity (FIG. 9). A sequence alignment of the amino acid sequences of the feline, canine and human CaSRs was performed and showed an overall 93.2% sequence identity (FIG. 10). The VFT domain of CaSR consists of amino acids 1-523 and the 7TM domain consists of amino acids 601-865. The active site of the feline, canine and human VFT domain and the allosteric site of their 7TM domains are almost identical (FIGS. 11 and 12). Only two differences were observed near the active site of feline and human CaSR VFTs (FIG. 11). FIG. 12 shows the differences in amino acids within the 7TM domains are shown on the structure in the Corey-Pauling-Koltun (CPK) representation. No differences were observed in the makeup of the allosteric site of CaSR.

A homology model of the VFT domain of the CaSR receptor was generated based on numerous crystal structures of mGlu available from the Protein Data Bank (PDB). There is 27% sequence identity between the VFT domain of mGluR1 (1EWK structure from PDB) and the CaSR alignment of VFT domains. Glutathione, a known CaSR agonist, was docked to the hinge area of CaSR (FIG. 13). Without being bound to a particular theory, it appears that glutathione binds to the hinge region of the VFT domain of CaSR, where the carboxyl end of glutathione forms a hydrogen bond with the backbone of CaSR (FIG. 13). Glutathione was observed to have potential interactions with amino acids ASN64, PHE65, ASN102, THR145, SER169, SER170, ASP190, GLN193, ASP216, TYR218, SER271, SER272, GLY273, GLU297, ALA298, TRP299, ALA300, SER301, SER302, LEU304, ALA321, TYR411, THR412, and HIS413 (FIG. 13).

Phenylalanine, a compound that can bind CaSR, was docked in the in silico model along with Calcium ($Ca^{2+}$), which was docked to the hinge region of CaSR. $Ca^{2+}$ formed a salt bridge to ASP216 and GLU297, and the carboxyl group of phenylalanine formed interactions with the hinge region of CaSR and with the calcium. The following amino acids were shown to interact with phenylalanine: TYR218, THR145, SER147, SER170 and SER272.

Figure 14:
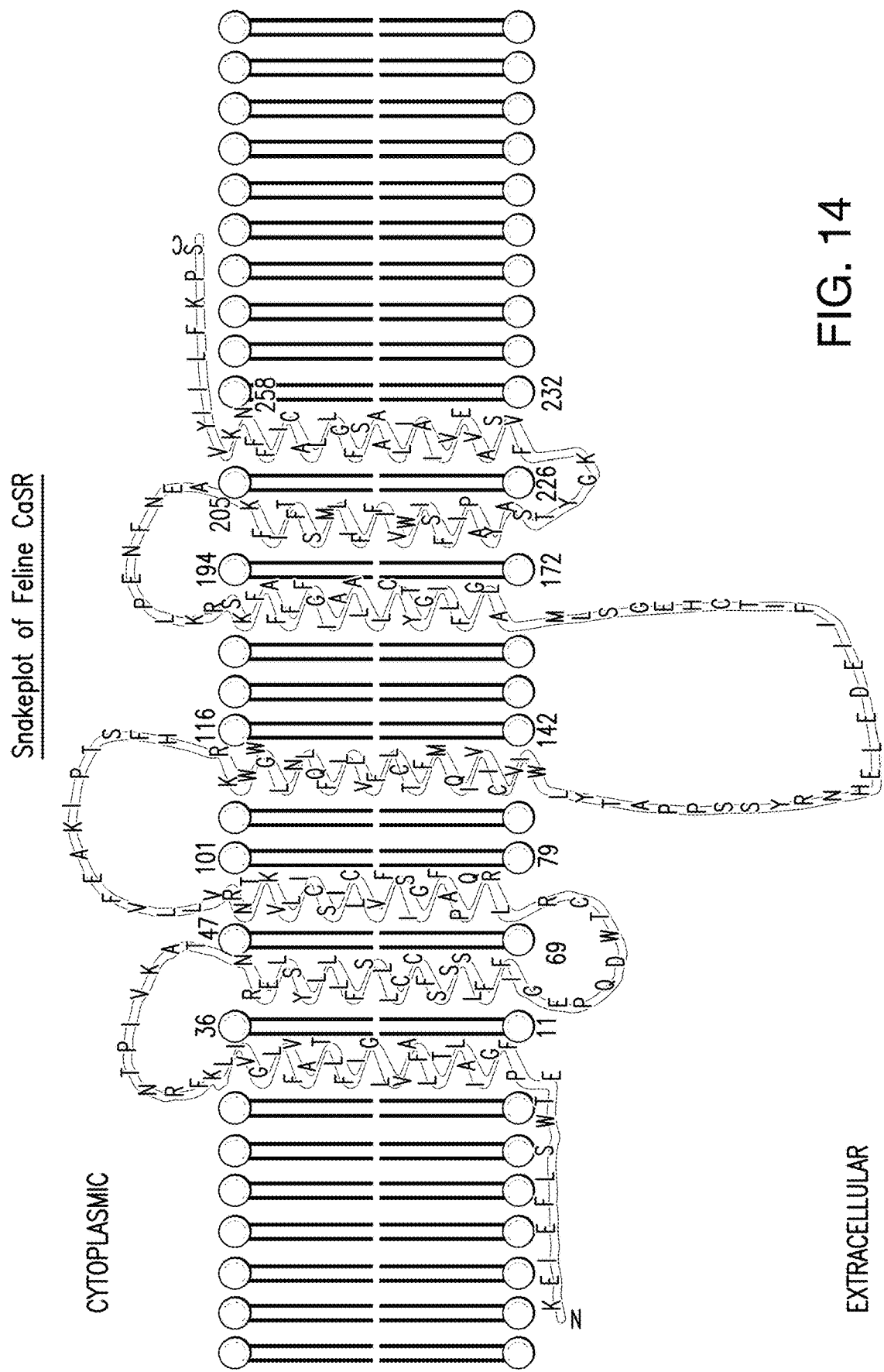
FIG. 14 shows the snake plot of the feline CaSR.
Figure 15:
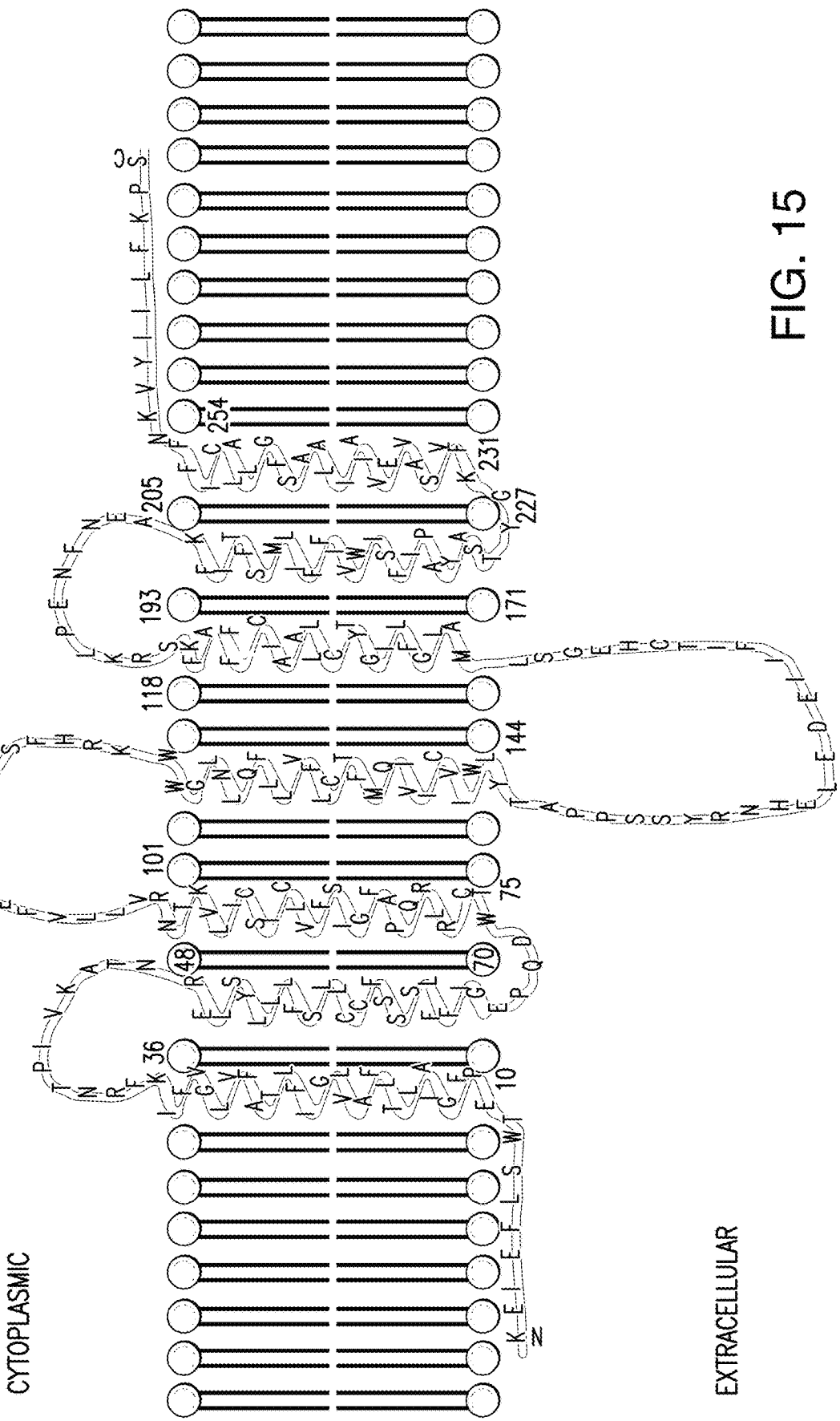
FIG. 15 shows the snake plot of the canine CaSR.
Figure 16:
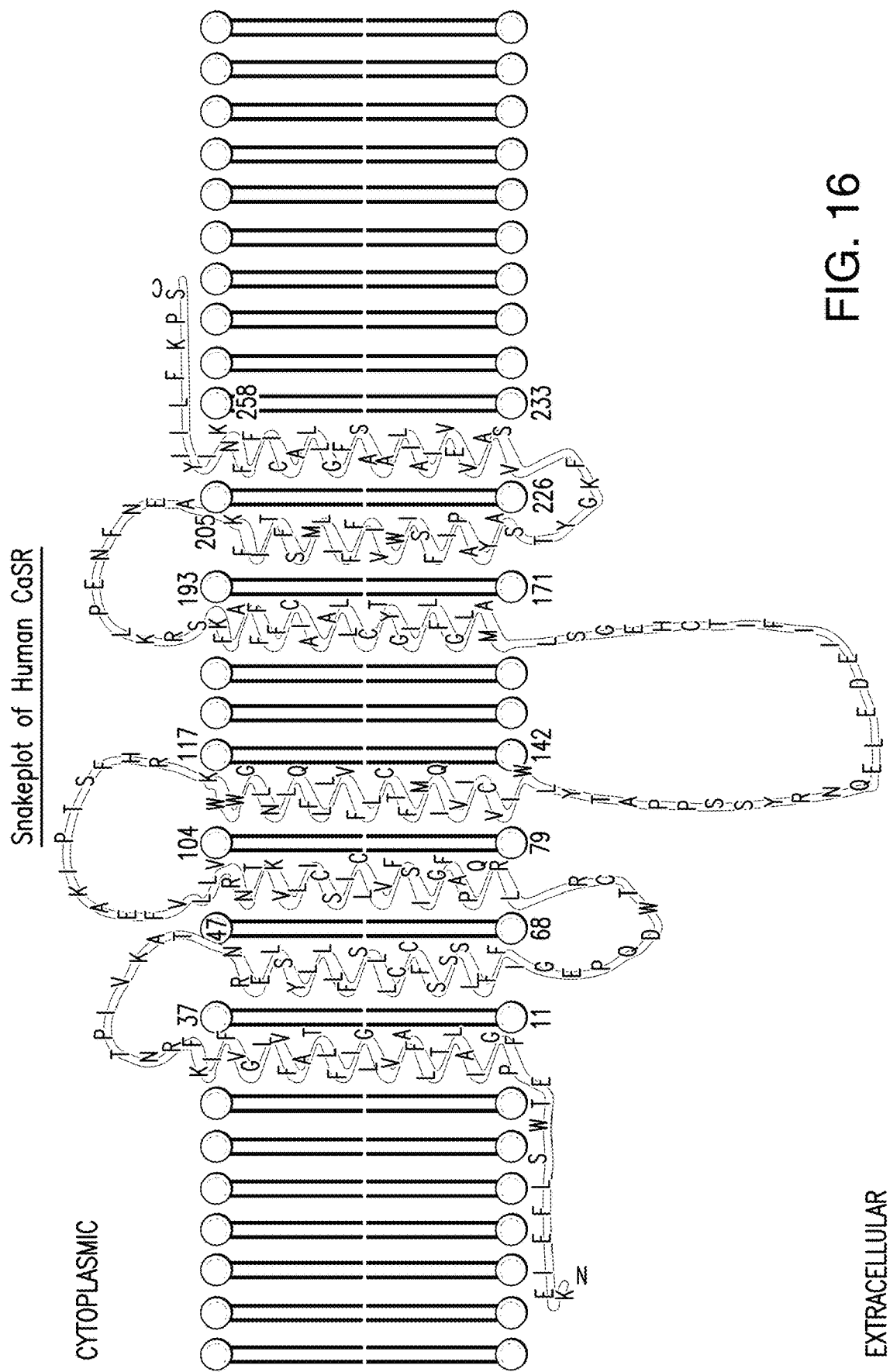
FIG. 16 shows the snake plot of the human CaSR.
Figure 17A:
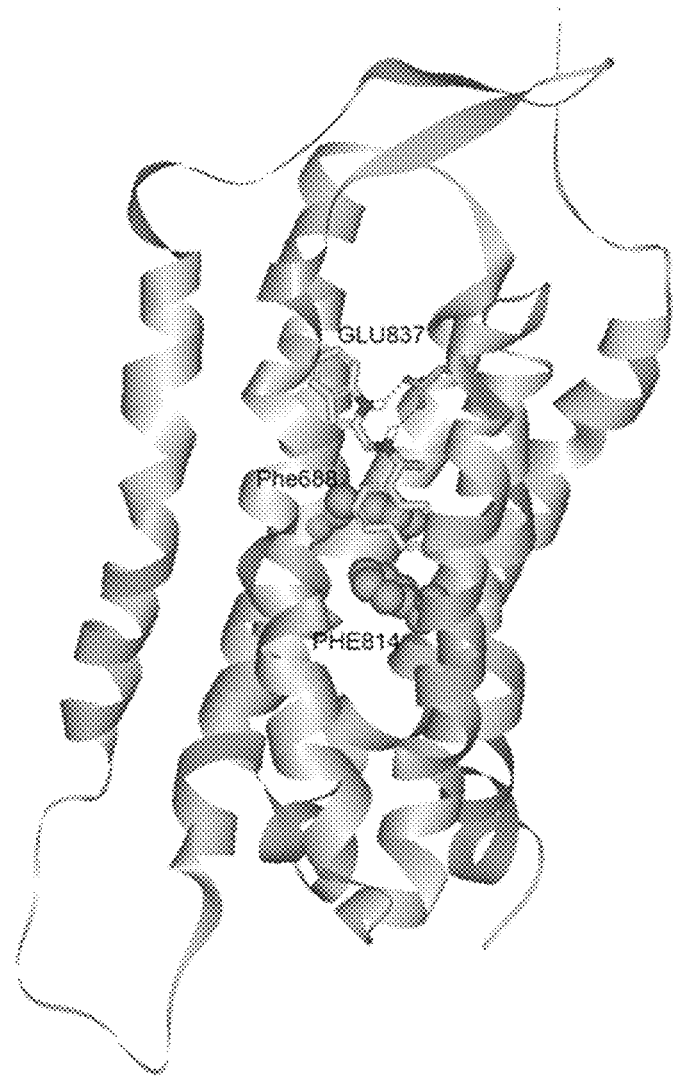
FIGS. 17A-17B show in silico modeling of the interactions between calindol and a CaSR. A subset of potentially interacting CaSR residues are depicted.
Figure 17B:
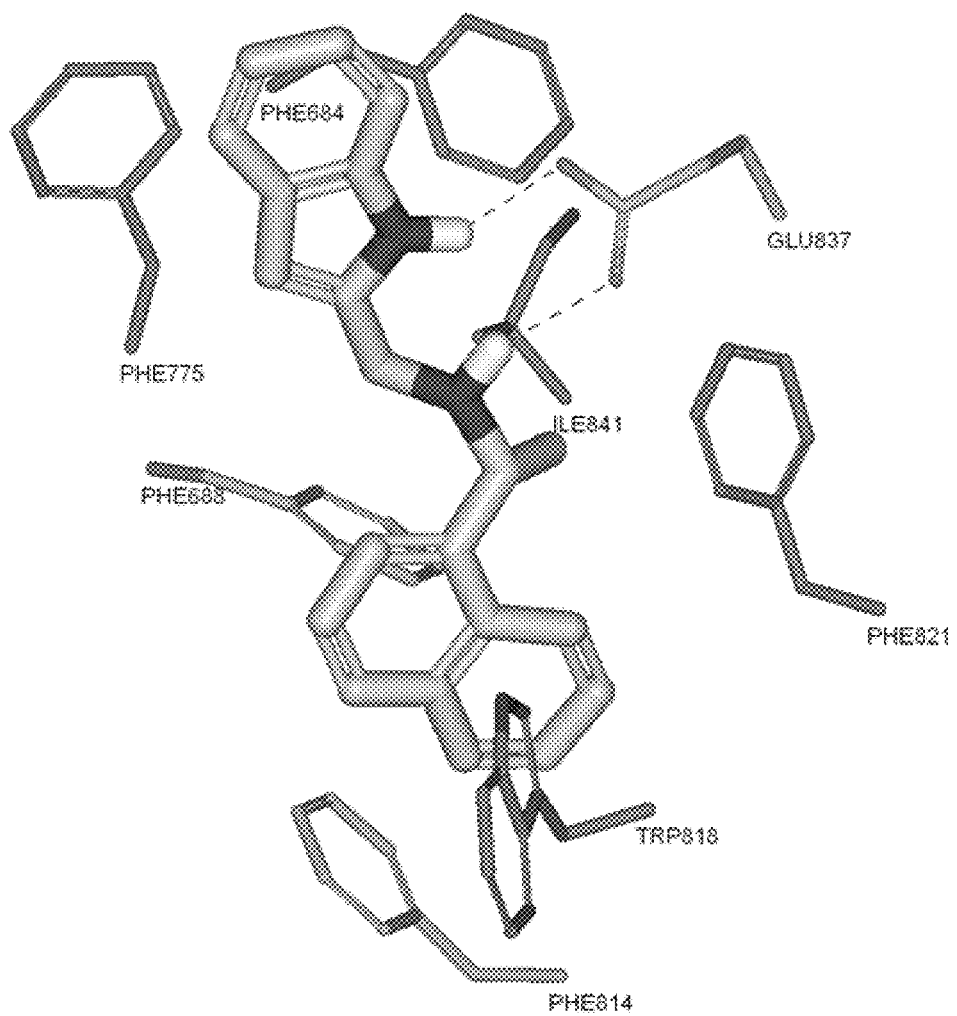
Figure 18A:
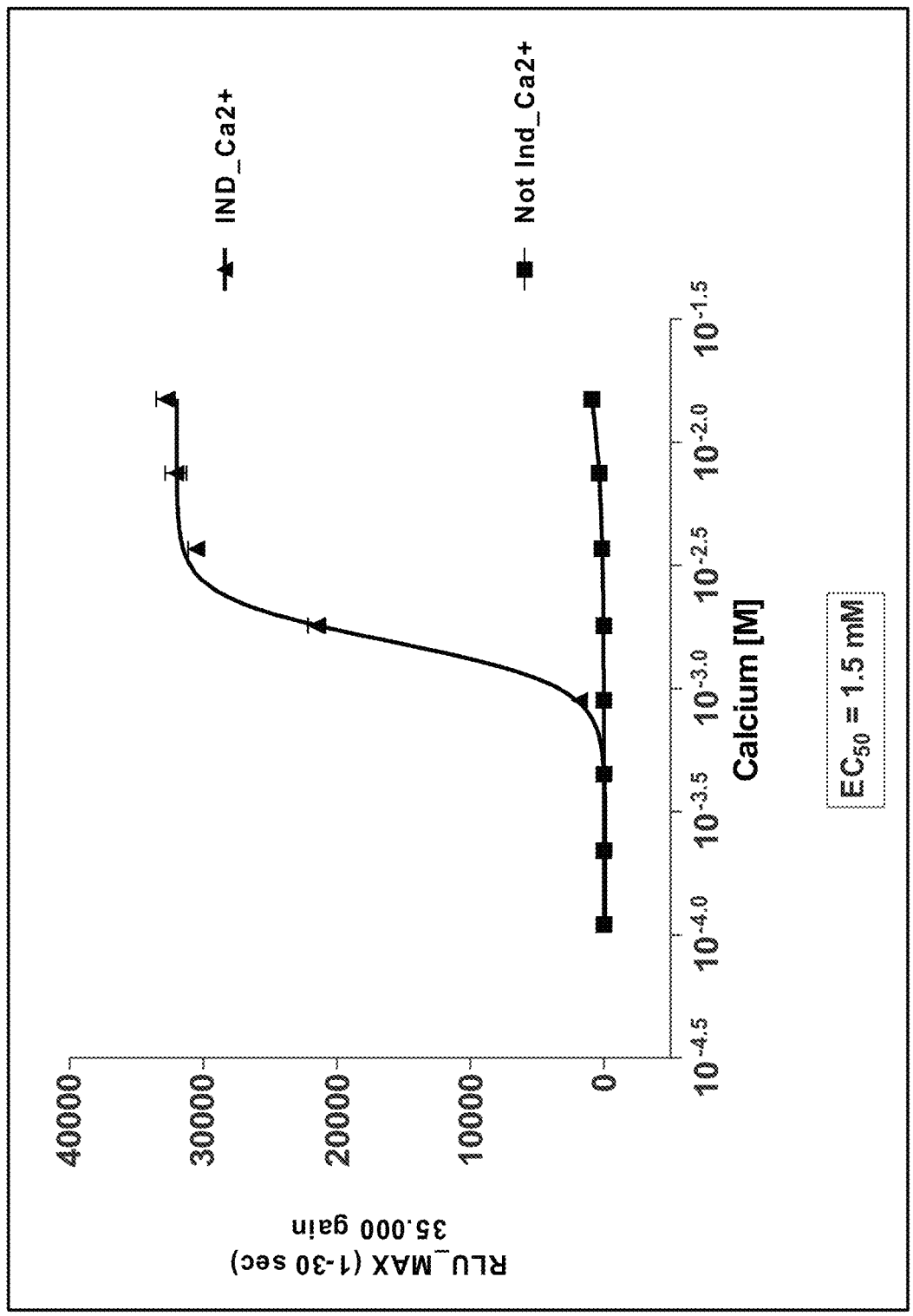
FIGS. 18A-18J show dose response curves for 10 fCaSR ligands determined in an in vitro cellular assay for activation of fCaSR by the 10 ligands in agonist mode.
Figure 18B:
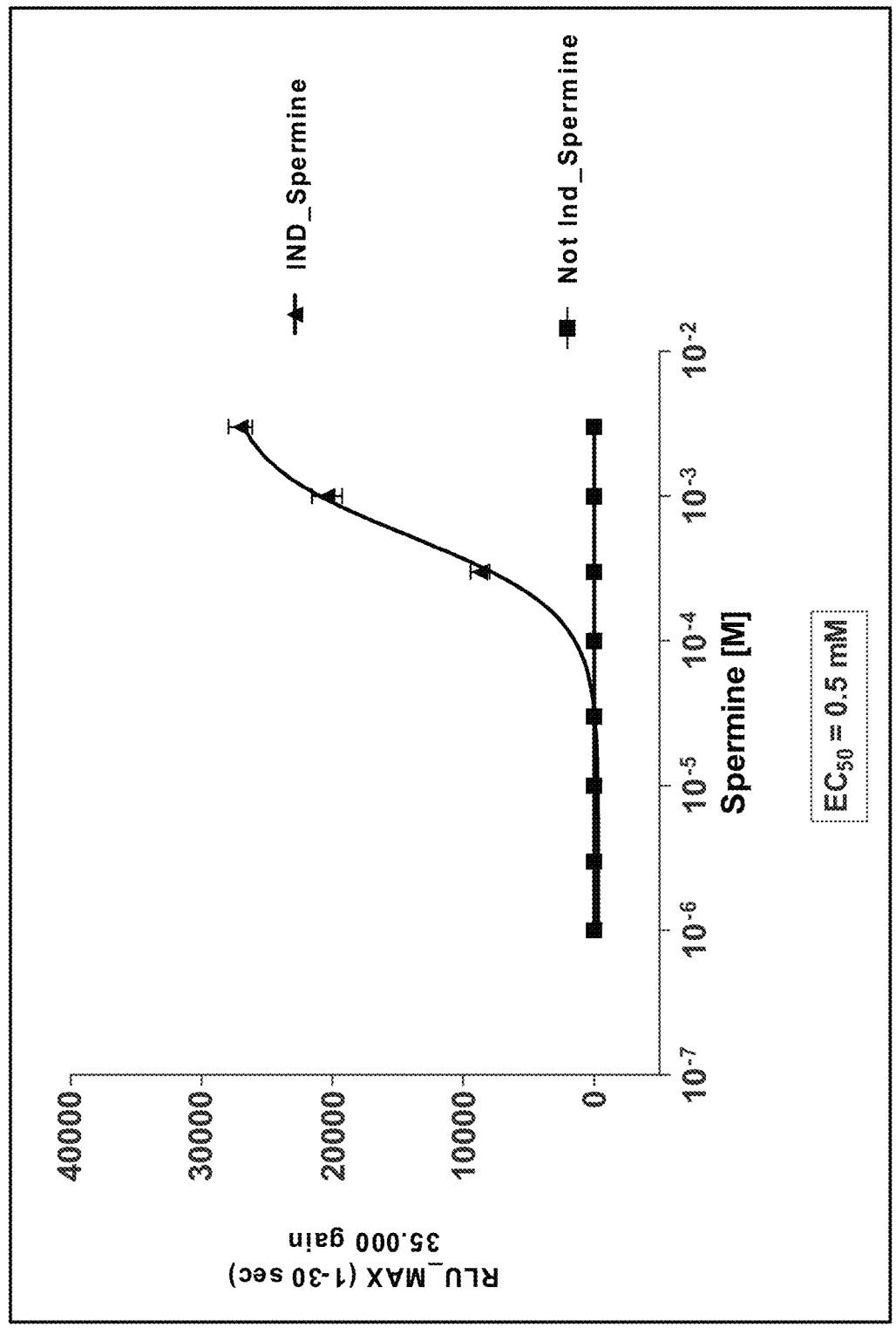
Figure 18C:
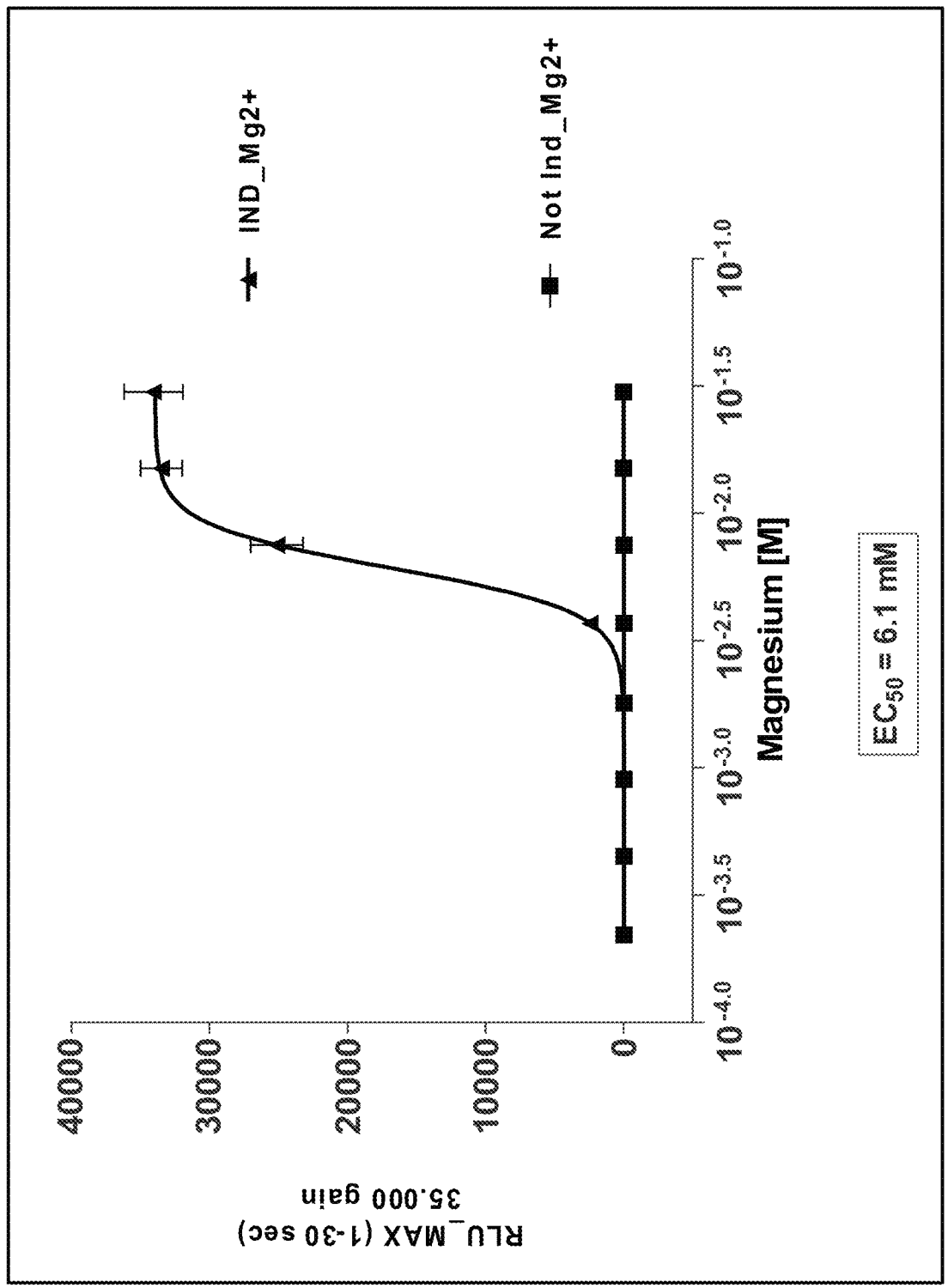
Figure 18D:
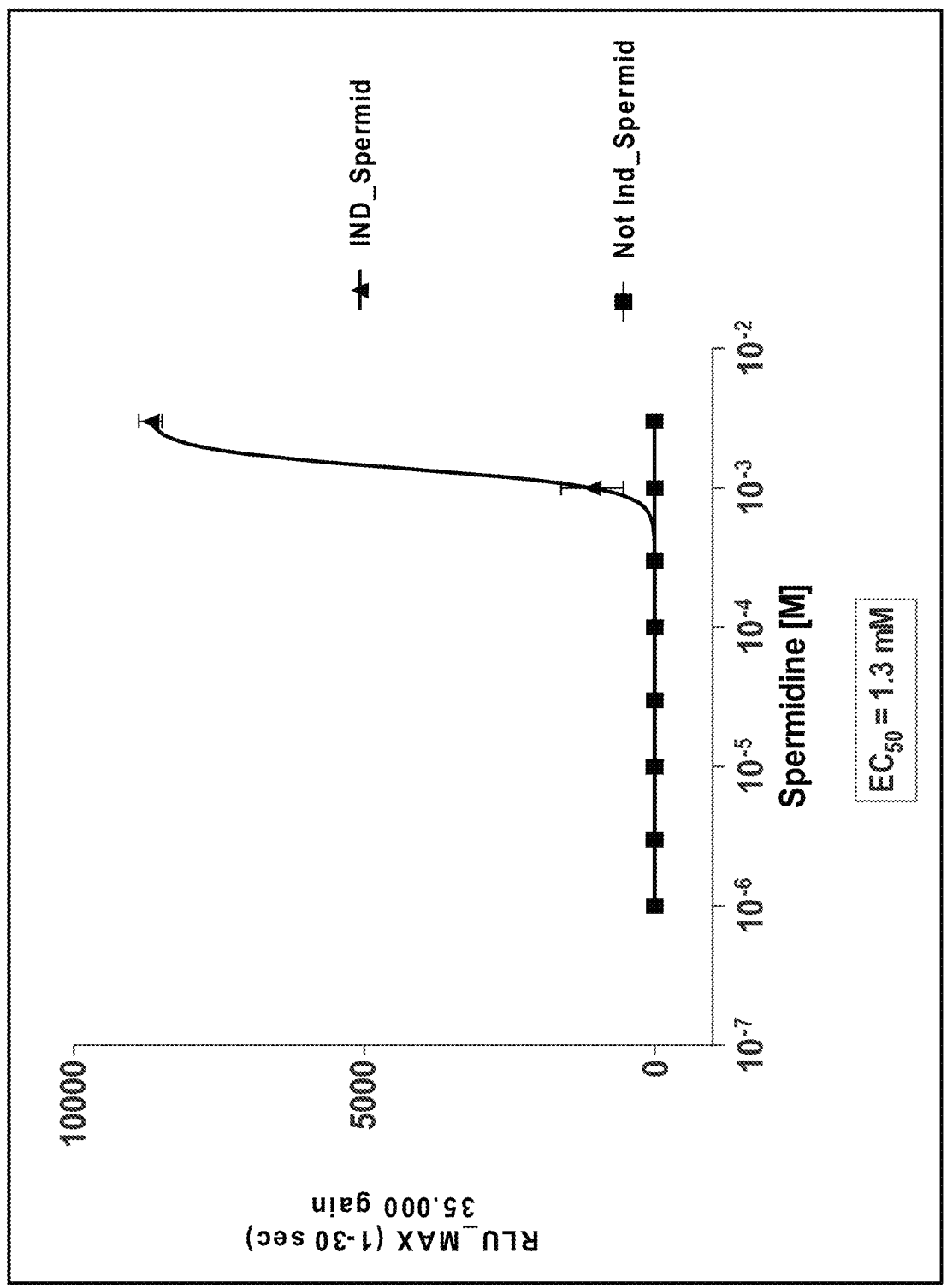
Figure 18E:
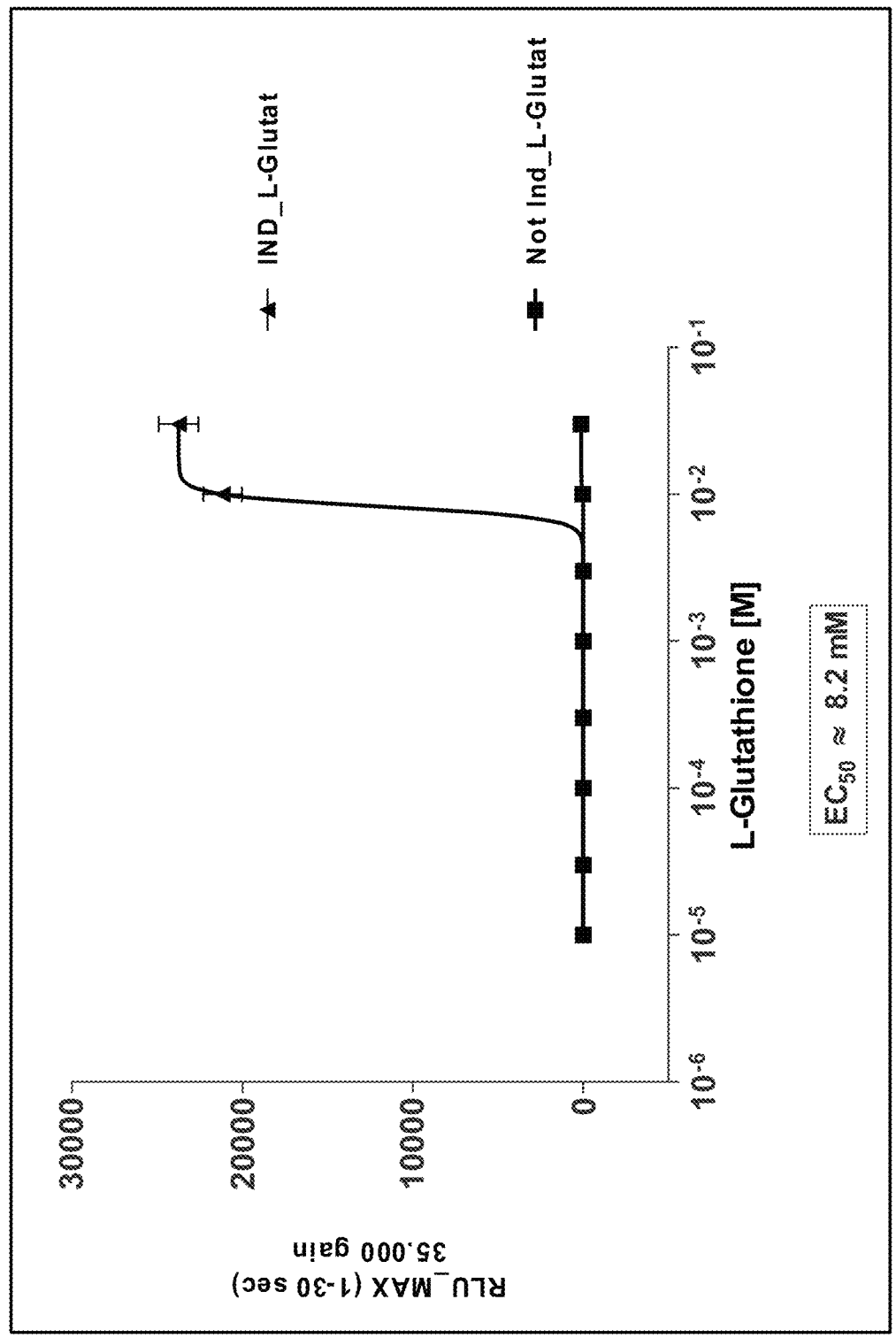
Figure 18F:
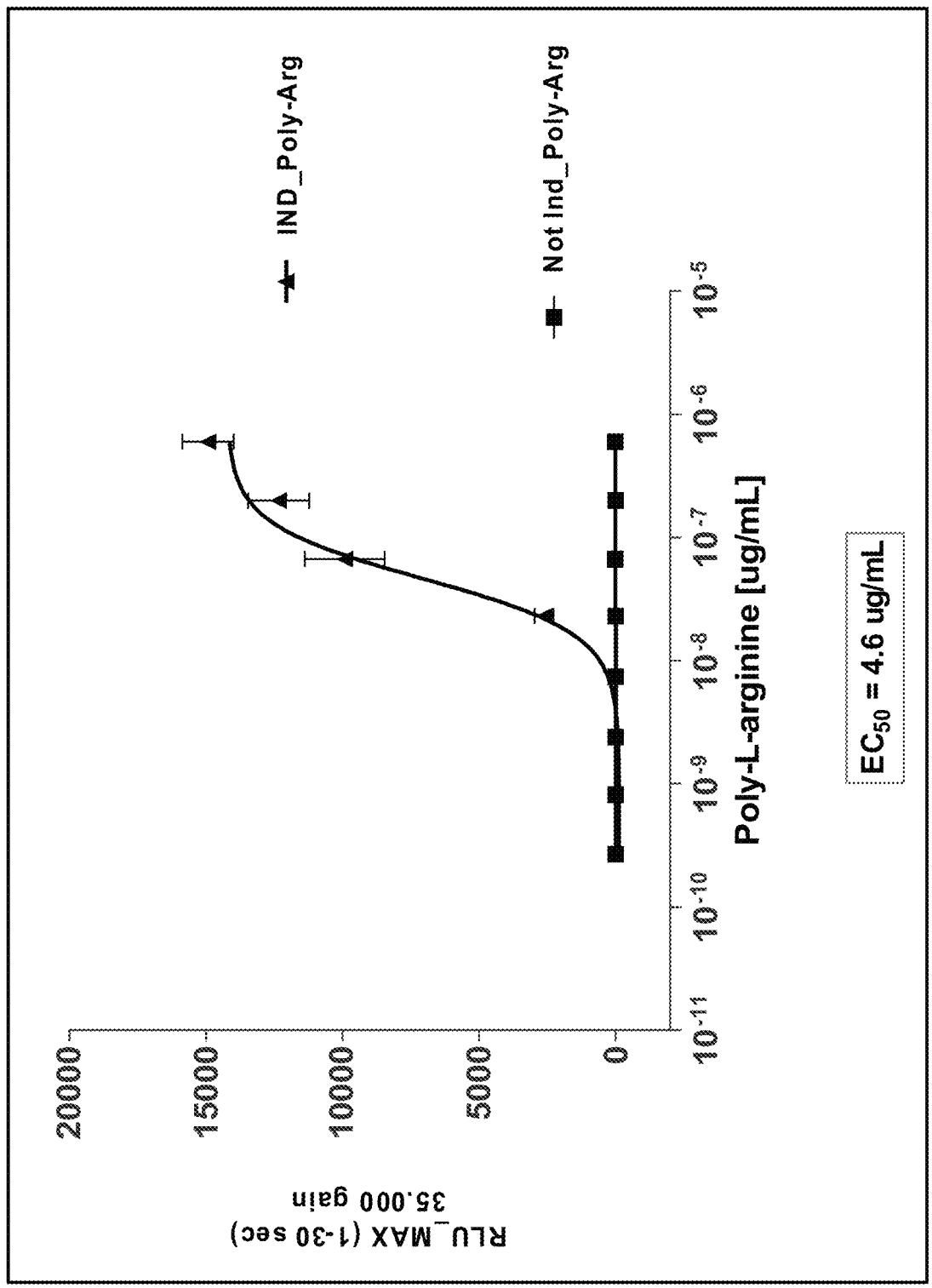
Figure 18G:
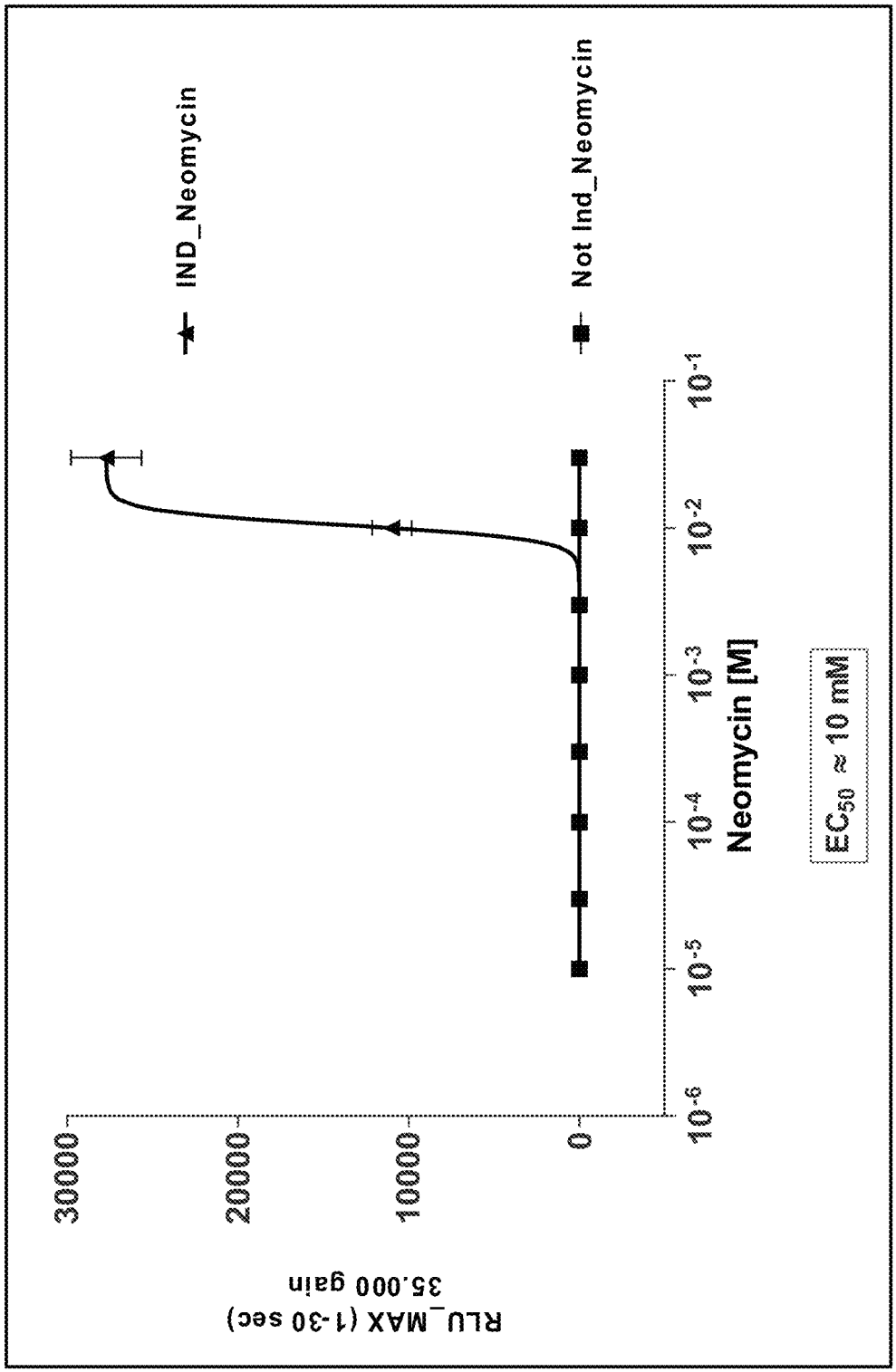
Figure 18H:
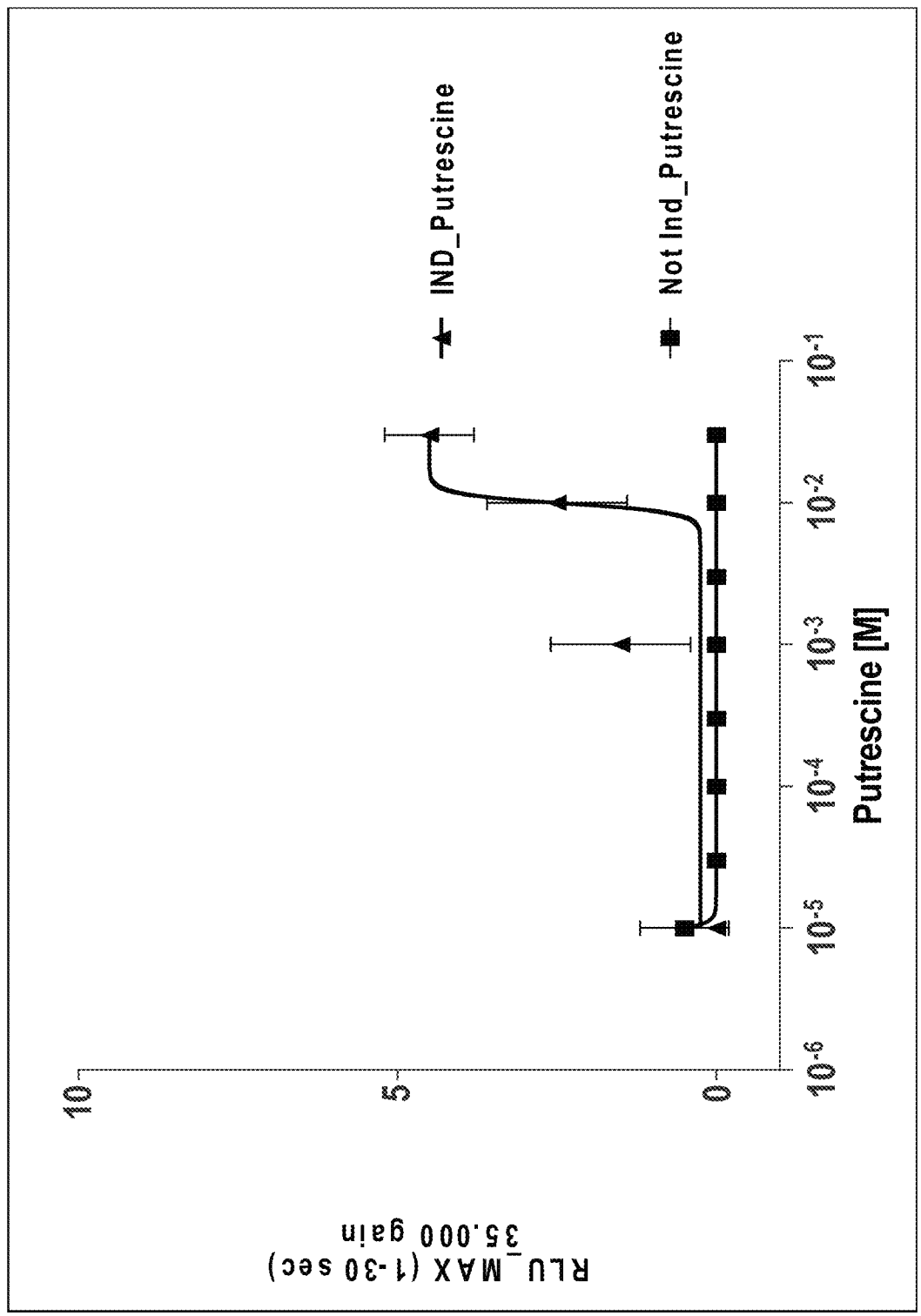
Figure 18I:
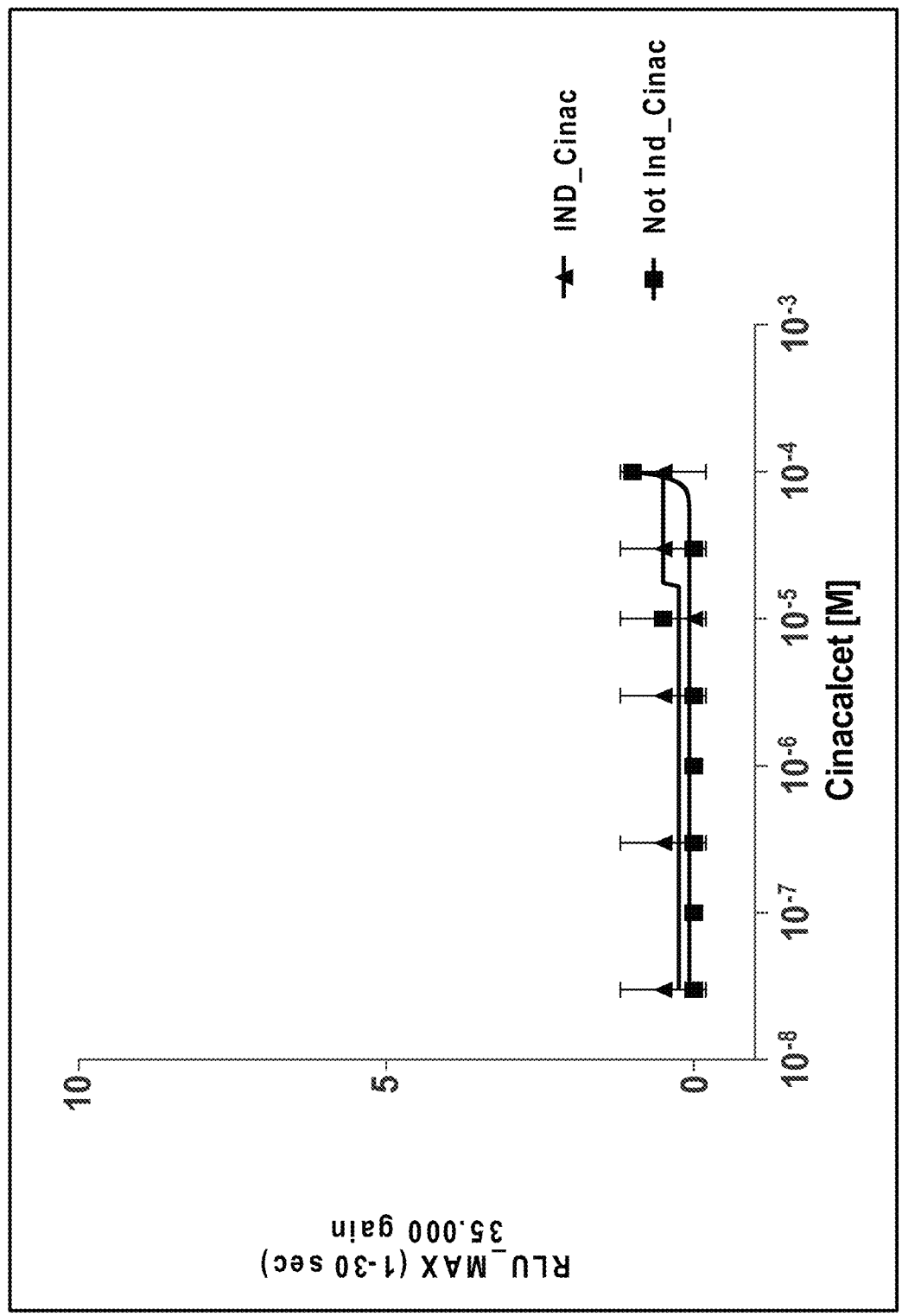
Figure 18J:
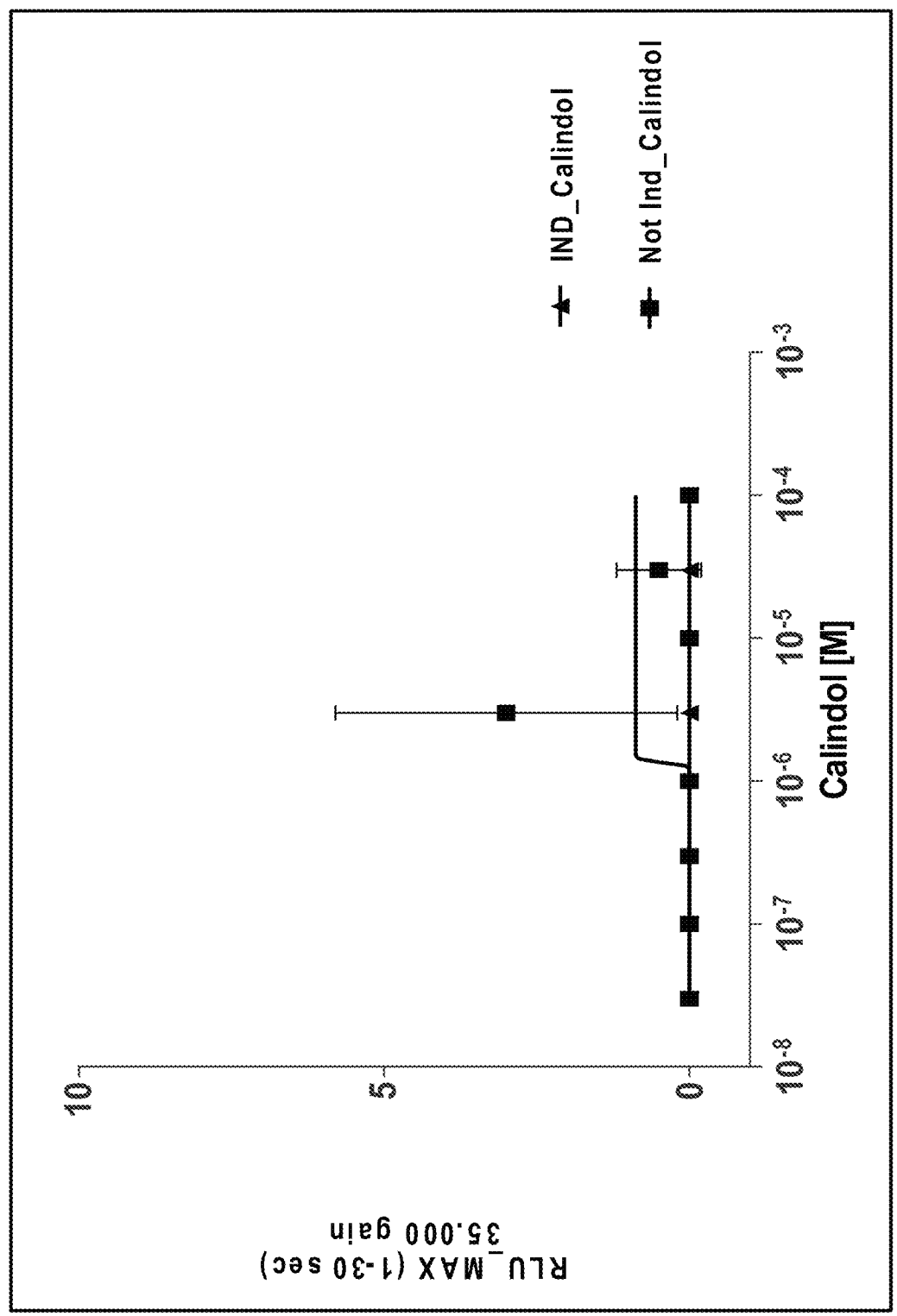

A homology model of the feline and canine CaSR 7M domain was generated based on the crystal structures of 4OR2 and 4OO9 from PDB (see helix plot of FIG. 14; see also, FIGS. 14, 15 and 16 for helix plots of canine, feline and human CaSRs, respectively). 4OR2 is the crystal structure of the transmembrane domain of mGluR1 from Group C GPCR bound to a negative allosteric modulator (NAM) (see Wu et. al., Science, 344(6179):58-64 (2014), which is incorporated by reference herein in its entirety). 4OO9 is the crystal structure of the transmembrane domain of mGluR5 from Group C GPCR bound to NAM (see Dore et al., Nature 511:557-562 (2014), which is incorporated by reference herein in its entirety). There is approximately 30% sequence identity between the 7TM domain of mGluR1 (4OR2 structure from PDB) and the CaSR 7TM domain. The known potent positive allosteric modulator, calindol, was docked into the allosteric site of the transmembrane domain of human, canine and feline CaSR (FIG. 17). The docking program, BioDock, from BioPredict was used. Calindol was observed to have the following potential interactions with the amino acids of allosteric site of human, canine and feline CaSR: ARG680; PHE684; GLY685; PHE688; VAL689 on Helix 3; GLN735 on Helix 4; ALA772; PHE775; LEU776; THR780; CYS781 on Helix 5; PHE814; VAL817; TRP818; PHE821 on Helix 6; GLU837; ALA840; ILE841; ALA844 on Helix 7; and MET771 and GLU767 on the EC2 loop of the CaSR.

Example 2—Identification of Feline CaSR Agonists Using In Vitro Assays

The present example describes an in vitro assay for identifying compounds that modulate the activation of the feline calcium-sensing receptor.

Compounds identified by in silico modeling with the calcium-sensing receptor, as detailed above in Example 1, as putative calcium-sensing receptor modulators are selected for further testing in vitro. In vitro functional characterization of the selected agonist compounds is used to evaluate the effectiveness of a putative agonist compound in activating the calcium-sensing receptor.

HEK293 cells that stably express a calcium-sensing receptor are exposed to putative compounds to modulate the activity and/or expression of the calcium-sensing receptor. Activation of the calcium-sensing receptor is detected by a change in intracellular calcium levels using a calcium sensitive fluorescent dye. Cells that do not express the calcium-sensing receptor or that are not contacted with the compound are used as a control. A FLIPR® Tetra or a FlexStation® 3 is used for data capture.

For each putative calcium-sensing receptor modulator, dose response curves are generated and the $EC_{50}$ value of the putative calcium-sensing receptor modulator is determined. The term half maximal effective concentration ($EC_{50}$) refers to the concentration of a compound which induces a response halfway between the baseline and the maximum after a specified exposure time.

Example 3—Identification of Canine CaSR Agonists Using In Vitro Assays

The present example describes an in vitro assay for identifying compounds that modulate the activation of the canine calcium-sensing receptor.

Compounds identified by in silico modeling with a calcium-sensing receptor, as detailed above in Example 1, as putative calcium-sensing receptor modulators are selected for further testing in vitro. In vitro functional characterization of the selected modulators is used to evaluate the effectiveness of a putative agonist compound in activating the calcium-sensing receptor.

HEK293 cells that stably express the canine CaSR are exposed to putative compounds to modulate the activity and/or expression of the calcium-sensing receptor. Activation of the calcium-sensing receptor is detected by a change in intracellular calcium levels using a calcium sensitive fluorescent dye. Cells that do not express the calcium-sensing receptor or that are not contacted with the compound are used as a control. A FLIPR® Tetra or a FlexStation® 3 is used for data capture.

For each putative calcium-sensing receptor modulator, dose response curves are generated and the $EC_{50}$ value of the putative calcium-sensing receptor modulator is determined. The term half maximal effective concentration ($EC_{50}$) refers to the concentration of a compound which induces a response halfway between the baseline and the maximum after a specified exposure time.

Example 4—In Vitro Assay for Identification of Feline CaSR Modulators

The present example describes an in vitro assay for identifying compounds that modulate the activation of the feline calcium-sensing receptor.

Summary. The full length coding sequence of the calcium-sensing receptor (CaSR, a GPCR (3, C or Glutamate family), naturally coupled to Gαq/11 and Gαi (ligand-directed signaling)) from *Felis catus* (fCaSR) having the sequence described by SEQ ID NO: 7 was synthesized and sub-cloned into suitable expression vectors. The cat CaSR expression constructs were stably transfected in two mammalian cell lines, the HEK-natClytin and the HEK T-Rex/natClytin, two cell lines that allow for detection of changes in intracellular calcium levels through luminescence. A pure selected clone (K 5.1) was used to analyze 12 CaSR ligands (including calcium as a reference agonist control) in a high-throughput screening (HTS) multi-plate test for agonist and positive allosteric modulator (PAM) effects. 7 of the ligands tested (including calcium control) were identified as agonists, and 2 were identified as PAM of CaSR, demonstrating that the in vitro cellular assay described by the present study is a reliable, reproducible and robust functional cell based assay for the cat CaSR receptor suitable for HTS.

Results. HEK-natClytin and HEK T-Rex/natClytin cells were transfected with vectors comprising fCaSR. Mock transfections were carried out in parallel as negative controls. After antibiotic selections, a 1° limiting dilution of the two transfected target and mock pools were performed and then analyzed with calcium as a reference agonist and luminescence photoprotein as read out of activated fCaSR using a FLIPR® Tetra screening system. Based on clone pool analysis results, the HEK T-Rex/natClytin responding clones were selected for further evaluation. A 2° limiting dilution of selected clones was performed. Four of the 2° limiting dilution clones were characterized, and two responding clones, (K1.5,K10.3) were completely optimized for cell growth, cell density and cell seeding time conditions, for DMSO sensitivity, for signal stability over time and for frozen cells use.

Figure 19A:
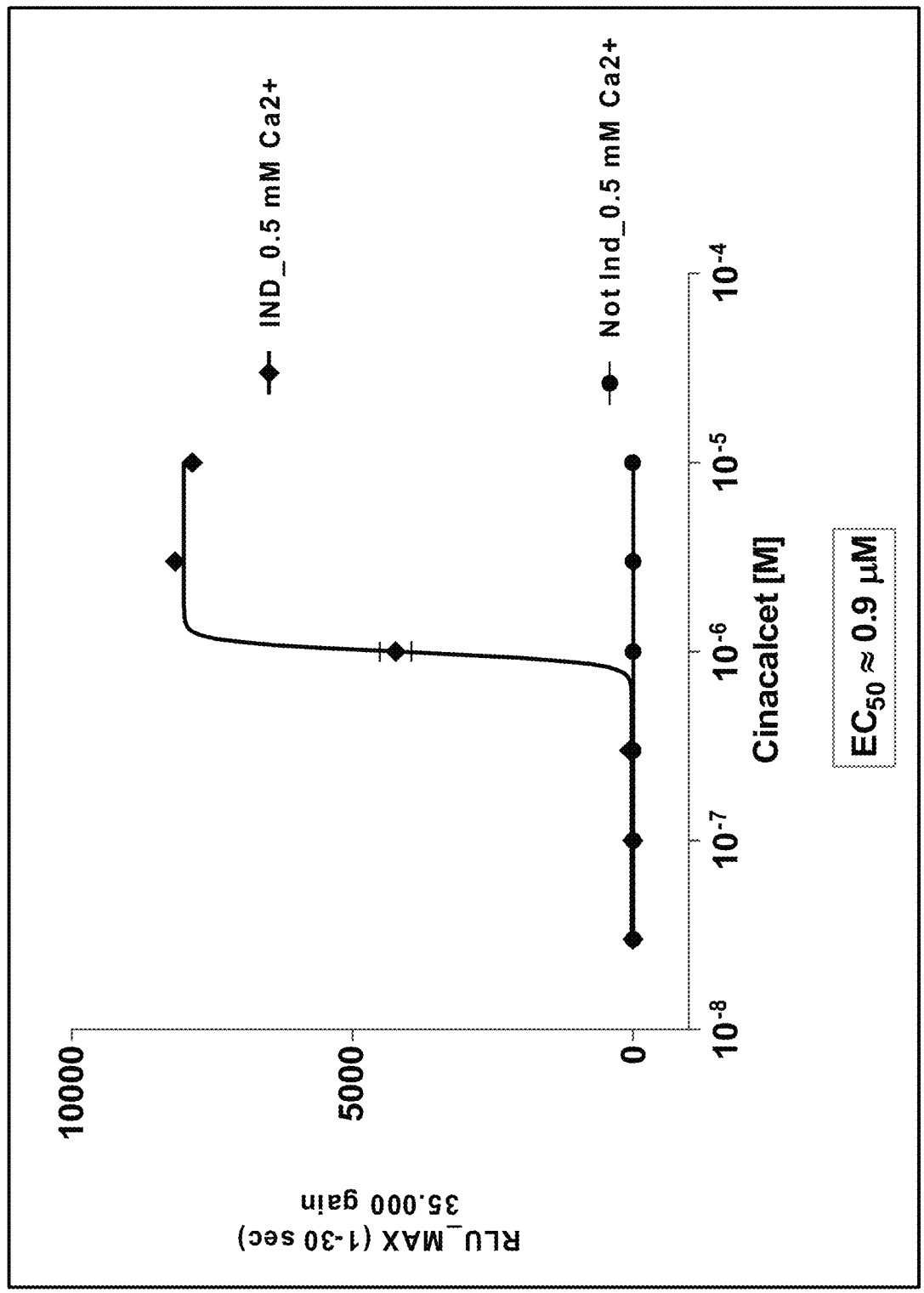
FIGS. 19A-19B show dose response curves for 2 fCaSR ligands determined in an in vitro cellular assay for activation of fCaSR by the 2 ligands in PAM mode.
Figure 19B:
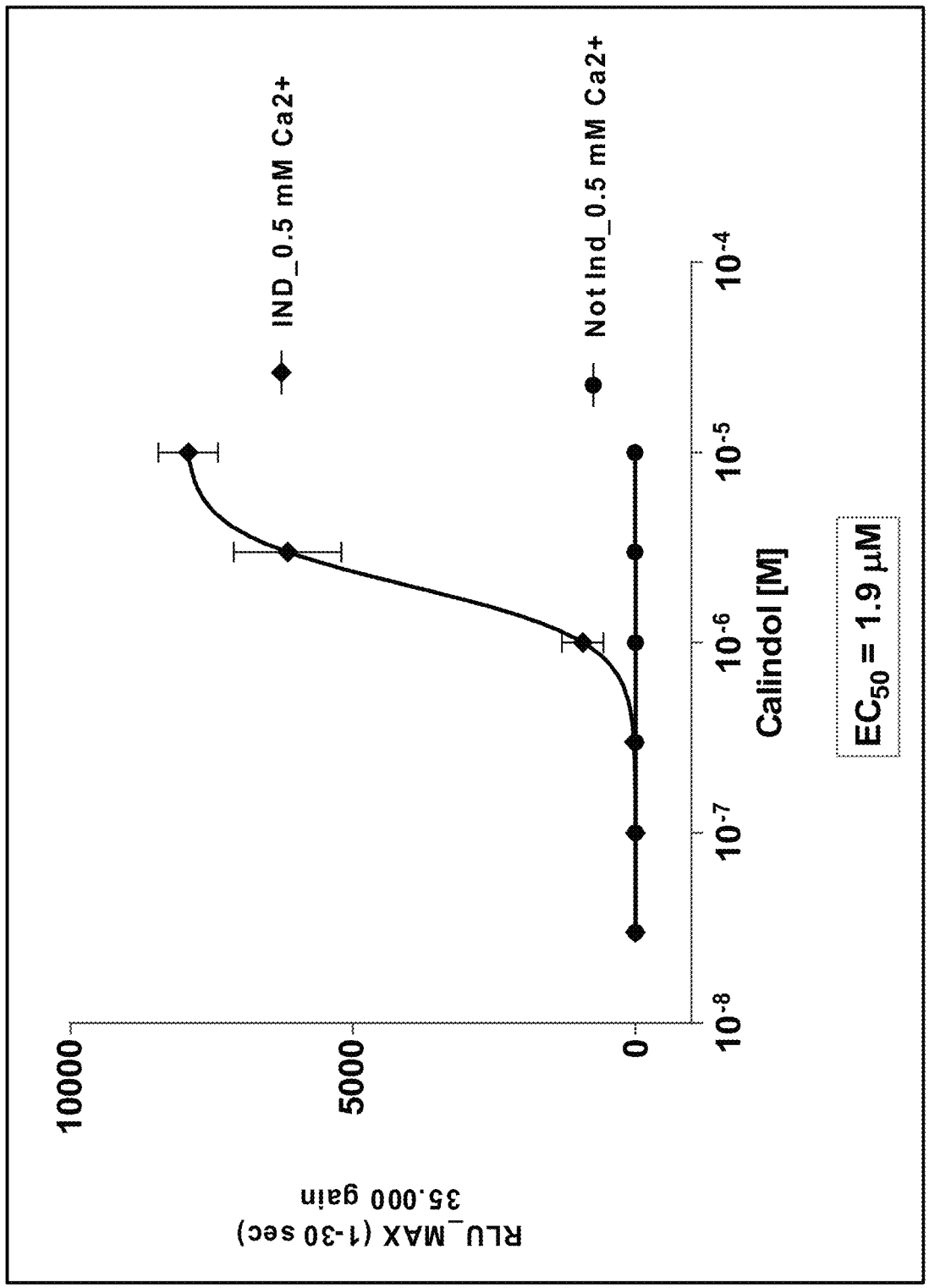

A final pure selected clone (K 5.1) was analyzed in a HTS multi-plate test for agonist or positive allosteric modulator (PAM) effects of 12 CaSR ligands (including calcium as a reference agonist control). 10.000 cw of K 5.1 were seeded on poly-D-lys coated 384 well MTPs in medium containing 1 µg/mL of Doxycycline. Screening with the 12 ligands (including calcium control) was conducted 24 hours later. Dose response curves for the activation of CaSR by the ligands in agonist mode testing are shown in FIG. 18. Dose response curves for the activation of CaSR by the ligands cinacalcet and calindol in PAM mode testing are shown in FIG. 19. As described by Table 2, 7 of the ligands tested (including calcium control) activated CaSR as agonists, and 2 (cinacalcet and calindol) activated CaSR as PAMs. For each ligand that activated CaSR as an agonist or PAM, the $EC_{50}$ value of the ligand was determined. The term half maximal effective concentration ($EC_{50}$) refers to the concentration of a compound which induces a response halfway between the baseline and the maximum after a specified exposure time.

TABLE 2

The Effect of CaSR ligands on CaSR activation as an agonist or PAM

| COMPOUND | MAX dose | Agonist $EC_{50}$ | Enhancer (PAM) $EC_{50}$ |
|---|---|---|---|
| Calcium ($Ca^{2+}$) | 15 mM | 1.5 mM | not active |
| Magnesium ($Mg^{2+}$) | 30 mM | 6.1 mM | not active |
| Spermine | 3 mM | 0.5 mM | Not active |
| Spermidine | 3 mM | 1.3 mM | Not active |
| Putrescine | 30 mM | Not active | Not active |
| L-Glutathione | 30 mM | 8.2 mM | Not active |
| Neomycin | 30 mM | 10 mM | Not active |
| Poly-L-Arginine | 60 µg/mL | 4.6 µg/mL | Not active |
| Cinacalcet | 100 µM | Not active | 1.0 µM |
| Calindol | 100 µM | Not active | 1.9 µM |

Methods

Figure 20:
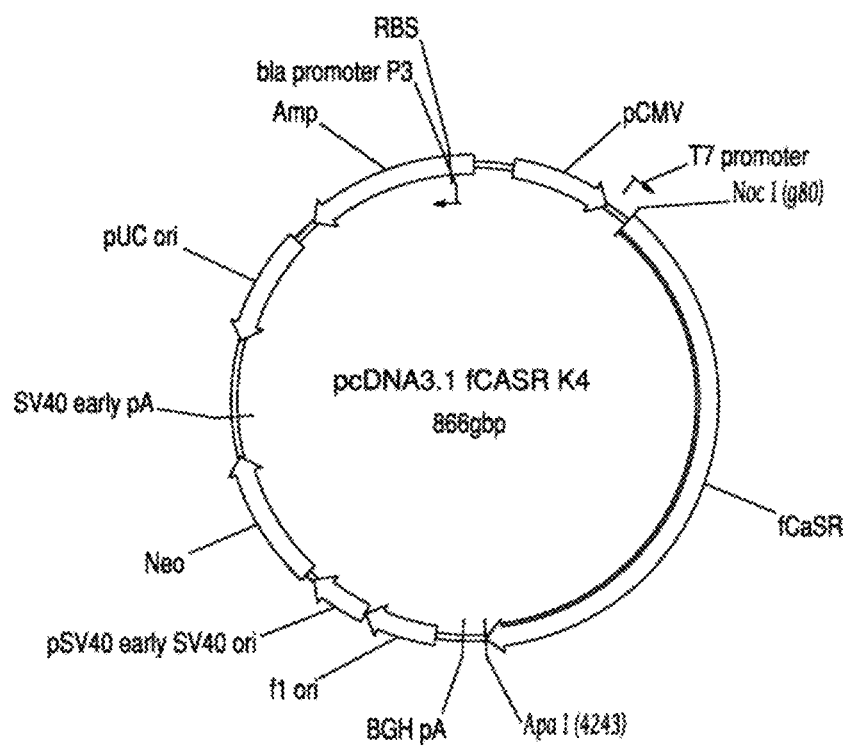
FIG. 20 shows the pcDNA3.1_fCaSR vector clone comprising the fCaSR coding region.

Cloning of the feline calcium-sensitive receptor into a constitutive expression vector. The Felis catus CaSR gene (fCaSR) is encoded by a gene described by GenBank accession no. NM_001164654.1, and expresses a protein described by GenBank accession no. NP_001158126. The fCaSR coding sequence (SEQ ID NO:7) was synthesized by GeneArt (construct 15AAQ7BP_fCaSR_pMK), with Kozak sequence, Y987T, M1066C, R1269G and S3131G. The coding sequence was excised from the construct with 5'NotI-3'ApaI, and inserted into a pcDNA3.1 vector opened with the same restriction enzymes. After restriction analysis with BamHI enzyme for the screening of positive constructs, clone K4, with correct DNA fragmentation (6217+2781 pb), was selected. The presence of the entire fCaSR coding region was confirmed by sequencing. The pcDNA3.1_fCaSR vector clone comprising the fCaSR coding region is shown in FIG. 20.

Figure 21:
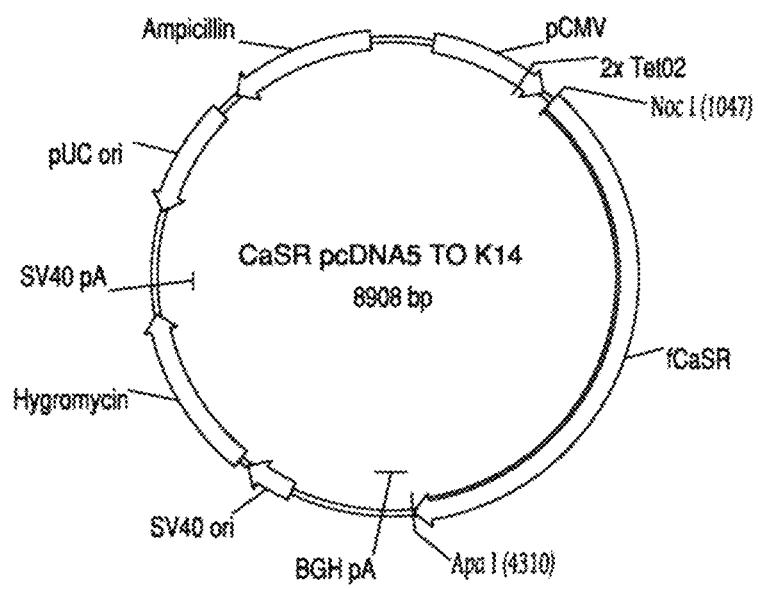
FIG. 21 shows the pcDNA5 TO_fCASR vector clone comprising the fCaSR coding region.

Cloning of the feline calcium-sensitive receptor into an inducible expression vector for the T-REx™ System. The fCaSR coding sequence (SEQ ID NO:7) described above was inserted into a pcDNA5 TO vector opened with the same restriction enzymes. After restriction analysis with BamHI enzyme for the screening of positive constructs, clone K14, with correct DNA fragmentation (5888+2781 pb), was selected. The presence of the entire fCaSR coding region was confirmed by sequencing. The pcDNA5 TO_f-CASR vector clone comprising the fCaSR coding region is shown in FIG. 21.

Transfection of HEK-natClytin and HEK-293 T-REx cell lines. Transfection was performed by electroporation. $2\times10^6$ cells detached from 60-70% confluent flasks were transfected with a total amount of 10 µg of DNA construct by using the Gene Pulser II electroporator (Biorad) (parameters: 300 Volts, 950 µF). Transfected cells were immediately diluted in wild-type complete medium and seeded in T75 flasks. After 48 h, the proper antibiotic concentration was added to the medium and cells were cultured at 37° C. 5% $CO_2$ for about 3 weeks to generate stable pools.

Detection of CaSR receptor activation. Transfected cells were analyzed for a response to a reference agonist (calcium) or various CaSR ligands by detecting $Ca^{2+}$ sensitive photoprotein luminescence. The experiments were performed in a 384 well format according to one of the following procedures:

7.500 cw were plated on poly-D-lys coated 384 well microtiter plates (MTPs). 24 h later, medium was manually discarded and replaced with fresh medium containing 1 µg/mL of Doxycycline. Experiments were then carried out 48 h after seeding.

10.000 cw were plated on poly-D-lys coated 384 well MTPs in medium containing 1 µg/mL of Doxycycline. Experiments were carried out 24 hrs later.

On the day of the experiment, medium was removed by plate overthrow and tapping on a paper towel. Cells were then incubated for 3-4 hrs at 37° C. with 10 µM coelenterazine dissolved in 2 mM $Ca^{2+}$ or $Ca^{2+}$-Free Tyrode's Buffer (20 µL). Cells were exposed to calcium control and/or ligand and the luminescence changes over a period of 1 minute (at 35.000 gain of sensitivity) were monitored using a FLIPR® Tetra screening system. For agonist evaluation, a single exposure protocol was applied (ligands 1° injection, 20 µL-2×), whereas for PAM evaluation a double injection protocol was applied as following:

1° injection: ligands dose-response (20 µL-2×)
   2° injection: Reference agonist EC20 (20 µL-3×)

Data Analysis. FLIPR® Tetra measurements were analysed with Screenworks© software (Molecular Devices, Version 3.0.1.4) and data were exported as Maximum statistics of Absolute Response (RLU) calculated after compound injection. RLU is obtained applying "Subtract Bias on Sample n" (where n=Time point of compound injection). Mean and standard deviation values were calculated on the exported data with Excel software, and then values were used to create sigmoidal dose-response curves (variable slope) or histograms with GraphPad PRISM® software (Version 6). The obtained $EC_{50}/IC_{50}$ values were used to calculate $EC_{50}/IC_{100}$ values according to the following formula:

$$EC_X=[(X/100-X)1/\text{HillSlope}]*EC_{50}$$

As the calculated $IC_{100}$ value would be infinite, the $IC_{99}$ value was calculated as an approximation. The robust Z prime (RZ'), the Intraplate Variability and the Interplate Variability were calculated onto minimum (Control Reference, CR) well signals and maximum (Signal Reference, SR) well signals, according to the following formulae:

$$RZ' = 1 - \frac{3*(RSD_{CR}+RSD_{SR})}{|\langle CR \rangle - \langle SR \rangle|}$$

$$\text{VariabilityIntraplate\_CR(p)} = \frac{RSD_{CR}(p)}{|\langle SR \rangle - \langle CR \rangle|}*100$$

$$\text{VariabilityIntraplate\_SRp} = \frac{RSD_{SR}(p)}{|\langle SR \rangle - \langle CR \rangle|} * 100$$

$$\text{VariabilityInterplate\_CR}(p, d) = \frac{\langle CR(p) \rangle - \overline{\langle CR(p, d) \rangle}}{|\overline{\langle CR(p, d) \rangle} - \overline{\langle SR(p, d) \rangle}|} * 100$$

$$\text{VariabilityInterplate\_SR}(p, d) = \frac{\langle SR(p) \rangle - \overline{\langle SR(p, d) \rangle}}{|\overline{\langle CR(p, d) \rangle} - \overline{\langle SR(p, d) \rangle}|} * 100$$

Cell lines, Medium and Culture Conditions. The experiments were done using HEK-natClytin or HEK T-Rex/natClytin reporter cell lines that were generated by stable transfection of the photoprotein natClytin into HEK-293 or HEK-293 T-Rex (HEK T-Rex, Invitrogen) cell lines respectively.

Culture medium: HEK-natClytin cell line. Minimum Essential Medium Eagle with Earle's Salts (EMEM, BioWhittaker cat. BE12-125F); 10% FBS (Fetal Bovine Serum, Sigma cat. F7524); 1% Penicillin-Streptomycin (BioWhittaker cat. DE17-602E); 2 mM Ultraglutamine 1 (BioWhittaker cat. BE17-605E/U1), 0.2 µg/mL of Puromicin (InvivoGen cat. ant-pr-1). HEK-natClytin/fCaSR cell medium was supplemented with 0.8 mg/mL G418 (InvivoGen cat. ant-gn-5).

Culture medium: HEK-293 T-REx cell line. DMEM High Glucose (Lonza BioWhittaker cat. BE12-604F/U1; 500 mL) supplemented with Fetal Bovine Serum TET-FREE (Euroclone cat. EC 50182L; 50 mL), Penicillin-Streptomycin (BioWhittaker, cat. DE17-602E; 5 mL of 100× Solution), Blasticidin 5 µg/ml (InvivoGen, cat. ant-bl-1). HEK T-Rex/natClytin cell medium was supplemented with 1 µg/mL of Puromicin (InvivoGen cat. ant-pr-1). HEK T-Rex/natClytin-fCaSR cell medium was supplemented with 0.5 µg/mL of Puromicin and 50 µg/mL of Hygromycin (InvivoGen cat. ant-hg-5) during selection and then maintained in medium supplemented with 0.25 µg/mL of Puromicin and 25 µg/mL of Hygromycin.

Culture and seeding conditions. Cells were split every 3-4 days by gentle wash with PBS, followed by 5 min. incubation at 37° C. with Trypsin. Detached cells were diluted with complete medium and counted using the Becman Coulter Z1TM Particle Counter. The desired number of cell was plated into a new flask or used for adherent experiments. 1.5-2.0×10$^6$ cells were seeded in a T75 flask twice a week, recovering about 10-12×10$^6$ cells at ~80% confluence after 3-4 days. As an alternative, an 80% confluent flask could be diluted 1:5-1:10 twice a week.

For experimental conditions, cells were plated on poly-D-lys coated 384 well MTPs according to one of the following conditions:
  7.500 cw. 24 h later, medium was manually discarded and replaced with fresh medium containing 1 µg/mL of Doxycycline. Experiments were then carried out 48 h after seeding.
  10.000 cw in medium containing 1 µg/mL of Doxycycline. 24 h later experiments were then carried out.
Buffers and Ligands. The following buffers and ligands were used in the present study:
  PBS: D-PBS without calcium and magnesium; EuroClone, cat. ECB4004L.
  Trypsin: Trypsin—0.05% EDTA 0.02% in PBS: EuroClone, cat. EC B3052D.
  Doxycycline: Sigma, cat. D9891; 20 mg/mL stock solution is prepared in water and stored in the dark at −20° C.
  2 mM Ca$^{2+}$ Tyrode's Buffer: 130 mM NaCl, 5 mM KCl, 2 mM CaCl$_2$, 5 mM NaHCO$_3$, 1 mM MgCl$_2$, 20 mM HEPES, pH 7.4 sterile filtered and autoclaved.
  Ca$^{2+}$-Free Tyrode's Buffer: 130 mM NaCl, 5 mM KCl, 1 mM MgCl$_2$, 5 mM NaHCO$_3$, 20 mM HEPES; pH 7.4 sterile filtered and autoclaved.
  Dimethyl sulfoxide (DMSO): Sigma, cat. 34869.
  Coelenterazine: (Biosynth, cat. C-7001), 5 mg/mL prepared in DMSO-Glutathione 30 µM (Sigma G-6529), stored in aliquots at −20° C.
  Calcium chloride (dihydrate): Sigma, cat. 223506, 1 M stock solution, prepared in water and stored at RT.
  Spermine: Sigma, cat. 53256, 100 mM stock solution, prepared in 100% DMSO, stored in aliquots at −20° C.
  Spermidine: Sigma, cat. 52626, 100 mM stock solution, prepared in 100% DMSO, stored in aliquots at −20° C.
  Putrescine: Sigma, cat. P7505, 100 mM stock solution, prepared in water and stored in aliquots at −20° C.
  L-Glutathione (γ-Glu-Cys-Gly): Sigma, cat. G6013, 100 mM stock solution, prepared in water and stored in aliquots at −20° C.
  Neomycin: InvivoGen, cat. ant-gn-1, 50 mg/mL G418 sol, stored at 4° C.
  Poly-L-Arginine (hydrochloride): Sigma, cat. P7762, 100 ug/mL stock solution, prepared in 100% DMSO, stored in aliquots at −20° C.
  Cinacalcet (hydrochloride): Cayman Chemical, cat. 16042, 100 mM stock solution, prepared in 100% DMSO, stored in aliquots at −20° C.
  Calindol (hydrochloride): SantaCruzBiotech (DBA), cat. sc-211006, 100 mM stock solution, prepared in 100% DMSO, stored in aliquots at −20° C.
  Magnesium chloride (hexahydrate): Sigma, cat. M2393, 1 M stock solution, prepared in water and stored at RT.
  Instrumentation and Disposables. Experiments were performed using the ICCD camera FLIPR® Tetra (MDC). The analysis was performed in 384-well polystyrene assay plates.
Test plates: Poly-D-lysine coated 384 Well Assay Plates (MTP), Black/clear bottom, MATRIX, cat. CPL-4332.
Compound plates: 384 Well Polypropylene Assay Plates, V bottom, MATRIX, cat. 4312.

Although the presently disclosed subject matter and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, and composition of matter, means, methods and steps described in the specification. As one of ordinary skill in the art will readily appreciate from the disclosure of the presently disclosed subject matter, processes, machines, manufacture, compositions of matter, means, methods, or steps, presently existing or later to be developed that perform substantially the same function or achieve substantially the same result as the corresponding embodiments described herein may be utilized according to the presently disclosed subject matter. Accordingly, the appended claims are intended to include within their scope such processes, machines, manufacture, compositions of matter, means, methods, or steps.

Patents, patent applications, publications, product descriptions and protocols are cited throughout this application the disclosures of which are incorporated herein by reference in their entireties for all purposes.

We claim:

1. A method for identifying a compound that modulates biological activity of a calcium-sensing receptor (CaSR) comprising
   (a) contacting one or more compound with a CaSR, wherein the CaSR comprises an amino acid sequence having at least 97% identity to SEQ ID NO: 4 or 5,
   (b) determining biological activity of the CaSR, and
   (c) selecting the compound as a compound that modulates the biological activity of a CaSR, if the compound increases the biological activity of the CaSR.

2. The method of claim 1, wherein the CaSR is expressed by a cell, and wherein the compound is contacted to the cell.

3. The method of claim 2, wherein the cell expresses a calcium-binding photoprotein.

4. The method of claim 1, wherein the compound increases the biological activity of the CaSR at a concentration of no more than 30 mM.

5. A method for identifying a compound that modulates biological activity of a calcium-sensing receptor (CaSR) comprising
   (a) contacting one or more compound with a CaSR, wherein the CaSR comprises an amino acid sequence having at least 97% identity to SEQ ID NO: 4 or 5,
   (b) detecting binding between the compound and one or more amino acids in a Venus Flytrap domain (VFT) or 7 transmembrane domain (7TM) of the CaSR, and (c) selecting the compound as a compound that modulates the biological activity of a CaSR, if the compound binds to one or more of the amino acids,
   wherein the one or more amino acids is in the VFT selected from the group consisting of ASN64, PHE65, ASN102, THR145, SER169, SER170, ASP190, GLN193, ASP216, TYR218, SER271, SER272, GLY273, GLU297, ALA298, TRP299, ALA300, SER301, SER302, LEU304, ALA321, TYR411, THR412, and HIS413 of SEQ ID NO: 4 or 5, or in the 7TM selected from the group consisting of ARG680; PHE684; GLY685; PHE688; VAL689 on Helix 3; GLN735 on Helix 4; ALA772; PHE775; LEU776; THR780; CYS781 on Helix 5; PHE814; VAL817; TRP818; PHE821 on Helix 6; GLU837; ALA840; ILE841; ALA844 on Helix 7; MET771 and GLU767 on EC2 loop of SEQ ID NO: 4 or 5.

6. The method of claim 5, wherein the method comprises detecting binding between the compound and one or more amino acids in a hinge region or backbone region of the VFT.

7. The method of claim 5, wherein the method comprises detecting binding between the compound and one or more amino acids in the VFT selected from the group consisting of ASN64, PHE65, ASN102, THR145, SER169, SER170, ASP190, GLN193, ASP216, TYR218, SER271, SER272, GLY273, GLU297, ALA298, TRP299, ALA300, SER301, SER302, LEU304, ALA321, TYR411, THR412, and HIS413 of SEQ ID NO: 4 or 5.

8. The method of claim 5, wherein the method comprises detecting binding between the compound and one or more amino acids in the 7TM selected from the group consisting of ARG680; PHE684; GLY685; PHE688; VAL689 on Helix 3; GLN735 on Helix 4; ALA772; PHE775; LEU776; THR780; CYS781 on Helix 5; PHE814; VAL817; TRP818; PHE821 on Helix 6; GLU837; ALA840; ILE841; ALA844 on Helix 7; MET771 and GLU767 on EC2 loop of SEQ ID NO: 4 or 5.

9. The method of claim 5, further comprising determining the biological activity of the CaSR after step (a).

10. The method of claim 9, wherein step (c) further comprises selecting the compound as a compound that modulates the activity of a CaSR, if the compound increases the biological activity of the CaSR at a concentration of no more than 30 mM.

11. The method of claim 10, wherein the compound increases the biological activity of the CaSR at a concentration of no more than 10 mM.

12. The method of claim 5, further comprising contacting a CaSR ligand to the CaSR.

13. A method for identifying a compound that modulates biological activity of a calcium-sensing receptor (CaSR) comprising
   (a) contacting a CaSR agonist with a CaSR, wherein the CaSR comprises an amino acid sequence having at least 97% identity to SEQ ID NO: 4 or 5,
   (b) determining biological activity of the CaSR,
   (c) contacting one or more compound with the CaSR,
   (d) determining biological activity of the CaSR, and
   (e) selecting the compound as a compound that modulates the biological activity of a CaSR if the biological activity of (d) is greater than the biological activity of (b).

14. The method of claim 13, wherein the biological activity of (d) is greater than the biological activity of (b) when the compound is at a concentration of no more than 100 μM.

15. A method for identifying a compound that increases biological activity of a calcium-sensing receptor (CaSR) comprising:
   (a) contacting a CaSR with one or more compound, wherein the CaSR comprises an amino acid sequence having at least 97% identity to SEQ ID NO: 4 or 5,
   (b) measuring biological activity of the CaSR in the absence and in the presence of the compound, and
   (c) identifying the compound as a compound that increases biological activity of a CaSR, when the biological activity is increased in the presence of the compound compared to the absence of the compound.

* * * * *

SEQUENCE LISTING

<160> NUMBER OF SEQ ID NOS: 7

<210> SEQ ID NO 1
<211> LENGTH: 3246
<212> TYPE: DNA
<213> ORGANISM: Felis catus

<400> SEQUENCE: 1

```
atggcatttt atagctgctg tttgatcctc ttggcaatta cctggtgcac ttctgcctat     60
gggcctgacc aacgagctca agaagaaggg gacattatcc tcgggggggct ctttcctatt    120
cattttggag tagcagccaa agatcaagat ctaaagtcaa ggccagagtc tgtggaatgt    180
atcaggtata atttccgtgg gtttcgctgg ttacaagcaa tgatatttgc catcgaggaa    240
ataaacagca gcccagtcct tcttcccaac atgacactgg gatacaggat atttgacact    300
tgcaacactg tttctaaagc cttggaggcc actctgagtt tgtggcaca aaataaaatt      360
gattctctga acctcgacga gttctgcaac tgctcagagc atatccctc tactatcgct     420
gtggtgggag caactggttc gggcatctcc acagcggtgg caaacctgct gggcctcttc    480
tatattcccc aggtcagcta tgcctcctcc agcagactcc tcagcaacaa aaatcagttc    540
aagtccttc tccgtaccat ccccaatgat gaacaccagg ccactgccat ggcagacatt     600
atcgagtatt ccgctggaa ctgggtgggc acaattgctg ctgatgatga ctacggccgg     660
ccagggattg agaagtttcg agaggaagct gaggagaggg acatctgcat cgacttcagt    720
gaactcatct cccagtattc tgatgaagaa gagatccagc aagtggtgga ggtgatccag    780
aattccacag ccaaagtcat tgttgttttc tctagtggcc cagaccttga acccttatc     840
aaggagattg tccggcgtaa tatcacaggg aggatctggc tggccagcga ggcctgggcc    900
agctcttcct tgattgccat gcccgagtac ttccatgtgg ttggaggcac cattggattc    960
gctctgaagg ctggacagat cccaggtttc cgggaattcc tgcagaaagt ccatcccaga   1020
aagtctgtcc acaatggttt tgccaaggag ttttgggaag aaaccttaa ctgccacctc    1080
caagaaggtg ctaaaggacc tttagcactg gacactttcc tgagaggtca tgaagaaggt   1140
ggtggcagga taagcaatag ctccactgcc ttgcgacctc tctgtacagg ggacgagaac   1200
atcagcagcg tggagacccc ttacatggat tatacacatt tacggatatc ctacaatgtc   1260
tacttagcgg tctattccat tgctcatgcc ctgcaagata tatatacatg cttacctgga   1320
agagggctct tcaccaatgg ttcctgcgca gatatcaaga aggttgaggc ttggcaggtc   1380
ctgaagcacc tacggcacct aaactttacc aacaatatgg gggagcaggt gactttcgat   1440
gaatgtgggg acctggtggg gaactattcc atcatcaact ggcacctctc tccagaggat   1500
ggctccatag tgtttaagga agtcggatat tacaacgtct atgccaagaa aggagaaagg   1560
ctcttcatca atgaggagaa aatcctgtgg agtggattct ccaggaggt acctttctcc    1620
aactgcagtc gagactgcct ggcagggacc cggaaaggaa tcattgaggg ggagcccacc   1680
tgctgctttg agtgtgtgga atgtcctgat ggggagtaca gtgatgaaac agatgcaagt   1740
gcctgtgaca agtgccccga tgacttctgg tccaatgaga ccacacttc ttgcattgcc    1800
aaggagattg agtttctgtc ctggacggag ccctttggga ttgcactcac tctcttgct    1860
gtgctgggca ttttcctgac agccttcgtg ctgggtgtct tcctcaagtt ccgtaacaca   1920
cccattgtca aggctaccaa tcgagagctc tcctacctcc tcctcttctc cttgctctgc   1980
tgcttctcca gctccctgtt cttcattggt gagccccagg actggacatg ccgcctgcgc   2040
cagccagcct ttggcatcag cttcgtgctc tgcatatcat gcatcctagt gaaaaccaac   2100
```

```
cgtgtcctcc tggtgtttga ggccaagatc cccacgagct tccaccgcaa gtggtggggg    2160
ctcaacctgc agttcctgct ggtcttcctc tgcaccttca tgcagattgt catctgtgtg    2220
atctggctct acactgcacc accctcaagc taccgcaacc acgagctgga ggatgagatc    2280
atctttatca catgccacga gggctcgctc atggccctgg gcttcttaat tggctacacc    2340
tgcctactgg ctgccatctg cttcttcttt gccttcaagt cccggaagct gccagagaat    2400
ttcaatgaag ccaagttcat caccttcagc atgctcatct tcttcatcgt ctggatctcc    2460
ttcatcccag cctatgccag cacctatggc aagtttgtct ctgccgtgga agtgatcgcc    2520
atcctggcag ccagctttgg cttgctggcc tgcatcttct tcaacaaggt ctacatcatc    2580
ctcttcaagc catcacgtaa caccatcgag gaggtgcgct gcagcactgc tgcccatgct    2640
ttcaaagtag cagcccgggc cacgctgcgc cgcagcaacg tctctcgcaa gcggccagc     2700 agccttgggg gctccacggg atccacaccc tcttcctcca tcagcagtaa gagcaacagt    2760
gaagacccct tcccacagcc cgagaggcaa aagcagcagc agccactggc cctgacccaa    2820
caagagcagc agccgcagcc acagcagccc tcgtccctac agcagcagcc acagccacag    2880
ccacagccca gatgcaagca gaaagtcatt ttcggcagtg gcacagtcac cttctcactg    2940
agctttgatg agcctcagaa gagtgccatg gctcacagga attctatgca ccagaactcc    3000
ctggaggccc agaaaagcaa tgagaccctc accagacacc aggcattact cccactacag    3060
tgcggggaga cagactcaga actgagtgcc caggagagag gtcttcaagg gcctgtagat    3120
ggggacttcc gaccagagat ggaggaccct gaagagatgt ccccagcgct tgtagtgtcc    3180
agttcacaaa gctttgtcat cagtggtggt ggcagcactg tcacagaaaa tatactgcat    3240
tcataa                                                                3246
```

<210> SEQ ID NO 2
<211> LENGTH: 3228
<212> TYPE: DNA
<213> ORGANISM: Canis lupus
<220> FEATURE:
<223> OTHER INFORMATION: Canis lupus familiaris

<400> SEQUENCE: 2

```
atggcatttc acagctgctc tttgatcctc ttggcaatca cctggtgcac ttctgcctat      60
gggcctgacc aacgagccca gaagaaaggg gacattatcc ttgggggct ctttcctatt     120 cattttggag tagcagccaa agatcaagat ctaaagtcaa ggccggagtc tgtggaatgt     180
atcaggtaca atttccgcgg gtttcgttgg ttacaagcaa tgatatttgc catcgaggaa     240
ataaacagca gcccagccct tcttccaaac atgacactgg atacagaat atttgacact     300 tgcaacaccg tttctaaagc cttggaggcc actctgagtt ttgtggcaca gaataaaatt     360
gattctctga accttgacga gttctgcaac tgctcagagc atatcccctc tactatcgct     420
gtggtgggag caactggctc gggcatctcc acggctgtgg caaacctgct gggcctcttc     480
tacatccccc aggtcagcta tgcctcctcc agcagactcc tcagcaataa gaatcagttc     540
aagtccttcc tccgtaccat ccccaatgat gaacaccagg ccactgccat ggcagacatt     600
attgagtatt tccgctggaa ctgggtgggc accattgcag ctgatgatga ctacggccgg     660
ccagggattg agaagttccg agaggaagca gaggagaggg acatctgcat cgacttcagt     720
gaactcatct cccagtactc tgatgaggaa gagattcagc aagtggtaga ggtgatccag     780
aattccacag ccaaagtcat tgttgttttc tccagtggcc cagaccttga accctcatc     840
```

-continued

```
aaggagatcg tccggcgaaa tatcacagga aggatttggc tggccagtga ggcctgggcc    900
agctcttcct tgattgccat gcccgagtac ttccatgtgg ttggaggtac cattggattc    960
gctttgaagg ctgggcagat cccaggtttc cgggaattcc tgcagaaagt ccatcccaga   1020
aagtctgtcc acaacggttt tgccaaggag ttttgggaag aaacatttaa ctgccacctc   1080
caagaaggtg ctaaagggcc tttatccatg gacactttcc tgagaggcca cgaagaaggt   1140
ggtggcagga taagcaacag ctccactgcc ttccgacctc tttgcacagg agatgagaac   1200
atcagtagtg tggagacccc ttatatggat tatacacact tacggatatc ctacaacgtc   1260
tacttagcag tctattccat tgctcatgcc ctgcaagata tatatacatg cttacctggg   1320
agagggctct tcaccaacgg ttcctgtgct gatattaaga aggttgaggc ttggcaggtc   1380
ttgaagcacc tacggcacct aaactttacc aacaatatgg gggagcaagt gactttcgat   1440
gaatgtggtg acctgatggg gaactattcc atcatcaact ggcacctctc tccagaggat   1500
ggctccatag tgtttaagga agtcggatat tacaatgtct atgccaagaa aggagaaaga   1560
ctcttcatca atgaggagaa aatcctgtgg agtgggttct ccaggagat gccattttcc    1620
aactgcagcc gagactgcct ggcagggacc aggaaaggaa tcattgaggg ggagcctacc   1680
tgctgctttg agtgtgtgga gtgccccgac ggggagtaca gtgatgaaac agatgcaagt   1740
gcctgtgaca gtgccccga tgacttctgg tccaatgaaa accacacttc gtgcattgcc    1800
aaagagattg agtttctgtc ctggacagag ccctttggga ttgcactcac cctctttgct   1860
gtgctgggca ttttcctgac agcttcgtg ctgggggtct tcatcaagtt ccgtaacacg    1920
cccatcgtca aggccaccaa ccgagagctc tcgtacctcc tcctcttctc cttgctgtgc   1980
tgcttctcca gctccctgtt cttcattggc gagccccagg actggacctg ccgcctgcgc   2040
cagccggcct ttggcatcag cttcgtgctc tgcatatcat gcatcctggt gaaaaccaac   2100
cgtgtcctcc tggtgtttga ggccaagatc cccacaagct tccaccgcaa gtggtggggg   2160
ctcaacctgc agttcctgct ggtcttcctc tgcaccttca tgcagattgt catctgtgtg   2220
atctggctct acacggcgcc tccctccagc taccgcaacc atgagctgga ggacgagatc   2280
atcttcatca catgccacga gggctccctg atggccctgg gcttcctgat tggctacacc   2340
tgcctgctgg ctgccatctg cttcttcttt gccttcaagt cccggaagct gccggagaac   2400
ttcaacgagg ccaagttcat caccttcagc atgctcatct tcttcatcgt ctggatctcc   2460
ttcattccag cctacgccag cacctacggc aagtttgtct ctgccgtgga agtgatcgcc   2520
atcctggccg ccagctttgg cctcctggcc tgcatcttct tcaacaaggt gtacatcatc   2580
ctcttcaagc cgtcccgcaa caccatcgag gaggtgcgct gcagcaccgc ggctcacgct   2640
ttcaaggtcg cggcccgcgc cacgctgcgc gcagcaacg tctcccgcaa gcggtccggc    2700
agcctggggg gctccacggg ctccacgccc tcctcctcca tcagcagcaa gagcaacagt   2760
gaagacccct tcccgcagcc cgagaggcag aagcagcagc agcccctggc cctgacccag   2820
cgggagcagc agccgccgca gcccttgacc ttgccgccgc agccgcagcc caggtgcaag   2880
cagaaggtca tcttcggcag tggcaccgtc accttctcgc tgagctttga cgagccgcag   2940
aagagcgccg cggccccccg caattccacg ctgcagcact ccctggaggc ccagcggagc   3000
cccgagcccc ccgccagacc ccaggcgtta ctgccgccgc agggcggaga cacagacgcg   3060
gagctgccgg cccaggagcc gggcctgcag ggccccgggg gtgcggaccg ccgcccggag   3120
atgcgagacc ccgaagagct gtccccagcc ctggtggtgt ccagctcaca aagctttgtc   3180
atcagcggcg gaggcagcac ggtcacggaa acatactgc attcgtaa                 3228
```

<210> SEQ ID NO 3
<211> LENGTH: 3237
<212> TYPE: DNA
<213> ORGANISM: Homo sapiens

<400> SEQUENCE: 3

```
atggcatttt atagctgctg ctgggtcctc ttggcactca cctggcacac ctctgcctac      60
ggccagacc agcgagccca aaagaagggg gacattatcc ttgggggct ctttcctatt       120
cattttggag tagcagctaa agatcaagat ctcaaatcaa ggccggagtc tgtggaatgt     180
atcaggtata atttccgtgg gtttcgctgg ttacaggcta tgatatttgc catagaggag     240
ataaacagca gcccagccct tcttcccaac ttgacgctgg gatacaggat atttgacact     300
tgcaacaccg tttctaaggc cttggaagcc accctgagtt tgttgctca aaacaaaatt      360
gattctttga accttgatga gttctgcaac tgctcagagc acattccctc tacgattgct     420
gtggtgggag caactggctc aggcgtctcc acggcagtgg caaatctgct ggggctcttc     480
tacattcccc aggtcagtta tgcctcctcc agcagactcc tcagcaacaa gaatcaattc     540
aagtcttttcc tccgaaccat ccccaatgat gagcaccagg ccactgccat ggcagacatc    600
atcgagtatt tccgctggaa ctgggtgggc acaattgcag ctgatgacga ctatgggcgg     660
ccggggatt agaaaattccg agaggaagct gaggaaaggg atatctgcat cgacttcagt     720
gaactcatct cccagtactc tgatgaggaa gagatccagc atgtggtaga ggtgattcaa     780
aattccacgg ccaaagtcat cgtggttttc tccagtggcc cagatcttga gcccctcatc     840
aaggagattg tccggcgcaa tatcacgggc aagatctggc tggccagcga ggcctgggcc     900
agctcctccc tgatcgccat gcctcagtac ttccacgtgg ttggcggcac cattggattc     960
gctctgaagg ctgggcagat cccaggcttc cgggaattcc tgaagaaggt ccatcccagg    1020
aagtctgtcc acaatggttt tgccaaggag ttttgggaag aaacatttaa ctgccacctc    1080
caagaaggtg caaaggacc tttacctgtg gacacctttc tgagaggtca cgaagaaagt    1140
ggcgacaggt ttagcaacag ctcgacagca ttccgacccc tctgtacagg ggatgagaac    1200
atcagcagtg tcgagacccc ttacatagat tacacgcatt tacggatatc ctacaatgtg    1260
tacttagcag tctactccat tgcccacgcc ttgcaagata tatacctg cttacctggg     1320
agagggctct tcaccaatgg ctcctgtgca gacatcaaga agttgaggc gtggcaggtc    1380
ctgaagcacc tacggcatct aaactttaca acaatatgg gggagcaggt gacctttgat   1440
gagtgtggtg acctggtggg gaactattcc atcatcaact ggcacctctc cccagaggat   1500
ggctccatcg tgtttaagga agtcgggtat tacaacgtct atgccaagaa gggagaaaga   1560
ctcttcatca acgaggagaa aatcctgtgg agtgggttct ccaggaggt gcccttctcc    1620
aactgcagcc gagactgcct ggcagggacc aggaaaggga tcattgaggg ggagcccacc    1680
tgctgctttg agtgtgtgga gtgtcctgat ggggagtata tgatgagac agatgccagt    1740
gcctgtaaca agtgcccaga tgacttctgg tccaatgaga accacaacctc ctgcattgcc   1800
aaggagatcg agtttctgtc gtggacggag ccctttggga tcgcactcac cctcttttgcc  1860
gtgctgggca ttttcctgac agcctttgtg ctgggtgtgt tatcaagtt ccgcaacaca   1920
cccattgtca aggccaccaa ccgagagctc tcctacctcc tcctcttctc cctgctctgc   1980
tgcttctcca gctcccctgtt cttcatcggg gagcccagg actggacgtg ccgcctgcgc   2040
cagccggcct ttggcatcag cttcgtgctc tgcatctcat gcatcctggt gaaaaccaac   2100
```

```
cgtgtcctcc tggtgtttga ggccaagatc cccaccagct tccaccgcaa gtggtggggg      2160
ctcaacctgc agttcctgct ggttttcctc tgcaccttca tgcagattgt catctgtgtg      2220
atctggctct acaccgcgcc cccgtcaagc taccgcaacc aggagctgga ggatgagatc      2280
atcttcatca cgtgccacga gggctccctc atggccctgg gcttcctgat cggctacacc      2340
tgcctgctgg ctgccatctg cttcttcttt gccttcaagt cccggaagct gccggagaac      2400
ttcaatgaag ccaagttcat caccttcagc atgctcatct tcttcatcgt ctggatctcc      2460
ttcattccag cctatgccag cacctatggc aagtttgtct ctgccgtaga ggtgattgcc      2520
atcctggcag ccagctttgg cttgctggcg tgcatcttct tcaacaagat ctacatcatt      2580
ctcttcaagc catcccgcaa caccatcgag gaggtgcgtt gcagcaccgc agctcacgct      2640
ttcaaggtgg ctgcccgggc cacgctgcgc cgcagcaacg tctcccgcaa gcggtccagc      2700
agccttggag gctccacggg atccaccccc tcctcctcca tcagcagcaa gagcaacagc      2760
gaagacccat tcccacagcc cgagaggcag aagcagcagc agccgctggc cctaacccag      2820
caagagcagc agcagcagcc cctgaccctc ccacagcagc aacgatctca gcagcagccc      2880
agatgcaagc agaaggtcat ctttggcagc ggcacggtca ccttctcact gagctttgat      2940
gagcctcaga gaacgccat ggcccacagg aattctacgc accagaactc cctggaggcc      3000
cagaaaagca gcgatacgct gacccgacac gagccattac tcccgctgca gtgcggggaa      3060
acggacttag atctgaccgt ccaggaaaca ggtctgcaag acctgtggg tggagaccag      3120 cggccagagg tggaggaccc tgaagagttg tccccagcac ttgtagtgtc cagttcacag      3180
agctttgtca tcagtggtgg aggcagcact gttacagaaa acgtagtgaa ttcataa      3237
```

<210> SEQ ID NO 4
<211> LENGTH: 1081
<212> TYPE: PRT
<213> ORGANISM: Felis catus

<400> SEQUENCE: 4

```
Met Ala Phe Tyr Ser Cys Cys Leu Ile Leu Leu Ala Ile Thr Trp Cys
1               5                   10                  15

Thr Ser Ala Tyr Gly Pro Asp Gln Arg Ala Gln Lys Lys Gly Asp Ile
            20                  25                  30

Ile Leu Gly Gly Leu Phe Pro Ile His Phe Gly Val Ala Ala Lys Asp
        35                  40                  45

Gln Asp Leu Lys Ser Arg Pro Glu Ser Val Glu Cys Ile Arg Tyr Asn
    50                  55                  60

Phe Arg Gly Phe Arg Trp Leu Gln Ala Met Ile Phe Ala Ile Glu Glu
65                  70                  75                  80

Ile Asn Ser Ser Pro Val Leu Leu Pro Asn Met Thr Leu Gly Tyr Arg
                85                  90                  95

Ile Phe Asp Thr Cys Asn Thr Val Ser Lys Ala Leu Glu Ala Thr Leu
            100                 105                 110

Ser Phe Val Ala Gln Asn Lys Ile Asp Ser Leu Asn Leu Asp Glu Phe
        115                 120                 125

Cys Asn Cys Ser Glu His Ile Pro Ser Thr Ile Ala Val Val Gly Ala
    130                 135                 140

Thr Gly Ser Gly Ile Ser Thr Ala Val Ala Asn Leu Leu Gly Leu Phe
145                 150                 155                 160

Tyr Ile Pro Gln Val Ser Tyr Ala Ser Ser Ser Arg Leu Leu Ser Asn
                165                 170                 175
```

```
Lys Asn Gln Phe Lys Ser Phe Leu Arg Thr Ile Pro Asn Asp Glu His
                180                 185                 190
Gln Ala Thr Ala Met Ala Asp Ile Ile Glu Tyr Phe Arg Trp Asn Trp
            195                 200                 205
Val Gly Thr Ile Ala Ala Asp Asp Tyr Gly Arg Pro Gly Ile Glu
        210                 215                 220
Lys Phe Arg Glu Glu Ala Glu Arg Asp Ile Cys Ile Asp Phe Ser
225                 230                 235                 240
Glu Leu Ile Ser Gln Tyr Ser Asp Glu Glu Ile Gln Gln Val Val
                245                 250                 255
Glu Val Ile Gln Asn Ser Thr Ala Lys Val Ile Val Phe Ser Ser
            260                 265                 270
Gly Pro Asp Leu Glu Pro Leu Ile Lys Glu Ile Val Arg Arg Asn Ile
        275                 280                 285
Thr Gly Arg Ile Trp Leu Ala Ser Glu Ala Trp Ala Ser Ser Ser Leu
    290                 295                 300
Ile Ala Met Pro Glu Tyr Phe His Val Val Gly Gly Thr Ile Gly Phe
305                 310                 315                 320
Ala Leu Lys Ala Gly Gln Ile Pro Gly Phe Arg Glu Phe Leu Gln Lys
                325                 330                 335
Val His Pro Arg Lys Ser Val His Asn Gly Phe Ala Lys Glu Phe Trp
            340                 345                 350
Glu Glu Thr Phe Asn Cys His Leu Gln Glu Gly Ala Lys Gly Pro Leu
        355                 360                 365
Ala Leu Asp Thr Phe Leu Arg Gly His Glu Glu Gly Gly Arg Ile
    370                 375                 380
Ser Asn Ser Ser Thr Ala Leu Arg Pro Leu Cys Thr Gly Asp Glu Asn
385                 390                 395                 400
Ile Ser Ser Val Glu Thr Pro Tyr Met Asp Tyr Thr His Leu Arg Ile
                405                 410                 415
Ser Tyr Asn Val Tyr Leu Ala Val Tyr Ser Ile Ala His Ala Leu Gln
            420                 425                 430
Asp Ile Tyr Thr Cys Leu Pro Gly Arg Gly Leu Phe Thr Asn Gly Ser
        435                 440                 445
Cys Ala Asp Ile Lys Lys Val Glu Ala Trp Gln Val Leu Lys His Leu
450                 455                 460
Arg His Leu Asn Phe Thr Asn Asn Met Gly Glu Gln Val Thr Phe Asp
465                 470                 475                 480
Glu Cys Gly Asp Leu Val Gly Asn Tyr Ser Ile Ile Asn Trp His Leu
            485                 490                 495
Ser Pro Glu Asp Gly Ser Ile Val Phe Lys Glu Val Gly Tyr Tyr Asn
        500                 505                 510
Val Tyr Ala Lys Lys Gly Glu Arg Leu Phe Ile Asn Glu Glu Lys Ile
    515                 520                 525
Leu Trp Ser Gly Phe Ser Arg Glu Val Pro Phe Ser Asn Cys Ser Arg
    530                 535                 540
Asp Cys Leu Ala Gly Thr Arg Lys Gly Ile Ile Glu Gly Glu Pro Thr
545                 550                 555                 560
Cys Cys Phe Glu Cys Val Glu Cys Pro Asp Gly Glu Tyr Ser Asp Glu
                565                 570                 575
Thr Asp Ala Ser Ala Cys Asp Lys Cys Pro Asp Asp Phe Trp Ser Asn
            580                 585                 590
Glu Asn His Thr Ser Cys Ile Ala Lys Glu Ile Glu Phe Leu Ser Trp
```

```
              595                 600                 605
Thr Glu Pro Phe Gly Ile Ala Leu Thr Leu Phe Ala Val Leu Gly Ile
        610                 615                 620
Phe Leu Thr Ala Phe Val Leu Gly Val Phe Leu Lys Phe Arg Asn Thr
625                 630                 635                 640
Pro Ile Val Lys Ala Thr Asn Arg Glu Leu Ser Tyr Leu Leu Leu Phe
                645                 650                 655
Ser Leu Leu Cys Cys Phe Ser Ser Leu Phe Phe Ile Gly Glu Pro
        660                 665                 670
Gln Asp Trp Thr Cys Arg Leu Arg Gln Pro Ala Phe Gly Ile Ser Phe
        675                 680                 685
Val Leu Cys Ile Ser Cys Ile Leu Val Lys Thr Asn Arg Val Leu Leu
        690                 695                 700
Val Phe Glu Ala Lys Ile Pro Thr Ser Phe His Arg Lys Trp Trp Gly
705                 710                 715                 720
Leu Asn Leu Gln Phe Leu Leu Val Phe Leu Cys Thr Phe Met Gln Ile
                725                 730                 735
Val Ile Cys Val Ile Trp Leu Tyr Thr Ala Pro Pro Ser Ser Tyr Arg
        740                 745                 750
Asn His Glu Leu Glu Asp Glu Ile Ile Phe Ile Thr Cys His Glu Gly
        755                 760                 765
Ser Leu Met Ala Leu Gly Phe Leu Ile Gly Tyr Thr Cys Leu Leu Ala
        770                 775                 780
Ala Ile Cys Phe Phe Phe Ala Phe Lys Ser Arg Lys Leu Pro Glu Asn
785                 790                 795                 800
Phe Asn Glu Ala Lys Phe Ile Thr Phe Ser Met Leu Ile Phe Phe Ile
                805                 810                 815
Val Trp Ile Ser Phe Ile Pro Ala Tyr Ala Ser Thr Tyr Gly Lys Phe
        820                 825                 830
Val Ser Ala Val Glu Val Ile Ala Ile Leu Ala Ala Ser Phe Gly Leu
        835                 840                 845
Leu Ala Cys Ile Phe Phe Asn Lys Val Tyr Ile Ile Leu Phe Lys Pro
        850                 855                 860
Ser Arg Asn Thr Ile Glu Glu Val Arg Cys Ser Thr Ala Ala His Ala
865                 870                 875                 880
Phe Lys Val Ala Ala Arg Ala Thr Leu Arg Arg Ser Asn Val Ser Arg
                885                 890                 895
Lys Arg Ser Ser Ser Leu Gly Gly Ser Thr Gly Ser Thr Pro Ser Ser
                900                 905                 910
Ser Ile Ser Ser Lys Ser Asn Ser Glu Asp Pro Phe Pro Gln Pro Glu
        915                 920                 925
Arg Gln Lys Gln Gln Gln Pro Leu Ala Leu Thr Gln Gln Glu Gln Gln
        930                 935                 940
Pro Gln Pro Gln Gln Pro Ser Ser Leu Gln Gln Pro Gln Pro Gln
945                 950                 955                 960
Pro Gln Pro Arg Cys Lys Gln Lys Val Ile Phe Gly Ser Gly Thr Val
                965                 970                 975
Thr Phe Ser Leu Ser Phe Asp Glu Pro Gln Lys Ser Ala Met Ala His
                980                 985                 990
Arg Asn Ser Met His Gln Asn Ser  Leu Glu Ala Gln Lys  Ser Asn Glu
        995                 1000                 1005
Thr Leu  Thr Arg His Gln Ala  Leu Leu Pro Leu Gln  Cys Gly Glu
        1010                 1015                 1020
```

```
Thr Asp Ser Glu Leu Ser Ala Gln Glu Arg Gly Leu Gln Gly Pro
    1025            1030                1035

Val Asp Gly Asp Phe Arg Pro Glu Met Glu Asp Pro Glu Glu Met
    1040            1045                1050

Ser Pro Ala Leu Val Val Ser Ser Gln Ser Phe Val Ile Ser
    1055            1060                1065

Gly Gly Gly Ser Thr Val Thr Glu Asn Ile Leu His Ser
    1070            1075                1080

<210> SEQ ID NO 5
<211> LENGTH: 1075
<212> TYPE: PRT
<213> ORGANISM: Canis lupus
<220> FEATURE:
<223> OTHER INFORMATION: Canis lupus familiaris

<400> SEQUENCE: 5

Met Ala Phe His Ser Cys Ser Leu Ile Leu Leu Ala Ile Thr Trp Cys
1               5                   10                  15

Thr Ser Ala Tyr Gly Pro Asp Gln Arg Ala Gln Lys Lys Gly Asp Ile
            20                  25                  30

Ile Leu Gly Gly Leu Phe Pro Ile His Phe Gly Val Ala Ala Lys Asp
        35                  40                  45

Gln Asp Leu Lys Ser Arg Pro Glu Ser Val Glu Cys Ile Arg Tyr Asn
    50                  55                  60

Phe Arg Gly Phe Arg Trp Leu Gln Ala Met Ile Phe Ala Ile Glu Glu
65                  70                  75                  80

Ile Asn Ser Ser Pro Ala Leu Leu Pro Asn Met Thr Leu Gly Tyr Arg
                85                  90                  95

Ile Phe Asp Thr Cys Asn Thr Val Ser Lys Ala Leu Glu Ala Thr Leu
            100                 105                 110

Ser Phe Val Ala Gln Asn Lys Ile Asp Ser Leu Asn Leu Asp Glu Phe
        115                 120                 125

Cys Asn Cys Ser Glu His Ile Pro Ser Thr Ile Ala Val Val Gly Ala
    130                 135                 140

Thr Gly Ser Gly Ile Ser Thr Ala Val Ala Asn Leu Leu Gly Leu Phe
145                 150                 155                 160

Tyr Ile Pro Gln Val Ser Tyr Ala Ser Ser Arg Leu Leu Ser Asn
                165                 170                 175

Lys Asn Gln Phe Lys Ser Phe Leu Arg Thr Ile Pro Asn Asp Glu His
            180                 185                 190

Gln Ala Thr Ala Met Ala Asp Ile Ile Glu Tyr Phe Arg Trp Asn Trp
        195                 200                 205

Val Gly Thr Ile Ala Ala Asp Asp Asp Tyr Gly Arg Pro Gly Ile Glu
    210                 215                 220

Lys Phe Arg Glu Glu Ala Glu Glu Arg Asp Ile Cys Ile Asp Phe Ser
225                 230                 235                 240

Glu Leu Ile Ser Gln Tyr Ser Asp Glu Glu Glu Ile Gln Gln Val Val
                245                 250                 255

Glu Val Ile Gln Asn Ser Thr Ala Lys Val Ile Val Phe Ser Ser
            260                 265                 270

Gly Pro Asp Leu Glu Pro Leu Ile Lys Glu Ile Val Arg Arg Asn Ile
        275                 280                 285

Thr Gly Arg Ile Trp Leu Ala Ser Glu Ala Trp Ala Ser Ser Ser Leu
    290                 295                 300
```

-continued

Ile Ala Met Pro Glu Tyr Phe His Val Gly Gly Thr Ile Gly Phe
305                 310                 315                 320

Ala Leu Lys Ala Gly Gln Ile Pro Gly Phe Arg Glu Phe Leu Gln Lys
            325                 330                 335

Val His Pro Arg Lys Ser Val His Asn Gly Phe Ala Lys Glu Phe Trp
            340                 345                 350

Glu Glu Thr Phe Asn Cys His Leu Gln Glu Gly Ala Lys Gly Pro Leu
            355                 360                 365

Ser Met Asp Thr Phe Leu Arg Gly His Glu Glu Gly Gly Arg Ile
370                 375                 380

Ser Asn Ser Ser Thr Ala Phe Arg Pro Leu Cys Thr Gly Asp Glu Asn
385                 390                 395                 400

Ile Ser Ser Val Glu Thr Pro Tyr Met Asp Tyr Thr His Leu Arg Ile
                405                 410                 415

Ser Tyr Asn Val Tyr Leu Ala Val Tyr Ser Ile Ala His Ala Leu Gln
                420                 425                 430

Asp Ile Tyr Thr Cys Leu Pro Gly Arg Gly Leu Phe Thr Asn Gly Ser
            435                 440                 445

Cys Ala Asp Ile Lys Lys Val Glu Ala Trp Gln Val Leu Lys His Leu
450                 455                 460

Arg His Leu Asn Phe Thr Asn Asn Met Gly Glu Gln Val Thr Phe Asp
465                 470                 475                 480

Glu Cys Gly Asp Leu Met Gly Asn Tyr Ser Ile Ile Asn Trp His Leu
                485                 490                 495

Ser Pro Glu Asp Gly Ser Ile Val Phe Lys Glu Val Gly Tyr Tyr Asn
                500                 505                 510

Val Tyr Ala Lys Lys Gly Glu Arg Leu Phe Ile Asn Glu Glu Lys Ile
            515                 520                 525

Leu Trp Ser Gly Phe Ser Arg Glu Met Pro Phe Ser Asn Cys Ser Arg
530                 535                 540

Asp Cys Leu Ala Gly Thr Arg Lys Gly Ile Ile Glu Gly Glu Pro Thr
545                 550                 555                 560

Cys Cys Phe Glu Cys Val Glu Cys Pro Asp Gly Glu Tyr Ser Asp Glu
                565                 570                 575

Thr Asp Ala Ser Ala Cys Asp Lys Cys Pro Asp Asp Phe Trp Ser Asn
            580                 585                 590

Glu Asn His Thr Ser Cys Ile Ala Lys Glu Ile Glu Phe Leu Ser Trp
            595                 600                 605

Thr Glu Pro Phe Gly Ile Ala Leu Thr Leu Phe Ala Val Leu Gly Ile
            610                 615                 620

Phe Leu Thr Ala Phe Val Leu Gly Val Phe Ile Lys Phe Arg Asn Thr
625                 630                 635                 640

Pro Ile Val Lys Ala Thr Asn Arg Glu Leu Ser Tyr Leu Leu Leu Phe
            645                 650                 655

Ser Leu Leu Cys Cys Phe Ser Ser Ser Leu Phe Phe Ile Gly Glu Pro
            660                 665                 670

Gln Asp Trp Thr Cys Arg Leu Arg Gln Pro Ala Phe Gly Ile Ser Phe
            675                 680                 685

Val Leu Cys Ile Ser Cys Ile Leu Val Lys Thr Asn Arg Val Leu Leu
            690                 695                 700

Val Phe Glu Ala Lys Ile Pro Thr Ser Phe His Arg Lys Trp Trp Gly
705                 710                 715                 720

```
Leu Asn Leu Gln Phe Leu Leu Val Phe Leu Cys Thr Phe Met Gln Ile
            725                 730                 735

Val Ile Cys Val Ile Trp Leu Tyr Thr Ala Pro Pro Ser Ser Tyr Arg
        740                 745                 750

Asn His Glu Leu Glu Asp Glu Ile Ile Phe Ile Thr Cys His Glu Gly
            755                 760                 765

Ser Leu Met Ala Leu Gly Phe Leu Ile Gly Tyr Thr Cys Leu Leu Ala
    770                 775                 780

Ala Ile Cys Phe Phe Phe Ala Phe Lys Ser Arg Lys Leu Pro Glu Asn
785                 790                 795                 800

Phe Asn Glu Ala Lys Phe Ile Thr Phe Ser Met Leu Ile Phe Phe Ile
                805                 810                 815

Val Trp Ile Ser Phe Ile Pro Ala Tyr Ala Ser Thr Tyr Gly Lys Phe
                820                 825                 830

Val Ser Ala Val Glu Val Ile Ala Ile Leu Ala Ala Ser Phe Gly Leu
            835                 840                 845

Leu Ala Cys Ile Phe Phe Asn Lys Val Tyr Ile Ile Leu Phe Lys Pro
    850                 855                 860

Ser Arg Asn Thr Ile Glu Glu Val Arg Cys Ser Thr Ala Ala His Ala
865                 870                 875                 880

Phe Lys Val Ala Ala Arg Ala Thr Leu Arg Arg Ser Asn Val Ser Arg
                885                 890                 895

Lys Arg Ser Gly Ser Leu Gly Gly Ser Thr Gly Ser Thr Pro Ser Ser
                900                 905                 910

Ser Ile Ser Ser Lys Ser Asn Ser Glu Asp Pro Phe Pro Gln Pro Glu
            915                 920                 925

Arg Gln Lys Gln Gln Gln Pro Leu Ala Leu Thr Gln Arg Glu Gln Gln
    930                 935                 940

Pro Pro Gln Pro Leu Thr Leu Pro Pro Gln Pro Gln Pro Arg Cys Lys
945                 950                 955                 960

Gln Lys Val Ile Phe Gly Ser Gly Thr Val Thr Phe Ser Leu Ser Phe
                965                 970                 975

Asp Glu Pro Gln Lys Ser Ala Ala Ala Pro Arg Asn Ser Thr Leu Gln
            980                 985                 990

His Ser Leu Glu Ala Gln Arg Ser Pro Glu Pro Pro Ala Arg Pro Gln
    995                 1000                1005

Ala Leu Leu Pro Pro Gln Gly Gly Asp Thr Asp Ala Glu Leu Pro
    1010                1015                1020

Ala Gln Glu Pro Gly Leu Gln Gly Pro Gly Gly Ala Asp Arg Arg
    1025                1030                1035

Pro Glu Met Arg Asp Pro Glu Leu Ser Pro Ala Leu Val Val
    1040                1045                1050

Ser Ser Ser Gln Ser Phe Val Ile Ser Gly Gly Ser Thr Val
    1055                1060                1065

Thr Glu Asn Ile Leu His Ser
    1070                1075

<210> SEQ ID NO 6
<211> LENGTH: 1078
<212> TYPE: PRT
<213> ORGANISM: Homo sapiens

<400> SEQUENCE: 6

Met Ala Phe Tyr Ser Cys Cys Trp Val Leu Leu Ala Leu Thr Trp His
1               5                   10                  15
```

```
Thr Ser Ala Tyr Gly Pro Asp Gln Arg Ala Gln Lys Lys Gly Asp Ile
             20                  25                  30

Ile Leu Gly Gly Leu Phe Pro Ile His Phe Gly Val Ala Ala Lys Asp
         35                  40                  45

Gln Asp Leu Lys Ser Arg Pro Glu Ser Val Glu Cys Ile Arg Tyr Asn
     50                  55                  60

Phe Arg Gly Phe Arg Trp Leu Gln Ala Met Ile Phe Ala Ile Glu Glu
 65                  70                  75                  80

Ile Asn Ser Ser Pro Ala Leu Leu Pro Asn Leu Thr Leu Gly Tyr Arg
                 85                  90                  95

Ile Phe Asp Thr Cys Asn Thr Val Ser Lys Ala Leu Glu Ala Thr Leu
             100                 105                 110

Ser Phe Val Ala Gln Asn Lys Ile Asp Ser Leu Asn Leu Asp Glu Phe
         115                 120                 125

Cys Asn Cys Ser Glu His Ile Pro Ser Thr Ile Ala Val Val Gly Ala
130                 135                 140

Thr Gly Ser Gly Val Ser Thr Ala Val Ala Asn Leu Leu Gly Leu Phe
145                 150                 155                 160

Tyr Ile Pro Gln Val Ser Tyr Ala Ser Ser Arg Leu Leu Ser Asn
                 165                 170                 175

Lys Asn Gln Phe Lys Ser Phe Leu Arg Thr Ile Pro Asn Asp Glu His
             180                 185                 190

Gln Ala Thr Ala Met Ala Asp Ile Ile Glu Tyr Phe Arg Trp Asn Trp
         195                 200                 205

Val Gly Thr Ile Ala Ala Asp Asp Asp Tyr Gly Arg Pro Gly Ile Glu
         210                 215                 220

Lys Phe Arg Glu Glu Ala Glu Glu Arg Asp Ile Cys Ile Asp Phe Ser
225                 230                 235                 240

Glu Leu Ile Ser Gln Tyr Ser Asp Glu Glu Ile Gln His Val Val
                 245                 250                 255

Glu Val Ile Gln Asn Ser Thr Ala Lys Val Ile Val Phe Ser Ser
             260                 265                 270

Gly Pro Asp Leu Glu Pro Leu Ile Lys Glu Ile Val Arg Arg Asn Ile
         275                 280                 285

Thr Gly Lys Ile Trp Leu Ala Ser Glu Ala Trp Ala Ser Ser Ser Leu
         290                 295                 300

Ile Ala Met Pro Gln Tyr Phe His Val Val Gly Gly Thr Ile Gly Phe
305                 310                 315                 320

Ala Leu Lys Ala Gly Gln Ile Pro Gly Phe Arg Glu Phe Leu Lys Lys
                 325                 330                 335

Val His Pro Arg Lys Ser Val Asn Gly Phe Ala Lys Glu Phe Trp
             340                 345                 350

Glu Glu Thr Phe Asn Cys His Leu Gln Glu Gly Ala Lys Gly Pro Leu
         355                 360                 365

Pro Val Asp Thr Phe Leu Arg Gly His Glu Glu Ser Gly Asp Arg Phe
     370                 375                 380

Ser Asn Ser Ser Thr Ala Phe Arg Pro Leu Cys Thr Gly Asp Glu Asn
385                 390                 395                 400

Ile Ser Ser Val Glu Thr Pro Tyr Ile Asp Tyr Thr His Leu Arg Ile
                 405                 410                 415

Ser Tyr Asn Val Tyr Leu Ala Val Tyr Ser Ile Ala His Ala Leu Gln
             420                 425                 430
```

-continued

```
Asp Ile Tyr Thr Cys Leu Pro Gly Arg Gly Leu Phe Thr Asn Gly Ser
        435                 440                 445

Cys Ala Asp Ile Lys Lys Val Glu Ala Trp Gln Val Leu Lys His Leu
450                 455                 460

Arg His Leu Asn Phe Thr Asn Asn Met Gly Glu Gln Val Thr Phe Asp
465                 470                 475                 480

Glu Cys Gly Asp Leu Val Gly Asn Tyr Ser Ile Ile Asn Trp His Leu
                485                 490                 495

Ser Pro Glu Asp Gly Ser Ile Val Phe Lys Glu Val Gly Tyr Tyr Asn
            500                 505                 510

Val Tyr Ala Lys Lys Gly Glu Arg Leu Phe Ile Asn Glu Glu Lys Ile
        515                 520                 525

Leu Trp Ser Gly Phe Ser Arg Glu Val Pro Phe Ser Asn Cys Ser Arg
    530                 535                 540

Asp Cys Leu Ala Gly Thr Arg Lys Gly Ile Ile Glu Gly Glu Pro Thr
545                 550                 555                 560

Cys Cys Phe Glu Cys Val Glu Cys Pro Asp Gly Glu Tyr Ser Asp Glu
                565                 570                 575

Thr Asp Ala Ser Ala Cys Asn Lys Cys Pro Asp Asp Phe Trp Ser Asn
            580                 585                 590

Glu Asn His Thr Ser Cys Ile Ala Lys Glu Ile Glu Phe Leu Ser Trp
        595                 600                 605

Thr Glu Pro Phe Gly Ile Ala Leu Thr Leu Phe Ala Val Leu Gly Ile
    610                 615                 620

Phe Leu Thr Ala Phe Val Leu Gly Val Phe Ile Lys Phe Arg Asn Thr
625                 630                 635                 640

Pro Ile Val Lys Ala Thr Asn Arg Glu Leu Ser Tyr Leu Leu Leu Phe
                645                 650                 655

Ser Leu Leu Cys Cys Phe Ser Ser Ser Leu Phe Phe Ile Gly Glu Pro
            660                 665                 670

Gln Asp Trp Thr Cys Arg Leu Arg Gln Pro Ala Phe Gly Ile Ser Phe
        675                 680                 685

Val Leu Cys Ile Ser Cys Ile Leu Val Lys Thr Asn Arg Val Leu Leu
    690                 695                 700

Val Phe Glu Ala Lys Ile Pro Thr Ser Phe His Arg Lys Trp Trp Gly
705                 710                 715                 720

Leu Asn Leu Gln Phe Leu Leu Val Phe Leu Cys Thr Phe Met Gln Ile
                725                 730                 735

Val Ile Cys Val Ile Trp Leu Tyr Thr Ala Pro Pro Ser Ser Tyr Arg
            740                 745                 750

Asn Gln Glu Leu Glu Asp Glu Ile Ile Phe Ile Thr Cys His Glu Gly
        755                 760                 765

Ser Leu Met Ala Leu Gly Phe Leu Ile Gly Tyr Thr Cys Leu Leu Ala
    770                 775                 780

Ala Ile Cys Phe Phe Phe Ala Phe Lys Ser Arg Lys Leu Pro Glu Asn
785                 790                 795                 800

Phe Asn Glu Ala Lys Phe Ile Thr Phe Ser Met Leu Ile Phe Phe Ile
                805                 810                 815

Val Trp Ile Ser Phe Ile Pro Ala Tyr Ala Ser Thr Tyr Gly Lys Phe
            820                 825                 830

Val Ser Ala Val Glu Val Ile Ala Ile Leu Ala Ala Ser Phe Gly Leu
        835                 840                 845

Leu Ala Cys Ile Phe Phe Asn Lys Ile Tyr Ile Ile Leu Phe Lys Pro
```

-continued

|   |   |   |   |   |   |   |   |   |   |   |   |
|---|---|---|---|---|---|---|---|---|---|---|---|
|   | 850 |   |   | 855 |   |   |   | 860 |   |   |   |

Ser Arg Asn Thr Ile Glu Glu Val Arg Cys Ser Thr Ala Ala His Ala
865                 870                 875                 880

Phe Lys Val Ala Ala Arg Ala Thr Leu Arg Arg Ser Asn Val Ser Arg
            885                 890                 895

Lys Arg Ser Ser Ser Leu Gly Gly Ser Thr Gly Ser Thr Pro Ser Ser
        900                 905                 910

Ser Ile Ser Ser Lys Ser Asn Ser Glu Asp Pro Phe Pro Gln Pro Glu
    915                 920                 925

Arg Gln Lys Gln Gln Gln Pro Leu Ala Leu Thr Gln Gln Glu Gln Gln
930                 935                 940

Gln Gln Pro Leu Thr Leu Pro Gln Gln Arg Ser Gln Gln Gln Pro
945                 950                 955                 960

Arg Cys Lys Gln Lys Val Ile Phe Gly Ser Gly Thr Val Thr Phe Ser
                965                 970                 975

Leu Ser Phe Asp Glu Pro Gln Lys Asn Ala Met Ala His Arg Asn Ser
            980                 985                 990

Thr His Gln Asn Ser Leu Glu Ala  Gln Lys Ser Ser Asp  Thr Leu Thr
        995                 1000                1005

Arg His  Glu Pro Leu Leu Pro  Leu Gln Cys Gly Glu  Thr Asp Leu
    1010                1015                1020

Asp Leu  Thr Val Gln Glu  Thr Gly Leu Gln Gly  Pro Val Gly Gly
    1025                1030                1035

Asp Gln  Arg Pro Glu Val Glu  Asp Pro Glu Glu  Leu Ser Pro Ala
    1040                1045                1050

Leu Val  Val Ser Ser Ser Gln  Ser Phe Val Ile Ser  Gly Gly Gly
    1055                1060                1065

Ser Thr  Val Thr Glu Asn Val  Val Asn Ser
    1070                1075

<210> SEQ ID NO 7
<211> LENGTH: 3265
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 7
gcggccgcgc caccatggca ttttatagct gctgtttgat cctcttggca attacctggt    60
gcacttctgc ctatgggcct gaccaacgag ctcagaagaa aggggacatt atcctcgggg   120
ggctctttcc tattcatttt ggagtagcag ccaaagatca agatctaaag tcaaggccag   180
agtctgtgga atgtatcagg tataatttcc gtgggtttcg ctggttacaa gcaatgatat   240
ttgccatcga ggaaataaac agcagcccag tccttcttcc caacatgaca ctggatacaa   300
ggatatttga cacttgcaac actgtttcta aagccttgga ggccactctg agttttgtgg   360
cacaaaataa aattgattct ctgaacctcg acgagttctg caactgctca gagcatatcc   420
cctctactat cgctgtggtg ggagcaactg gttcgggcat ctccacagcg gtggcaaacc   480
tgctgggcct cttctatatt ccccaggtca gctatgcctc ctccagcaga ctcctcagca   540
acaaaaatca gttcaagtcc tttctccgta ccatccccaa tgatgaacac caggccactg   600
ccatggcaga cattatcgag tatttccgct ggaactgggt gggcacaatt gctgctgatg   660
atgactacgg ccggccaggg attgagaagt ttcgagagga agctgaggag agggacatct   720

```
gcatcgactt cagtgaactc atctcccagt attctgatga agaagagatc cagcaagtgg    780
tggaggtgat ccagaattcc acagccaaag tcattgttgt tttctctagt ggcccagacc    840
ttgaacccct tatcaaggag attgtccggc gtaatatcac agggaggatc tggctggcca    900
gcgaggcctg ggccagctct tccttgattg ccatgcccga gtacttccat gtggttggag    960
gcaccattgg attcgctctg aaggctggac agatcccagg tttccgggaa ttcctgcaga   1020
aagtccatcc cagaaagtct gtccacaatg gttttgccaa ggagttttgg gaagaaacct   1080
ttaactgcca cctccaagaa ggtgctaaag gacctttagc actggacact ttcctgagag   1140
gtcatgaaga aggtggtggc aggataagca atagctccac tgccttgcga cctctctgta   1200
caggggacga aacatcagc agcgtggaga cccttacat ggattataca catttacgga    1260
tatcctacaa tgtctactta gcggtctatt ccattgctca tgccctgcaa gatatatata   1320
catgcttacc tggaagaggg ctcttcacca atggttcctg cgcagatatc aagaaggttg   1380
aggcttggca ggtcctgaag cacctacggc acctaaactt taccaacaat atgggggagc   1440
aggtgacttt cgatgaatgt ggggacctgg tggggaacta ttccatcatc aactggcacc   1500
tctctccaga ggatggctcc atagtgttta aggaagtcgg atattacaac gtctatgcca   1560
agaaaggaga aaggctcttc atcaatgagg agaaaatcct gtggagtgga ttctccaggg   1620
aggtaccttt ctccaactgc agtcgagact gcctggcagg gacccggaaa ggaatcattg   1680
aggggagcc cacctgctgc tttgagtgtg tggaatgtcc tgatggggag tacagtgatg    1740
aaacagatgc aagtgcctgt gacaagtgcc ccgatgactt ctggtccaat gagaaccaca   1800
cttcttgcat tgccaaggag attgagtttc tgtcctggac ggagccccttt gggattgcac   1860
tcactctctt tgctgtgctg ggcattttcc tgacagcctt cgtgctgggt gtcttcctca   1920
agttccgtaa cacacccatt gtcaaggcta ccaatcgaga gctctcctac ctcctcctct   1980
tctccttgct ctgctgcttc tccagctccc tgttcttcat tggtgagccc caggactgga   2040
catgccgcct gcgccagcca gcctttggca tcagcttcgt gctctgcata tcatgcatcc   2100
tagtgaaaac caaccgtgtc ctcctggtgt tgaggccaa gatccccacg agcttccacc    2160
gcaagtggtg ggggctcaac ctgcagttcc tgctggtctt cctctgcacc ttcatgcaga   2220
ttgtcatctg tgtgatctgg ctctacactg caccaccctc aagctaccgc aaccacgagc   2280
tggaggatga gatcatcttt atcacatgcc acgagggctc gctcatggcc ctgggcttct   2340
taattggcta cacctgccta ctggctgcca tctgcttctt cttttgcctt caagtcccgga   2400
agctgccaga gaatttcaat gaagccaagt tcatcacctt cagcatgctc atcttcttca   2460
tcgtctggat ctccttcatc ccagcctatg ccagcaccta tggcaagttt gtctctgccg   2520
tggaagtgat cgccatcctg gcagccagct ttggcttgct ggcctgcatc ttcttcaaca   2580
aggtctacat catcctcttc aagccatcac gtaacaccat cgaggaggtg cgctgcagca   2640
ctgctgccca tgctttcaaa gtagcagccc gggccacgct cgccgcagc aacgtctctc    2700
gcaagcggtc cagcagcctt gggggctcca cgggatccac accctcttcc tccatcagca   2760
gtaagagcaa cagtgaagac ccctttcccac agcccgagag gcaaaagcag cagcagccac   2820
tggccctgac ccaacaagag cagcagccgc agccacagca gccctcgtcc ctacagcagc   2880
agccacagcc acagccacag cccagatgca agcagaaagt cattttcggc agtggcacag   2940
tcaccttctc actgagcttt gatgagcctc agaagagtgc catggctcac aggaattcta   3000
tgcaccagaa ctccctggag gcccagaaaa gcaatgagac cctcaccaga caccaggcat   3060
```

```
tactcccact acagtgcggg gagacagact cagaactgag tgcccaggag agaggtcttc    3120
aagggcctgt agatggggac ttccgaccag agatggagga ccctgaagag atgtccccag    3180
cgcttgtagt gtccagttca caaagctttg tcatcagtgg tggtggcagc actgtcacag    3240
aaaatatact gcattcataa gggcc                                         3265
```